(12) United States Patent
Inoue et al.

(10) Patent No.: US 11,999,892 B2
(45) Date of Patent: Jun. 4, 2024

(54) LIQUID CRYSTAL COMPOSITION, LIQUID CRYSTAL DISPLAY ELEMENT AND COMPOUND

(71) Applicant: DIC Corporation, Tokyo (JP)

(72) Inventors: Yuichi Inoue, Saitama (JP); Daiki Noro, Saitama (JP); Yutaka Kadomoto, Saitama (JP); Hirokazu Sugiyama, Saitama (JP); Noriyuki Sugiyama, Saitama (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 17/908,241

(22) PCT Filed: Dec. 10, 2020

(86) PCT No.: PCT/JP2020/045960
§ 371 (c)(1),
(2) Date: Aug. 31, 2022

(87) PCT Pub. No.: WO2021/192439
PCT Pub. Date: Sep. 30, 2021

(65) Prior Publication Data
US 2023/0131540 A1    Apr. 27, 2023

(30) Foreign Application Priority Data

Mar. 27, 2020 (JP) ................. 2020-057865

(51) Int. Cl.
G02F 1/1333 (2006.01)
C09K 19/12 (2006.01)
C09K 19/20 (2006.01)
C09K 19/32 (2006.01)
C09K 19/34 (2006.01)

(52) U.S. Cl.
CPC .......... C09K 19/3405 (2013.01); C09K 19/12 (2013.01); C09K 19/2028 (2013.01); C09K 19/32 (2013.01); C09K 2019/122 (2013.01); C09K 2019/123 (2013.01)

(58) Field of Classification Search
CPC .......... C09K 19/3405; C09K 19/3804; C09K 19/12; C09K 19/2028; C09K 19/32; C09K 19/3066; C09K 19/3098; C09K 19/322; C09K 19/14; C09K 2019/122; C09K 2019/123; C09K 2019/3004; C09K 2019/0444; C09K 2019/0448; C09K 2019/3009; C09K 2019/301; C09K 2019/3016; C09K 2019/3027; G02F 1/1333

See application file for complete search history.

(56) References Cited

U.S. PATENT DOCUMENTS

| 10,927,300 B2 | 2/2021 | Kimura et al. |
| 11,174,217 B2 * | 11/2021 | Hosono .................. C09K 19/56 |
| 11,345,857 B2 | 5/2022 | Kimura et al. |
| 11,639,327 B2 * | 5/2023 | Hosono .................. C07D 317/38 |
| | | 257/40 |
| 2015/0252265 A1 | 9/2015 | Archetti et al. |
| 2023/0131540 A1 * | 4/2023 | Inoue .................. C07D 319/06 |
| | | 252/299.61 |

FOREIGN PATENT DOCUMENTS

| JP | 2010285499 | 12/2010 |
| JP | 2014112192 | 6/2014 |
| JP | 2015168826 | 9/2015 |
| JP | 2016011347 | 1/2016 |
| JP | 2020177071 | 10/2020 |
| JP | 2020184970 | 11/2020 |
| JP | 2020533168 | 11/2020 |
| TW | 201829367 | 8/2018 |
| WO | 2018079333 | 5/2018 |
| WO | 2018230322 | 12/2018 |
| WO | 2019003935 | 1/2019 |
| WO | 2019003936 | 1/2019 |
| WO | 2019049673 | 3/2019 |
| WO | 2019124092 | 6/2019 |
| WO | 2020071135 | 4/2020 |

OTHER PUBLICATIONS

"International Search Report (Form PCT/ISA/210) of PCT/JP2020/045960," mailed on Feb. 16, 2021, with English translation thereof, pp. 1-6.

\* cited by examiner

*Primary Examiner* — Geraldina Visconti
(74) *Attorney, Agent, or Firm* — JCIPRNET

(57) ABSTRACT

A compound that helps achieve a high voltage holding ratio (VHR) of a liquid crystal composition, a liquid crystal composition that contains this compound, and a liquid crystal display element made with this liquid crystal composition. More specifically, a compound represented by general formula (Y), which has polymerizable groups and polar group(s). A liquid crystal composition containing one or two or more compounds represented by general formula (Y), each of which has polymerizable groups and polar group(s). A liquid crystal display element made with a liquid crystal composition that contains one or two or more compounds represented by general formula (Y), each of which has polymerizable groups and polar group(s).

14 Claims, 1 Drawing Sheet

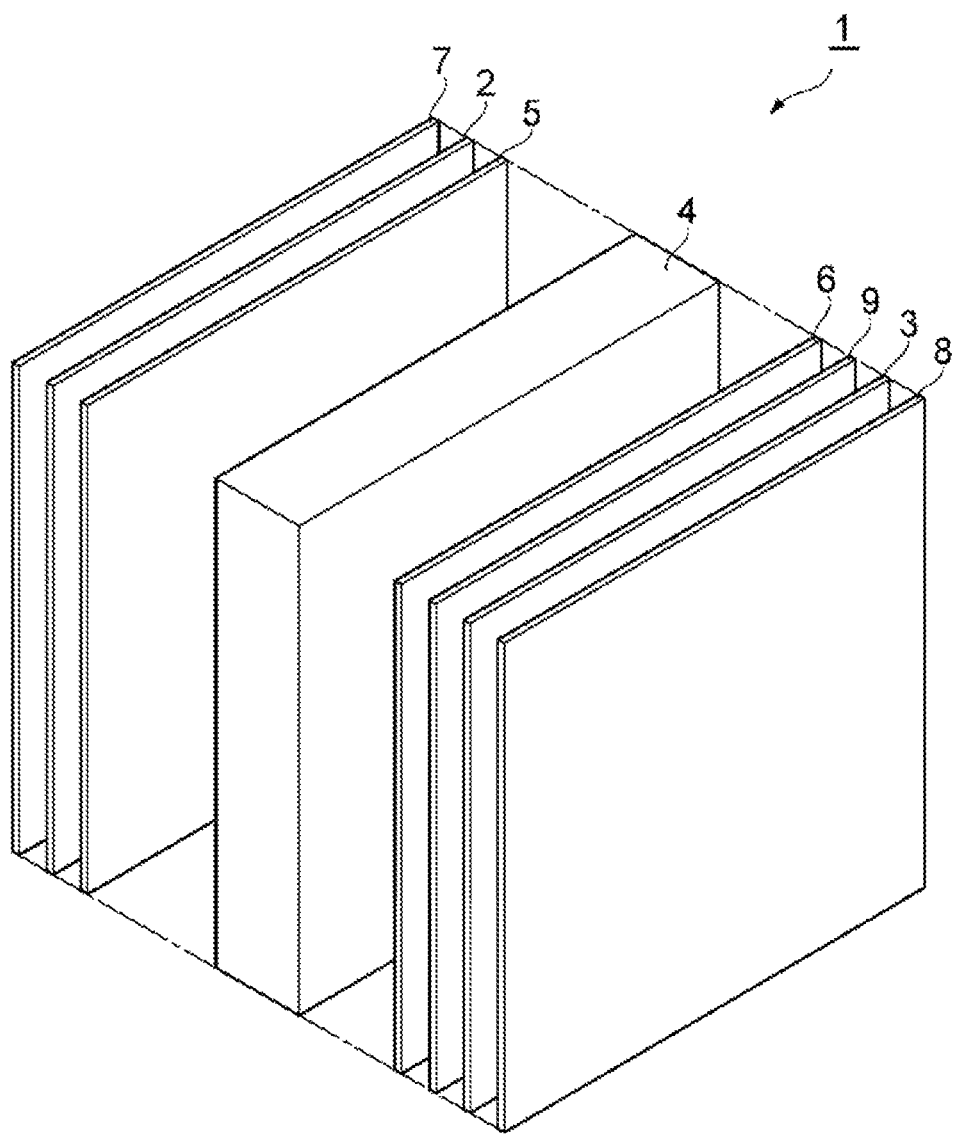

LIQUID CRYSTAL COMPOSITION, LIQUID CRYSTAL DISPLAY ELEMENT AND COMPOUND

CROSS-REFERENCE TO RELATED APPLICATION

This application is a 371 application of the international PCT application serial no. PCT/JP2020/045960, filed on Dec. 10, 2020, which claims the priority benefit of Japan application no. 2020-057865, filed on Mar. 27, 2020. The entirety of each of the above-mentioned patent applications is hereby incorporated by reference herein and made a part of this specification.

TECHNICAL FIELD

The present invention relates to a liquid crystal composition, a liquid crystal display element made with this liquid crystal composition, and a compound.

BACKGROUND ART

Liquid crystal display elements are now used in measuring instruments, automotive panels, word processors, electronic organizers, printers, computers, televisions, ad boards, etc., as well as in timepieces and calculators. Representative examples of liquid crystal display technologies include TN (twisted nematic), STN (super-twisted nematic), and the TFT (thin-film transistor)-based technologies of vertical alignment (VA) and IPS (in-plane switching). Liquid crystal compositions used in such liquid crystal display elements need to be stable against external factors, such as water, air, heat, and light, exhibit a liquid crystal phase over the broadest possible temperature range around room temperature, have little viscosity, and have a low drive voltage at the same time. A liquid crystal composition is composed of a few to tens of compounds so that its parameters like the dielectric anisotropy ($\Delta\varepsilon$) and the refractive-index anisotropy ($\Delta n$) can be optimized for each different liquid crystal display element.

VA displays are made with a liquid crystal composition having a negative $\Delta\varepsilon$ and are used widely in, for example, liquid crystal TVs. In particular, the PSA (polymer-sustained alignment) mode, in which monomers dissolved in the liquid crystal are polymerized to impart the desired pretilt angle to the vertically aligned liquid crystal molecules, is the mainstream of today's TVs because it delivers an expanded viewing angle, quick response, and high transmittance. In recent years, furthermore, researchers have been seeking to further accelerate the response time of liquid crystal display elements and, as a technique for such purposes, making attempts to form the liquid crystal layer using a liquid crystal composition that contains a liquid crystal compound having an alkenyl substructure, such as an alkenyl group (alkenyl liquid crystal compound) (see, for example, PTL 1 and 2).

CITATION LIST

Patent Literature

PTL 1: Japanese Unexamined Patent Application Publication No. 2014-112192
PTL 2: Japanese Unexamined Patent Application Publication No. 2010-285499

SUMMARY OF INVENTION

Technical Problem

Liquid crystal compositions containing an alkenyl liquid crystal compound, however, are disadvantageous in that they are degraded easily by the light emitted from a backlight or the actinic rays of energy, such as ultraviolet radiation, directed thereto during the production of the liquid crystal display element. Impurities resulting from the photodegradation of the liquid crystal composition affect the voltage holding ratio (VHR) of the liquid crystal panel.

The present invention provides a liquid crystal composition, a liquid crystal display element, and a compound with that help achieve a high voltage holding ratio (VHR).

Solution to Problem

After extensive research, the inventors found that a liquid crystal composition that contains a particular compound having polymerizable groups and polar group(s) can be a solution to the above problem. The present invention was completed on the basis of these findings.

That is, the liquid crystal composition according to the present invention is:

characterized in that it contains one compound A, represented by general formula (Y) below, or two or more compounds A

[Chem. 1]

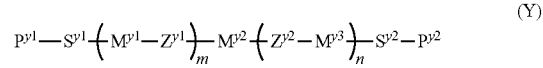
(Y)

(In general formula (Y), $S^{y1}$ and $S^{y2}$ each independently represent a single bond or a linear or branched C1 to C12 alkylene group, optionally with a hydrogen atom or hydrogen atoms in the alkylene group substituted by a halogen atom, a cyano group, or a nitro group, optionally with a —$CH_2$— or —$CH_2$-s in the alkylene group substituted with —CH=CH—, —C≡C—, —CO—, —COO—, —OCO—, —OCOO—, —O—, —NH—, or —S—, although without two or more —O-s consecutively next to each other, $M^{y1}$, $M^{y2}$, and $M^{y3}$ each independently represent a divalent aromatic group, a divalent alicyclic group, a divalent heterocyclic compound group, a divalent fused-ring system, or a divalent fused-polycyclic system, optionally with a hydrogen atom or hydrogen atoms in the ring structure substituted with $L^{y1}$, $L^{y1}$ represents $P^{y3}$—$S^{y3}$—, a halogen atom, a cyano group, a nitro group, or a linear or branched C1 to C30 alkyl group, optionally with a hydrogen atom or hydrogen atoms in the alkyl group substituted by a halogen atom, a cyano group, or a nitro group, optionally with a —$CH_2$— or —$CH_2$-s in the alkyl group substituted with —CH=CH—, —C≡C—, —CO—, —COO—, —OCO—, —OCOO—, —O—, —NH—, or —S—, although without two or more —O-s consecutively next to each other, and if there are multiple $L^{y1}$s, the $L^{y1}$s may be the same or different, $P^{y1}$, $P^{y2}$, and $P^{y3}$ represent polymerizable groups, $S^{y3}$ represents a single bond or a linear or branched C1 to C12 alkylene group, optionally with a hydrogen atom or hydrogen atoms in the alkylene group substituted by a halogen atom, a cyano group, or a nitro group, optionally with a —$CH_2$— or —$CH_2$-s in the alkylene group substituted with —CH=CH—, —C≡C—, —CO—, —COO—, —OCO—, —OCOO—, —O—, —NH—, or —S—, although without two or more —O-s consecutively next to each other, $Z^{y1}$ and $Z^{y2}$ each independently represent a single bond, —$C_2H_4$—, —$C_4H_8$—, —$C_3H_6$—, —$OCH_2$—, —$CH_2O$—, —CO—, —COO—, —OCO—, —$OCOOCH_2$—, —$CH_2OCOO$—, —$OCH_2CH_2O$—, —CH=CRa—COO—, —CH=CRa—OCO—, —COO—CRa=CH—, —OCO—CRa=CH—, —COO—CRa=CH—COO—, —COO—CRa=CH—OCO—, —OCO—CRa=CH—COO—, —OCO—CRa=CH—OCO—, —$COOC_2H_4$—, —$OCOC_2H_4$—, —$C_2H_4OCO$—, —$CH_2OCO$—, —$COOCH_2$—, —$OCOCH_2$—, —CH=CH—, —CF=CF—, —CF=CH—, —CH=CF—, —$CF_2O$—, —$OCF_2$—, —$CF_2CH_2$—, —$CH_2CF_2$—, —$CF_2CF_2$—, or —C≡C— (In the formulae, Ra at each occurrence independently represents a hydrogen atom or a $C_1$ to $C_4$ alkyl group.), m and n each independently represent an integer of 0 to 4, with the proviso that m+n is 0 to 6, and if $S^{y1}$, $S^{y2}$, or $L^{y1}$ is a $C_1$ to $C_{12}$ alkylene or alkyl group, one or more —$CH_2$-s therein are substituted with a substructure represented by general formula (A-1) below

[Chem. 2]

$$—S^{y4}—K^{i1}—S^{y5}— \quad (A-1)$$

(In general formula (A-1), $S^{y4}$ and $S^{y5}$ each independently represent a single bond or a C1 to C12 linear or branched alkylene group, optionally with a hydrogen atom or hydrogen atoms in the alkylene group substituted by a halogen atom, a cyano group, or a nitro group, optionally with a —$CH_2$— or —$CH_2$-s in the alkylene group substituted with —CH=CH—, —C≡C—, —CO—, —COO—, —OCO—, —OCOO—, —O—, —NH—, or —S—, although without two or more —O-s consecutively next to each other, and $K^{i1}$ at each occurrence independently represents a group represented by general formula (K-1) or (K-2) below

[Chem. 3]

$$\left( Sp^{i3}—P^{i2} \right)_{ki1}$$
$$\left( Sp^{i4}—T^{k1} \right)_{ki2} \quad (K-1)$$
$$\left( R^{k1} \right)_{ki3}$$

$$—T^{k2} \quad (K-2)$$

(In general formula (K-1), $Sp^{i3}$ and $Sp^{i4}$ each independently represent a single bond, a linear or branched C1 to C20 alkylene group, or a linear or branched C1 to C20 halogenated alkylene group, optionally with a —$CH_2$— or —$CH_2$-s in the alkylene or halogenated alkylene group substituted with —CH=CH—, —C≡C—, or —O— without two —O-s consecutively next to each other, $P^{i2}$ represents a polymerizable group, $R^{k1}$ at each occurrence independently represents a hydrogen atom or a linear or branched C1 to C6 alkyl group, optionally with one —$CH_2$— in the alkyl group, or nonadjacent two or more —$CH_2$-s in the alkyl group, substituted with —O—, ki1 and ki3 each independently represent 0 or 1, and ki2 represents 1 or 2, with the proviso that ki1+ki2+ki3 is 2, and $T^{k1}$ at each occurrence independently represents a group represented by any of general formulae (T-1) to (T-10)

[Chem. 4]

●—OH (T-1)

●—COOH (T-2)

●—$S^{T1}$—C—$R^{T1}$ (T-3)
        ‖
        O

●—SH (T-4)

●—C≡N (T-5)

●—N$\diagdown^{R^{T2}}_{R^{T3}}$ (T-6)

●—$S^{T1}$—O—C(=O)—C(=$CH_2$)—$CH_2$—OH (T-7)

(T-8) cyclohexane ring with $X^{K1}$, $Y^{K1}$, =$Z^{K1}$, $R^{T4}$ (T-9) cyclohexane ring with $X^{K1}$, $Y^{K1}$, =$Z^{K1}$, $R^{T4}$ (T-10) cyclohexane ring with $Z^{K1}$, $R^{T4}$ (in general formulae (T-1) to (T-10), $S^{T1}$ at each occurrence independently represents a single bond, a linear or branched C1 to C15 alkylene group, or a linear or branched C2 to C18 alkenylene group, optionally with a —$CH_2$— or —$CH_2$-s in the alkylene or alkenylene group substituted by —O—, —COO—, —C(=O)—, or —OCO— unless oxygen atoms come consecutively next to each other, $R^{T1}$ at each occurrence independently represents a C1 to C5 alkyl group, optionally with a —$CH_2$— or —$CH_2$-s in the alkyl group substituted by —O—, —COO—, —C(=O)—, or —OCO— in such a manner that oxygen atoms are not consecutively next to each other, and $R^{T2}$, $R^{T3}$, and $R^{T4}$ each independently represent a hydrogen atom or a $C_1$ to $C_{12}$ alkyl group, optionally with a —$CH_2$— or —$CH_2$-s in the alkyl group substituted by —O—, —COO—, —C(=O)—, or —OCO— unless oxygen atoms come consecutively next to each other), and in general formula (K-2), $T^{k2}$ at each occurrence independently represents a group represented by any of general formulae (T-11) to (T-13)

[Chem. 5]

(T-11) cyclohexane ring with $X^{K1}$, $Y^{K1}$, =$Z^{K1}$ (T-12)
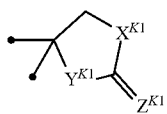

(T-13)
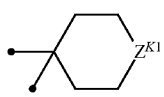

(In general formulae (T-11) to (T-13), $X^{K1}$ and $Y^{K1}$ each independently represent —CH$_2$—, an oxygen atom, or a sulfur atom, and $Z^{K1}$ at each occurrence independently represents an oxygen atom or a sulfur atom.). The black dots in the formulae represent bonds.).), or one or more hydrogen atoms in $S^{y1}$, $S^{y2}$, $M^{y1}$, $M^{y2}$, $M^{y3}$, or $L^{y1}$ are substituted with a substructure represented by general formula (A-2) below

[Chem. 6]

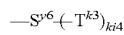 (A-2)

(In general formula (A-2), $S^{y6}$ represents a single bond or a linear or branched C1 to C12 alkylene group, optionally with a hydrogen atom or hydrogen atoms in the alkylene group substituted by a halogen atom, a cyano group, or a nitro group, optionally with a —CH$_2$— or —CH$_2$-s in the alkylene group substituted with —CH=CH—, —C≡C—, —CO—, —COO—, —OCO—, —OCOO—, —O—, —NH—, or —S—, although without two or more —O-s consecutively next to each other, $T^{k3}$ represents a group represented by any of general formulae (T-1) to (T-13) and (T-14) to (T-24)

[Chem. 7]

(T-14)
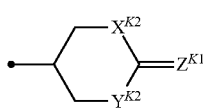

(T-15)
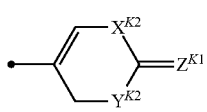

(T-16)
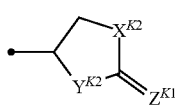

(T-17)
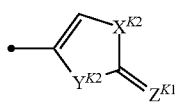

(T-18)
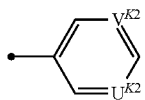

(T-19)
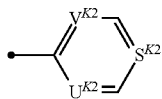

(T-20)
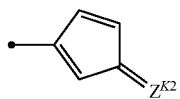

(T-21)
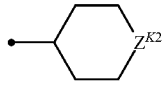

(T-22)
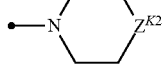

(T-23)
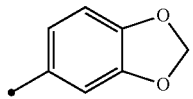

(T-24)
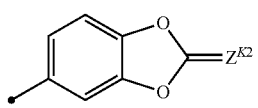

(In general formulae (T-14) to (T-24), $X^{K2}$ expresses the same as the definition of $X^{K1}$, $Y^{K2}$ expresses the same as the definition of $Y^{K1}$, $Z^{K2}$ expresses the same as the definition of $Z^{K1}$, and $U^{K2}$, $V^{K2}$, and $S^{K2}$ each independently represent a methine group or a nitrogen atom.

The black dot in the formulae represents a bond.), and ki4 is 1 to 3.).).

A liquid crystal display element according to the present invention is characterized in that it is made with the above liquid crystal composition.

A compound according to the present invention is characterized in that it is a compound represented by general formula (Y) above.

Advantageous Effects of Invention

The liquid crystal composition according to the present invention helps achieve a high voltage holding ratio (VHR) by virtue of containing compound(s) A, represented by general formula (Y) above.

BRIEF DESCRIPTION OF DRAWINGS

The FIGURE is an exploded perspective diagram illustrating an example of a liquid crystal display element made with the liquid crystal composition according to the present invention.

DESCRIPTION OF EMBODIMENTS

1. Liquid Crystal Composition

The inventors found that the presence of compound A, represented by general formula (Y) below, in a liquid crystal composition helps achieve a high voltage holding ratio (VHR). To be more specific, the compound represented by general formula (Y) below helps prevent the liquid crystal composition from losing its voltage holding ratio because of impurities formed during its use, such as those resulting from photodegradation of an alkenyl compound, because polar group(s) in compound A captures such impurities. The release of the captured impurities back into the liquid crystal composition, furthermore, is limited because when compound A polymerizes (forms a polymer), the impurities are taken into the polymer and immobilized there. This prevents the impurities from dispersing throughout the liquid crystal composition, helping isolate the liquid crystal molecules from the impurities. As a result, the specific resistance and the voltage holding ratio of the liquid crystal composition are kept high. A liquid crystal display element made with the liquid crystal composition according to the present invention, therefore, can be highly reliable.

1-1. Compound(s) A, Represented by General Formula (Y)

A liquid crystal composition according to the present invention is characterized in that it contains one compound A, represented by general formula (Y) below, or two or more compounds A.

[Chem. 8]

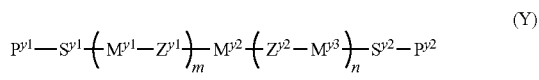
(Y)

In general formula (Y), $S^{y1}$ and $S^{y2}$ each independently represent a single bond or a linear or branched C1 to C12 alkylene group. Hydrogen atom(s) in the alkylene group may be substituted by a halogen atom, a cyano group, or a nitro group. —CH$_2$— (s) in the alkylene group may be substituted with —CH=CH—, —C≡C—, —CO—, —COO—, —OCO—, —OCOO—, —O—, —NH—, or —S—, although without two or more —O-s consecutively next to each other. More preferably, at least one of $S^{y1}$ or $S^{y2}$ is a single bond because this further improves the voltage holding ratio, encourages the formation of a pretilt angle, and is expected to improve the stability of the pretilt angle under stress conditions at the same time.

$M^{y1}$, $M^{y2}$, and $M^{y3}$ each independently represent a divalent aromatic group, a divalent alicyclic group, a divalent heterocyclic compound group, a divalent fused-ring system, or a divalent fused-polycyclic system, optionally with hydrogen atom(s) in the ring structure substituted with $L^{y1}$.

More specifically, $M^{y1}$, $M^{y2}$, and $M^{y3}$ each independently represent a group selected from the group consisting of formulae (V-1) to (V-21) below, optionally with the group substituted with $L^{y1}$.

[Chem. 9]

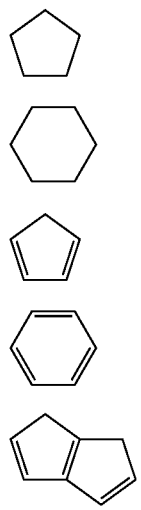

(V-1)

(V-2)

(V-3)

(V-4)

(V-5)

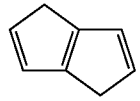
(V-6)

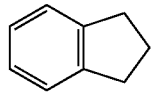
(V-7)

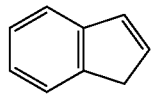
(V-8)

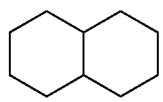
(V-9)

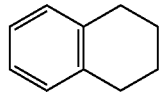
(V-10)

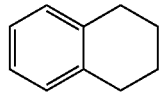
(V-11)

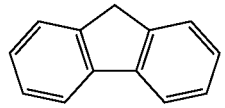
(V-12)

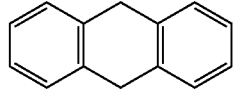
(V-13)

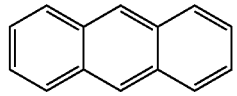
(V-14)

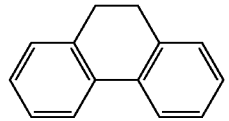
(V-15)

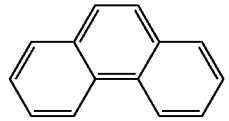
(V-16)

(V-17)

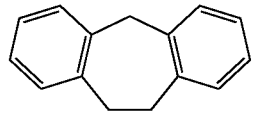
(V-18)

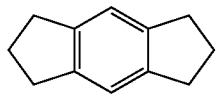 (V-19)

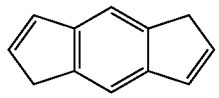 (V-20)

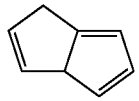 (V-21)

In formulae (V-1) to (V-21), the group may have a bond at any position, optionally with any —CH= at each occurrence independently replaced by —N=, optionally with —CH$_2$— at each occurrence independently replaced by —O—, —S—, —NR$^0$— (In the formula, R$^0$ represents a hydrogen atom or a C$_1$ to C$_{20}$ alkyl group.), —CS—, or —CO—, although no —O—O— linkage is included.

If solubility in the liquid crystal composition is a priority, (V-1), (V-2), (V-3), (V-4), and (V-7) are preferred. If high reactivity is a priority, (V-4), (V-11), (V-16), and (V-20) are preferred. If good formation of a pretilt angle is a priority, (V-2), (V-4), (V-7), (V-8), (V-10), and (V-11) are preferred. If effectiveness in improving the VHR is a priority, (V-2), (V-4), and (V-11) are preferred. If the balance between these is a priority, (V-2), (V-4), (V-10), and (V-11) are preferred.

Because of the availability of raw materials and the ease of synthesis, it is particularly preferred that M$^{y2}$ be a group represented by formula (V-4-1) or (V-4-2) below. In the formulae, the bonds each connect to any of S$^{y3}$, Z$^{y1}$, or Z$^{y2}$.

[Chem. 10]

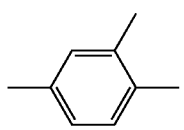 (V-4-1)

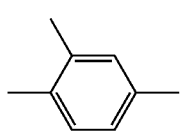 (V-4-2)

Because of the availability of raw materials and the ease of synthesis, furthermore, M$^{y1}$ and M$^{y3}$ may each independently be unsubstituted or substituted by one or more L$^{y1}$s. Preferably, M$^{y1}$ and M$^{y3}$ represent 1,4-phenylene groups, 1,4-cyclohexylene groups, or naphthalene-2,6-diyl, more preferably a group selected from formulae (W-1) to (W-11) below each independently, even more preferably a group selected from formulae (W-1) to (W-8) each independently. It is particularly preferred that M$^{y1}$ and M$^{y3}$ each independently represent a group selected from formulae (W-1) to (W-4).

[Chem. 11]

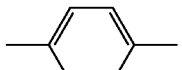 (W-1)

 (W-2)

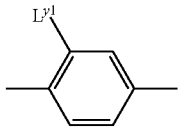 (W-3)

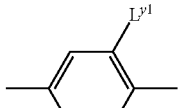 (W-4)

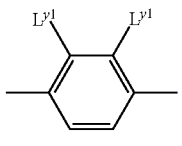 (W-5)

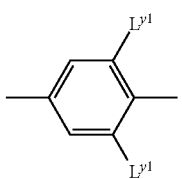 (W-6)

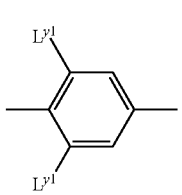 (W-7)

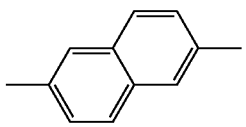 (W-8)

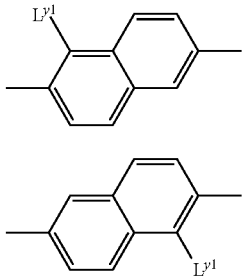 (W-9)

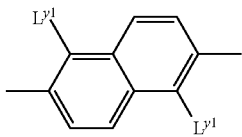 (W-10)

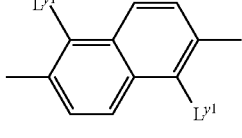 (W-11)

In general formula (Y), L$^{y1}$ represents P$^{y3}$—S$^{y3}$—, a halogen atom, a cyano group, a nitro group, or a linear or branched C1 to C30 alkyl group. Hydrogen atom(s) in the alkyl group may be substituted by a halogen atom, a cyano group, or a nitro group. —CH$_2$-(s) in the alkyl group may be substituted with —CH=CH—, —C≡C—, —CO—, —COO—, —OCO—, —OCOO—, —O—, —NH—, or —S—, although without two or more —O-s consecutively next to each other. If there are multiple L$^{y1}$s, the L$^{y1}$s may be the same or different. More preferably, L$^{y1}$ represents P$^{y3}$—S$^{y3}$—, a fluorine atom, a chlorine atom, a cyano group, or a linear or branched C$_1$ to C$_{12}$ alkyl group, optionally with hydrogen atom(s) in the alkyl group substituted by a fluorine atom, a chlorine atom, or a cyano group, optionally with —CH$_2$-(s) in the alkyl group substituted with —CH=CH—, —COO—, —OCO—, —O—, or —S—, although without two or more —O-s consecutively next to each other. Even more preferably, L$^{y1}$ represents P$^{y3}$—S$^{y3}$—, a fluorine atom, a chlorine atom, or a linear or branched C$_1$ to C$_6$ alkyl group, optionally with hydrogen atom(s) in the alkyl group substituted by a fluorine or chlorine atom, optionally with —CH$_2$-(s) in the alkyl group substituted with —CH=CH—, —COO—, —OCO—, or —O—, although without two or more —O-s consecutively next to each other.

In general formula (Y), P$^{y1}$, P$^{y2}$, and P$^{y3}$ represent polymerizable groups. A polymerizable group has the function of forming a polymer locally at interfaces in the liquid crystal display element in response to heat, light, or any other external stimulus. P$^{y1}$, P$^{y2}$, and P$^{y3}$ can each independently be, for example, a group represented by any of formulae (YP-1) to (YP-16) below. In the formulae, the black dot represents a bond. By virtue of their ease of handling and reactivity, the groups represented by formulae (YP-1) to (YP-3), (YP-14), and (YP-15) are preferred, and (YP-1) and (YP-2) are more preferred.

[Chem. 12]

(YP-1)

(YP-2)

(YP-3)

(YP-4)

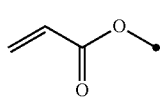

(YP-5)

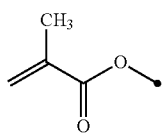

(YP-6)

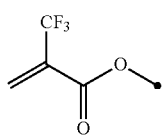

(YP-7)

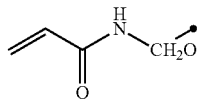

(YP-8)

(YP-9)

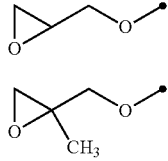

(YP-10)

(YP-11)

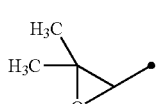

(YP-12)

(YP-13)

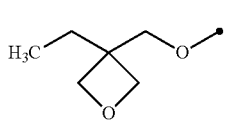

(YP-14)

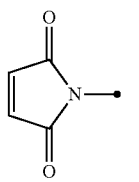

(YP-15)

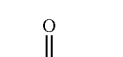

(YP-16)

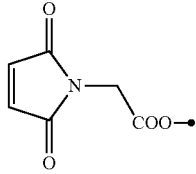

In general formula (Y), S$^{y3}$ represents a single bond or a linear or branched C1 to C12 alkylene group. Hydrogen atom(s) in the alkylene group may be substituted by a halogen atom, a cyano group, or a nitro group. —CH$_2$-(s) in the alkylene group may be substituted with —CH=CH—, —C≡C—, —CO—, —COO—, —OCO—, —OCOO—, —O—, —NH—, or —S—, although without two or more —O-s consecutively next to each other.

In general formula (Y), Z$^{y1}$ and Z$^{y2}$ each independently represent a single bond, —C$_2$H$_4$—, —C$_4$H$_8$—, —C$_3$H$_6$—, —OCH$_2$—, —CH$_2$O—, —CO—, —COO—, —OCO—, —OCOOCH$_2$—, —CH$_2$OCOO—, —OCH$_2$CH$_2$O—, —CH=CRa—COO—, —CH=CRa—OCO—, —COO—CRa=CH—, —OCO—CRa=CH—, —COO—CRa=CH—COO—, —COO—CRa=CH—OCO—, —OCO—CRa=CH—COO—, —OCO—CRa=CH—

OCO—, —COOC$_2$H$_4$—, —OCOC$_2$H$_4$—, —C$_2$H$_4$OCO—, —CH$_2$OCO—, —COOCH$_2$—, —OCOCH$_2$—, —CH=CH—, —CF=CF—, —CF=CH—, —CH=CF—, —CF$_2$O—, —OCF$_2$—, —CF$_2$CH$_2$—, —CH$_2$CF$_2$—, —CF$_2$CF$_2$—, or —C≡C—. Ra at each occurrence independently represents a hydrogen atom or a C1 to C4 alkyl group.

In general formula (Y), m and n each independently represent an integer of 0 to 4, more preferably an integer of 0 to 3, even more preferably an integer of 0 to 2. Preferably, the total, m+n, is 0 to 6. If the total m+n is large, it is expected that concern about the volatilization of the liquid crystal composition during its vacuum injection will be alleviated, and that a larger pretilt angle will be imparted. If the total m+n is small, however, solubility in the liquid crystal composition can be low. For these reasons, it is more preferred that the total m+n be 1 or 2, even more preferably 1. It is particularly preferred that the total m+n be 1 with at least one of S$^{y1}$ or S$^{y2}$, in general formula (Y), being a single bond.

In general formula (Y) above, furthermore,
if S$^{y1}$, S$^{y2}$, or L$^{y1}$ is a C1 to C12 alkylene or alkyl group, one or more —CH$_2$-s therein are substituted with a substructure represented by general formula (A-1) below, or one or more hydrogen atoms in S$^{y1}$, S$^{y2}$, M$^{y1}$, M$^{y2}$, M$^{y3}$, or L$^{y1}$ are substituted with a substructure represented by general formula (A-2), which is given later herein.

[Chem. 13]

(A-1)

The following describes a substructure represented by general formula (A-1) first. In general formula (A-1), S$^{y4}$ and S$^{y5}$ each independently represent a single bond or a C1 to C12 linear or branched alkylene group. Hydrogen atom(s) in the alkylene group may be substituted by a halogen atom, a cyano group, or a nitro group. —CH$_2$-(s) in the alkylene group may be substituted with —CH=CH—, —C≡C—, —CO—, —COO—, —OCO—, —OCOO—, —O—, —NH—, or —S—, although without two or more —O-s consecutively next to each other.

K$^{i1}$ at each occurrence independently represents a group represented by general formula (K-1) or (K-2) below. The black dots in the formulae represent bonds.

[Chem. 14]

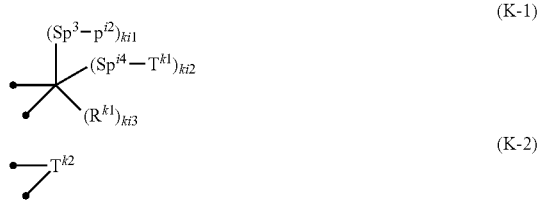

In general formula (K-1), Sp$^{i3}$ and Sp$^{i4}$ each independently represent a single bond, a linear or branched C1 to C20 alkylene group, or a linear or branched C1 to C20 halogenated alkylene group. —CH$_2$-(s) in the alkylene or halogenated alkylene group may be substituted with —CH=CH—, —C≡C—, or —O— without two —O-s consecutively next to each other.

P$^{i2}$ represents a polymerizable group. The definition of P$^{i2}$ is the same as that of the polymerizable groups represented by P$^{y1}$, P$^{y2}$, and P$^{y3}$ stated above.

R$^{k1}$ at each occurrence independently represents a hydrogen atom or a linear or branched C1 to C6 alkyl group, optionally with one —CH$_2$— in the alkyl group, or nonadjacent two or more —CH$_2$-s in the alkyl group, substituted with —O—.

ki1 and ki3 each independently represent 0 or 1, and ki2 represents 1 or 2, with the proviso that ki1+ki2+ki3 is 2.

T$^{k1}$ at each occurrence independently represents a group represented by any of general formulae (T-1) to (T-10).

[Chem. 15]

(T-1)

(T-2)

(T-3)

(T-4)

(T-5)

(T-6)

(T-7)

(T-8)

(T-8)

(T-9)

(T-10)

In general formulae (T-1) to (T-10), S$^{T1}$ at each occurrence independently represents a single bond, a linear or branched C1 to C15 alkylene group, or a linear or branched C2 to C18 alkenylene group. —CH$_2$-(s) in the alkylene or alkenylene group may be substituted by —O—, —COO—, —C(=O)—, or —OCO— in such a manner that oxygen atoms are not consecutively next to each other.

R$^{T1}$ at each occurrence independently represents a C1 to C5 alkyl group, optionally with —CH$_2$-(s) in the alkyl group substituted by —O—, —COO—, —C(=O)—, or —OCO— in such a manner that oxygen atoms are not consecutively next to each other.

R$^{T2}$, R$^{T3}$, and R$^{T4}$ each independently represent a hydrogen atom or a C1 to C12, more preferably C1 to C5, alkyl group.

In general formula (K-2), T$^{k2}$ at each occurrence independently represents a group represented by any of general formulae (T-11) to (T-13). The black dots in the formulae represent bonds.

[Chem. 16]

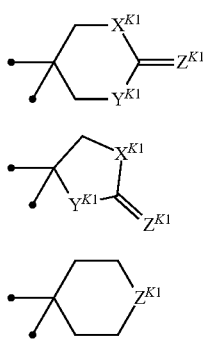
(T-11)

(T-12)

(T-13)

In general formulae (T-11) to (T-13), $X^{K1}$ and $Y^{K1}$ each independently represent —$CH_2$—, an oxygen atom, or a sulfur atom.

$Z^{K1}$ at each occurrence independently represents an oxygen atom or a sulfur atom.

The following describes a substructure represented by general formula (A-2) below.

[Chem. 17]

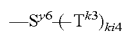
(A-2)

In general formula (A-2), $S^{y6}$ represents a single bond or a linear or branched C1 to C12 alkylene group. Hydrogen atom(s) in the alkylene group may be substituted by a halogen atom, a cyano group, or a nitro group. —$CH_2$-(s) in the alkylene group may be substituted with —CH=CH—, —C≡C—, —CO—, —COO—, —OCO—, —OCOO—, —O—, —NH—, or —S—, although without two or more —O-s consecutively next to each other.

$T^{k3}$ represents a group represented by any of general formulae (T-1) to (T-13) and (T-14) to (T-24), and $k^{i4}$ is 1 to 3. The black dot in the formulae represents a bond.

[Chem. 18]

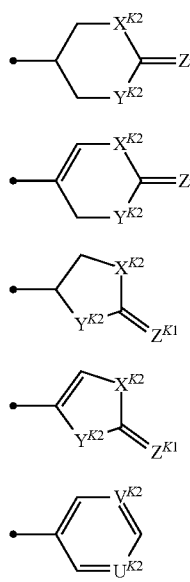
(T-14)

(T-15)

(T-16)

(T-17)

(T-18)

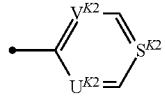
(T-19)

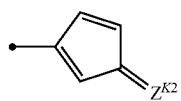
(T-20)

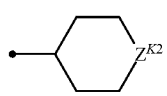
(T-21)

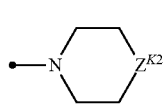
(T-22)

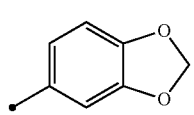
(T-23)

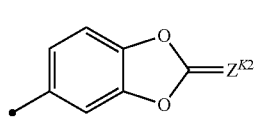
(T-24)

In general formulae (T-14) to (T-24), $X^{K2}$ expresses the same as the definition of $X^{K1}$. $Y^{K2}$ expresses the same as the definition of $Y^{K1}$. $Z^{K2}$ expresses the same as the definition of $Z^{K1}$. $U^{K2}$, $V^{K2}$, and $S^{K2}$ each independently represent a methine group or a nitrogen atom.

Preferably, compound(s) A, represented by general formula (Y), is compound(s) having one —$CH_2$— in $S^{y1}$, $S^{y2}$, or $L^{y1}$ substituted with a group represented by a substructure represented by formula (w-1) or (w-2) below, for example because such compounds are highly soluble and have a high voltage holding ratio (VHR). In the formulae, the black dots represent bonds, and Me represents a methyl group.

[Chem. 19]

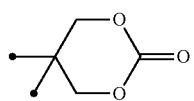
(w-1)

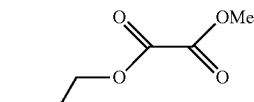
(w-2)

Specific examples of compounds A, represented by general formula (Y), include the compounds represented by formulae (x-1) to (x-31), (y-1) to (y-25), and (z-1) to (z-6) below.

[Chem. 20]
(x-1) (y-1)
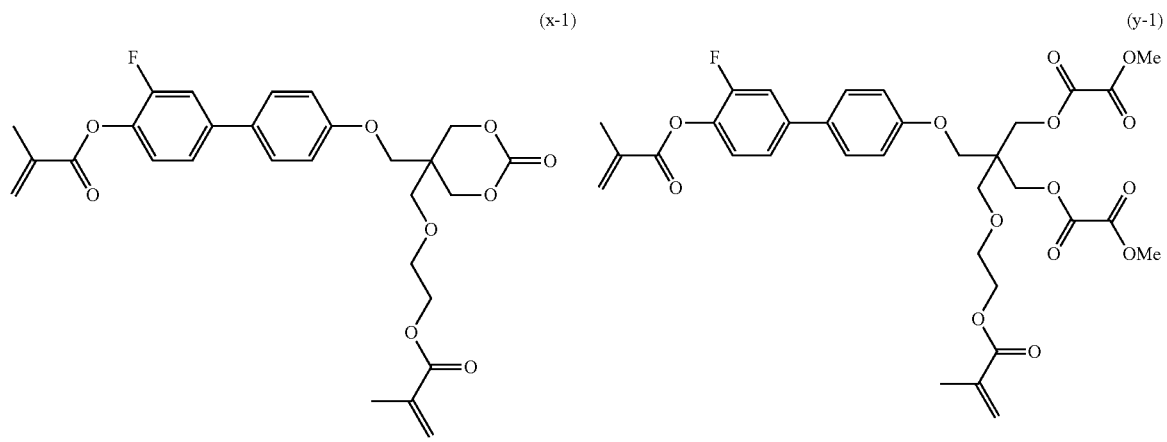
(x-2) (y-2)
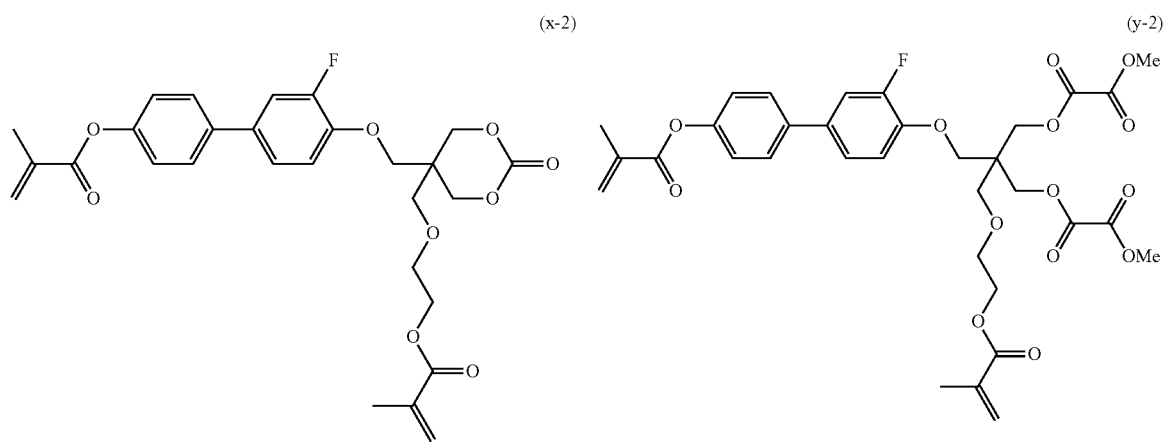
(x-3) (y-3)
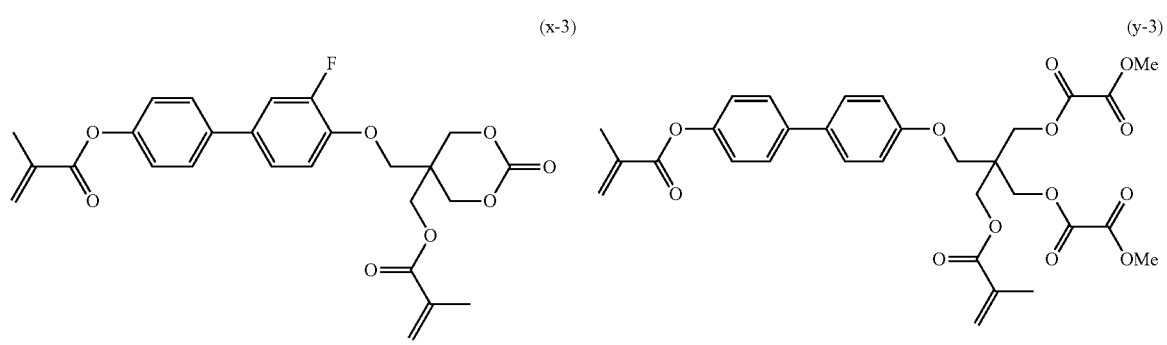
[Chem. 21]
(x-4) (y-4)
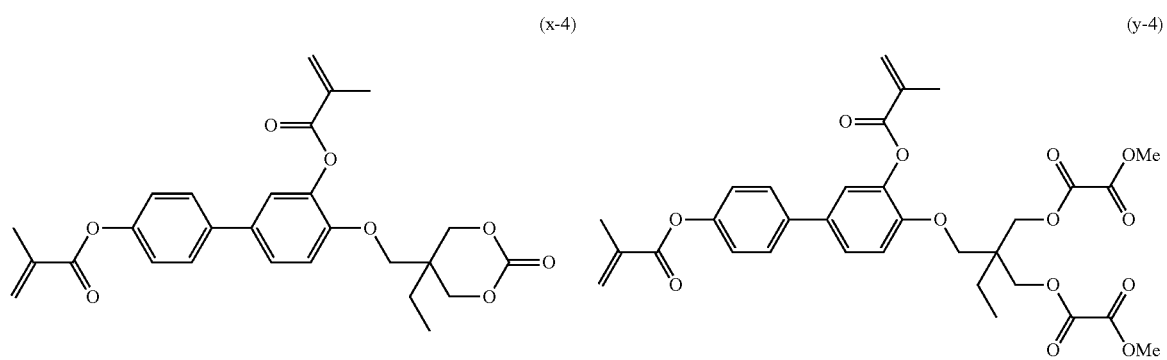

-continued
(x-5)    (y-5)
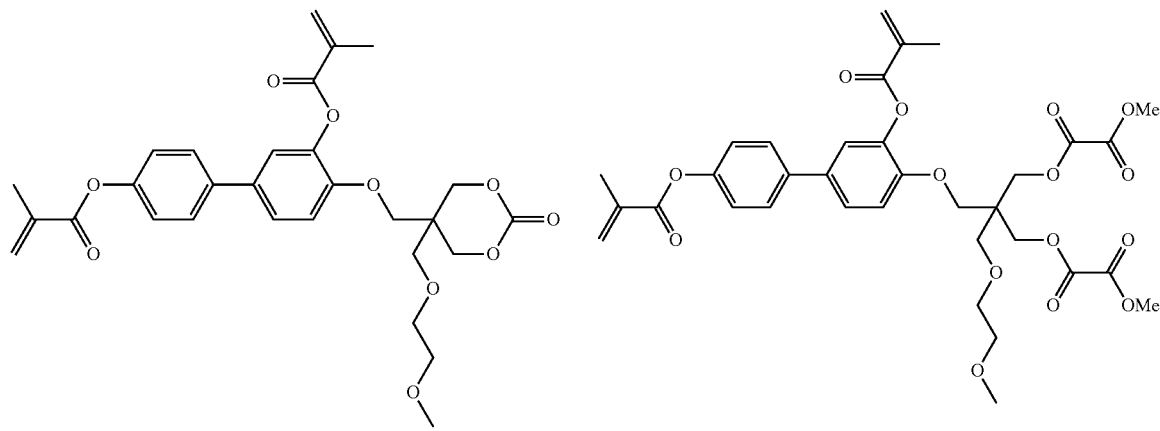
(x-6)    (y-6)
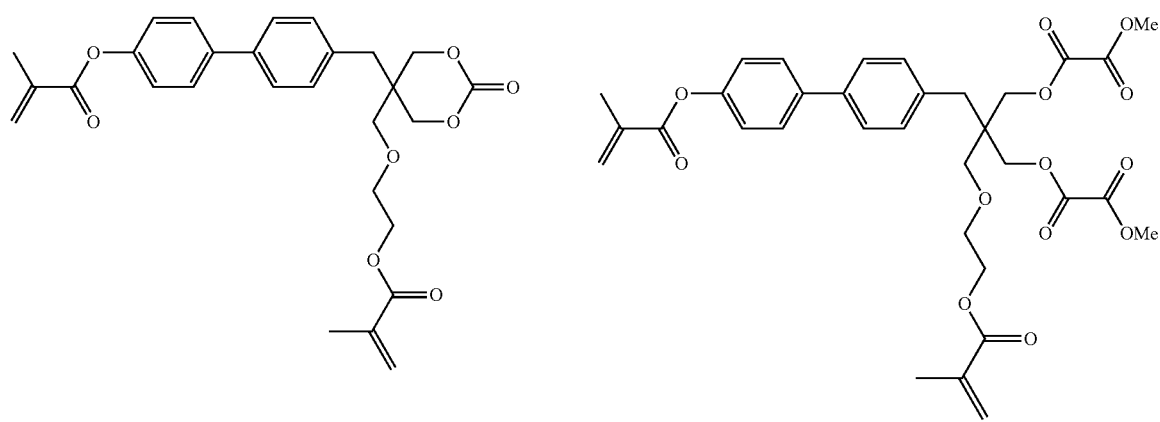
[Chem. 22]
(x-7)    (y-7)
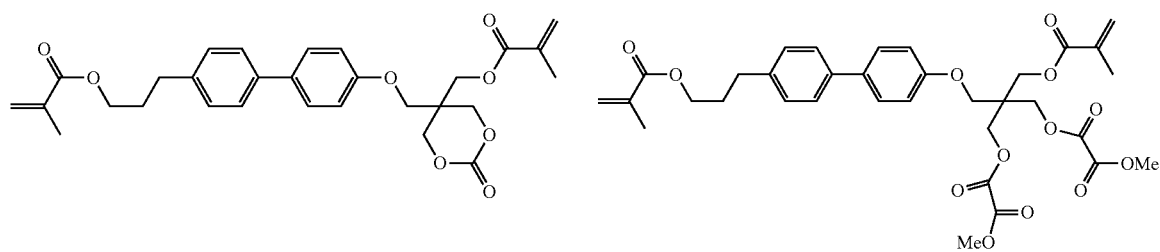
(x-8)    (y-8)
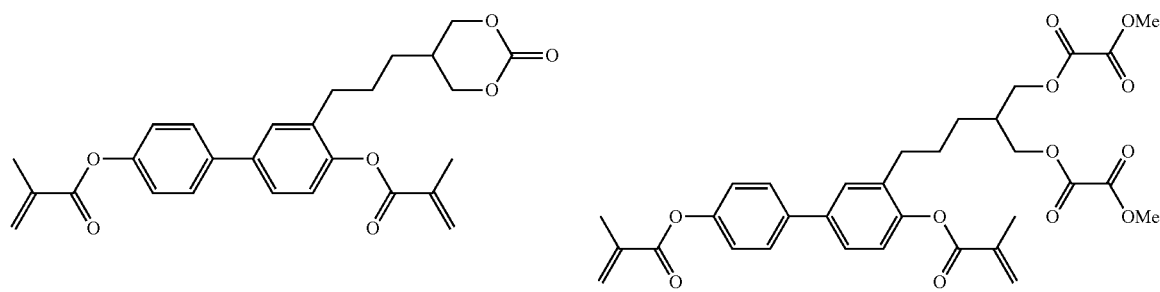

-continued
(x-9)
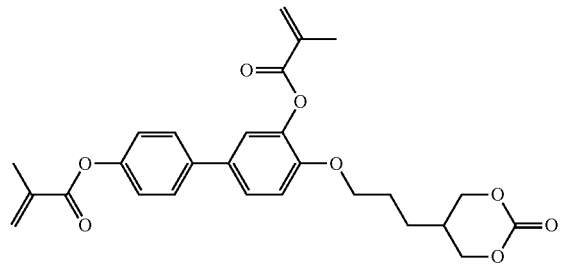
(y-9)
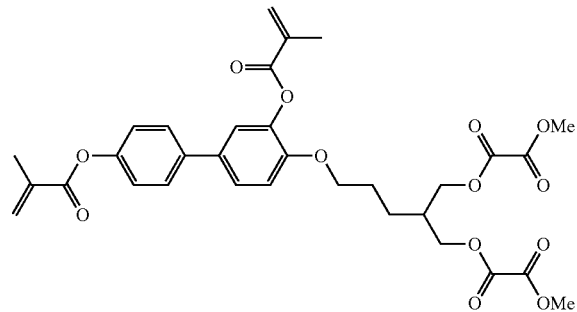
[Chem. 23]
(x-10)
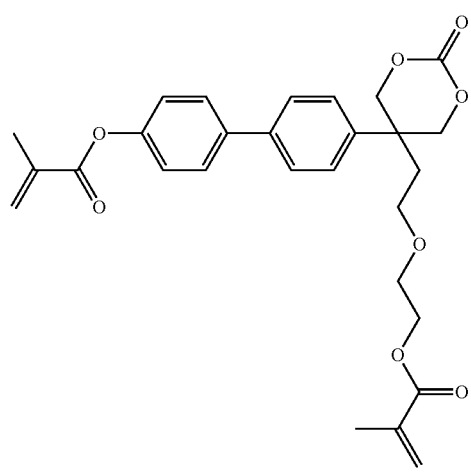
(y-10)
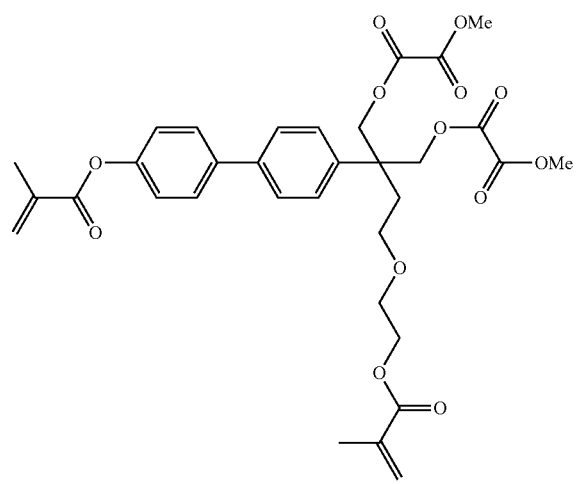
(x-11)
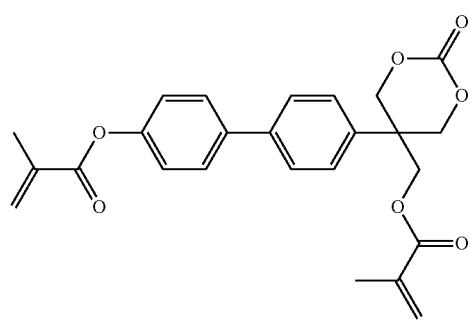
(y-11)
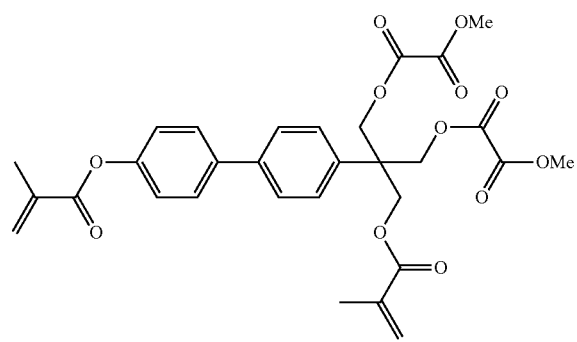
(x-12)
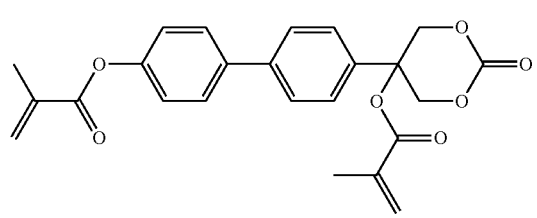
(y-12)
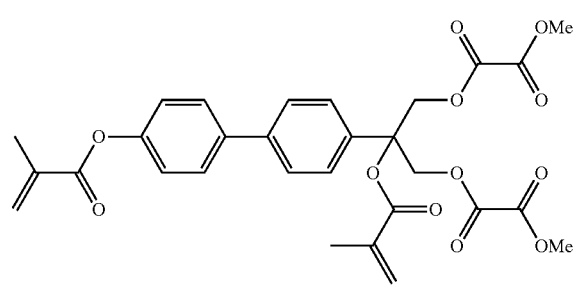

-continued
[Chem. 24]
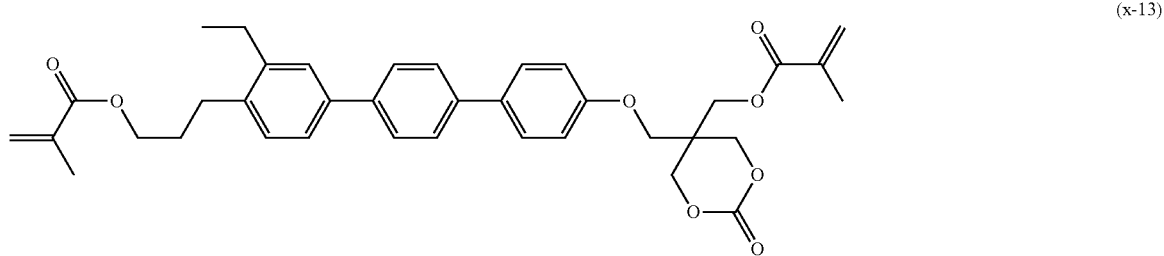
(x-13)
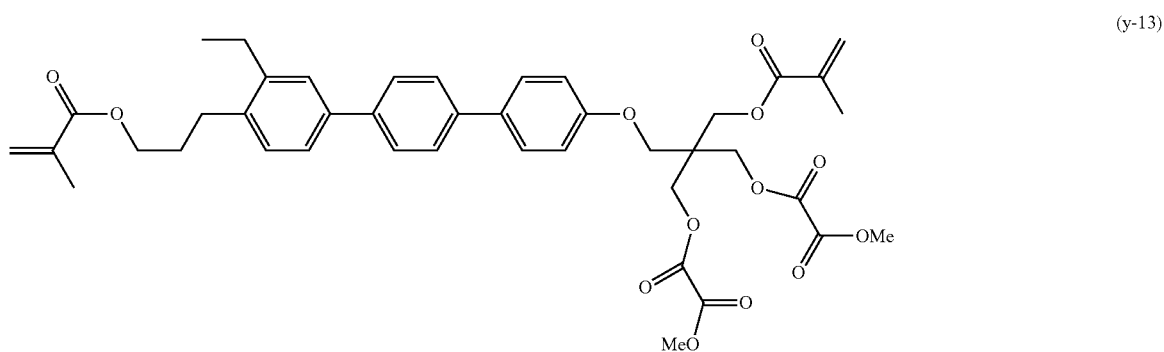
(y-13)
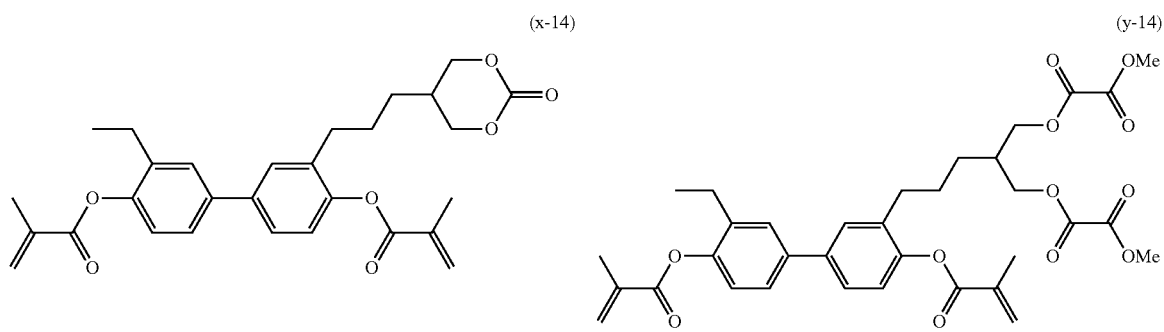
(x-14)
(y-14)
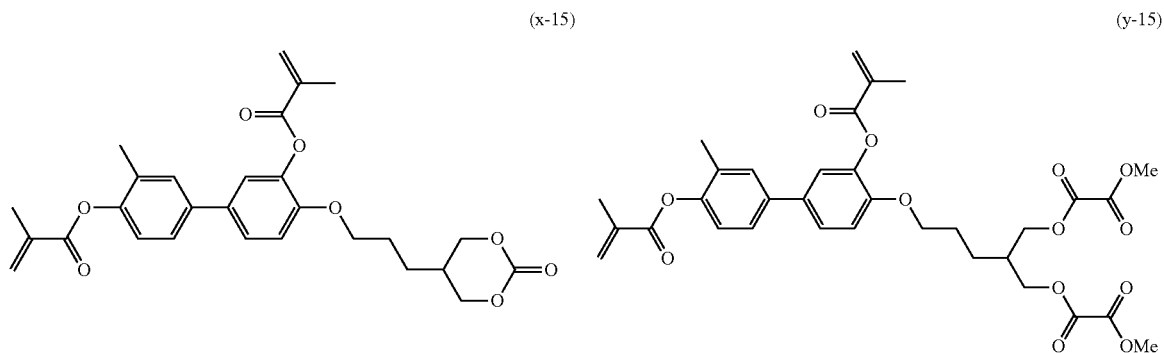
(x-15)
(y-15)

-continued
[Chem. 25]
(x-16)
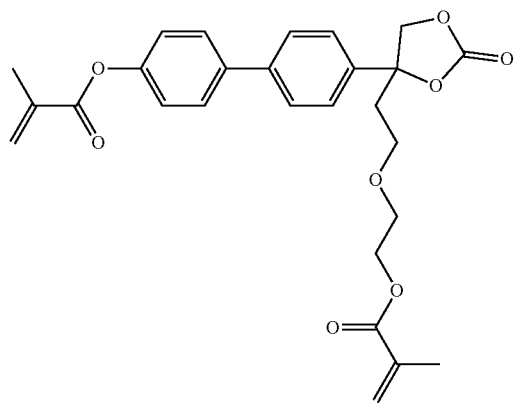
(y-16)
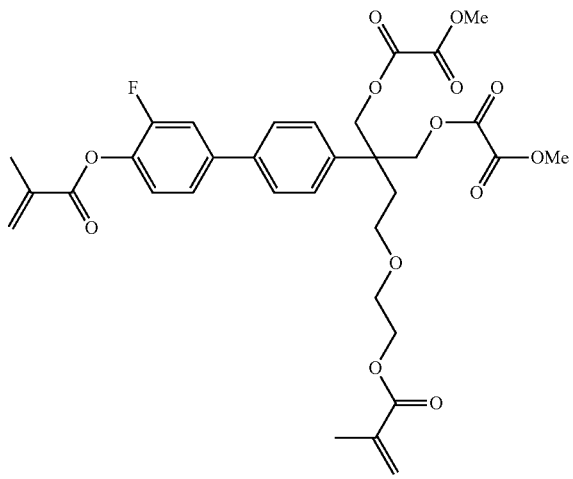
(x-17)
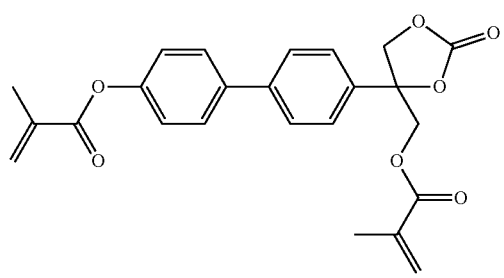
(y-17)
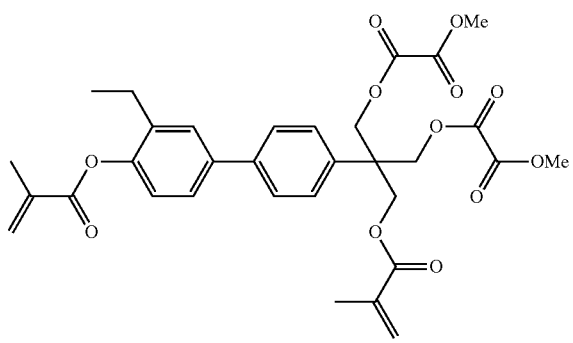
(x-18)
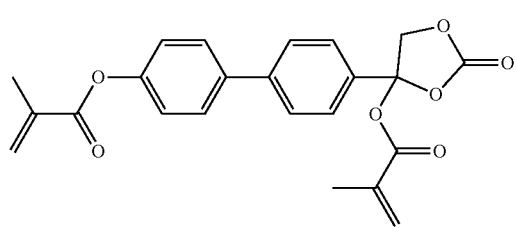
(y-18)
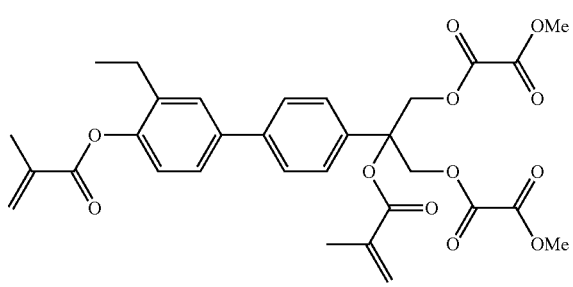
[Chem. 26]
(x-19)
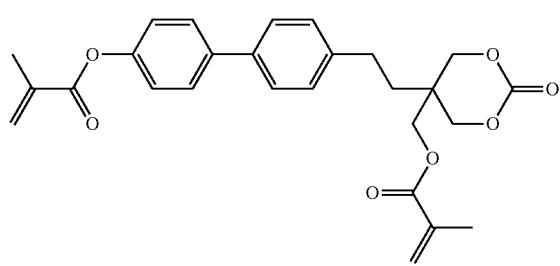
(y-19)
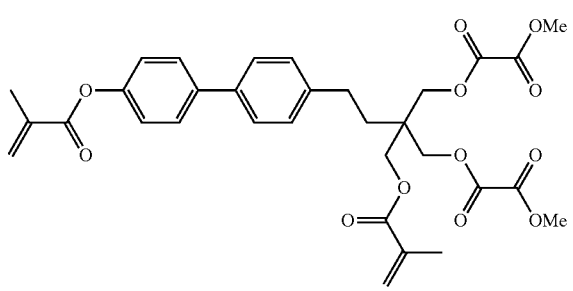

-continued
(x-20)
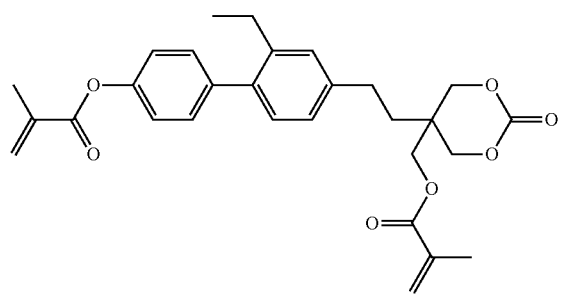
(y-20)
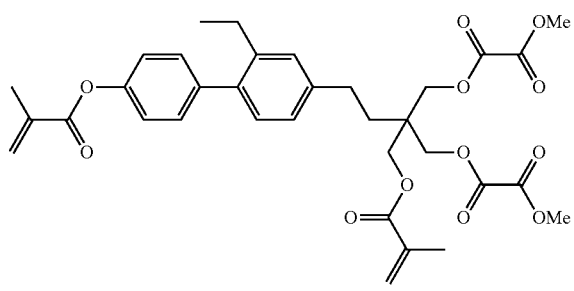
(x-21)
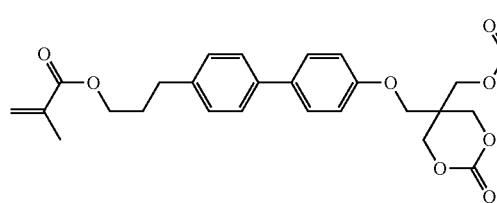
(y-21)
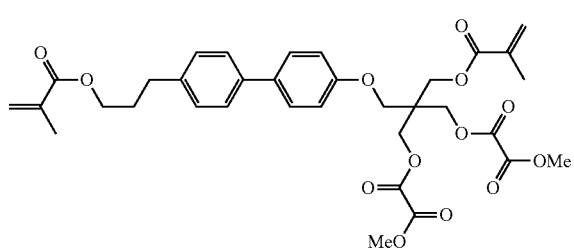
[Chem. 27]
(y-22)
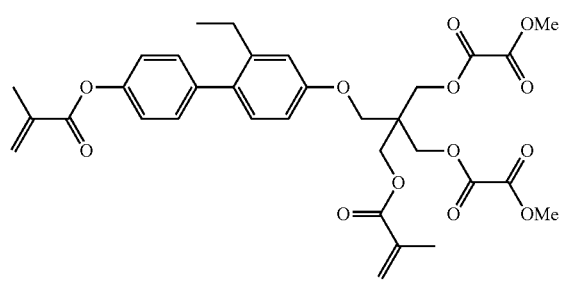
(y-25)
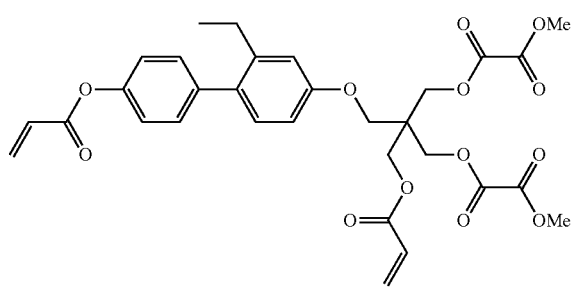
(y-23)
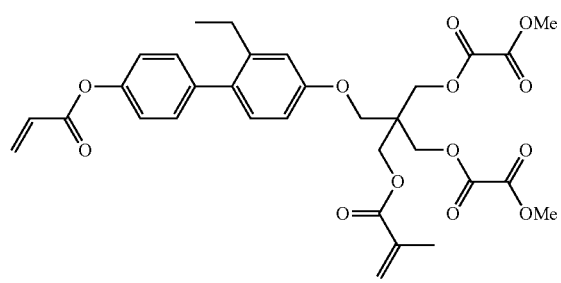
(y-24)
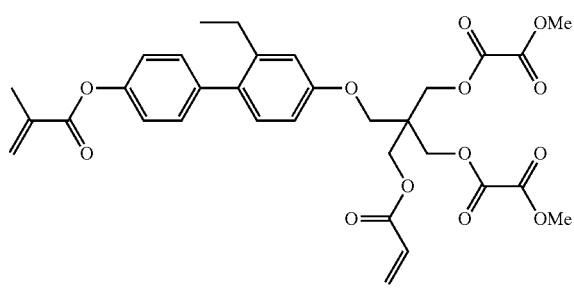
[Chem. 28]
(x-22)
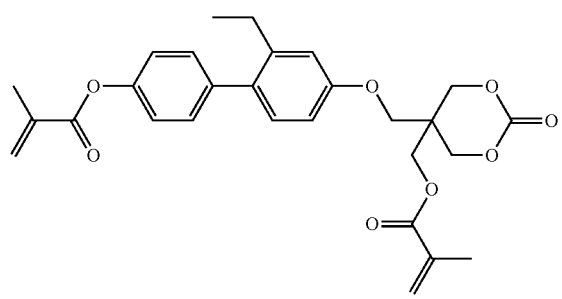
(x-25)
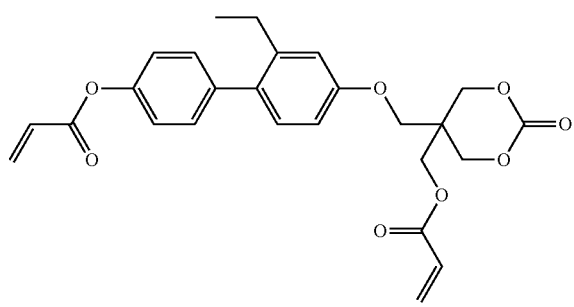

-continued
(x-23)
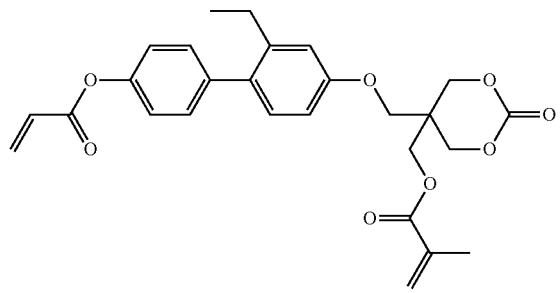
(x-26)
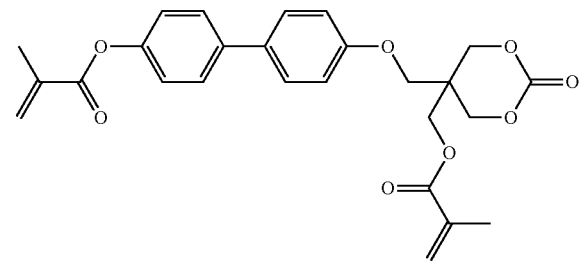
(x-24)
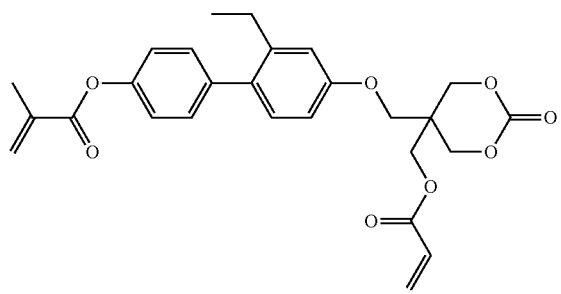
(x-27)
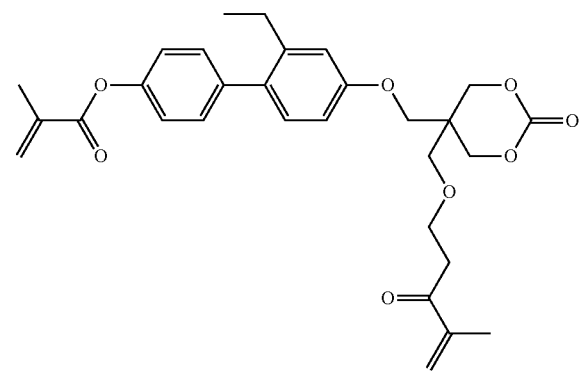
[Chem. 29]
(x-28)
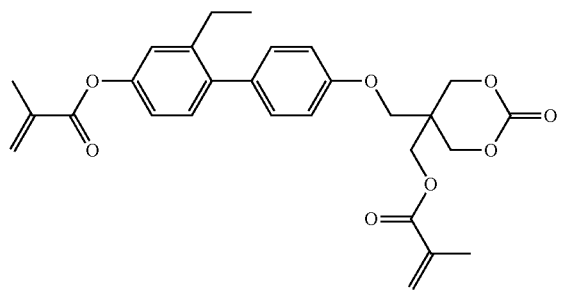
(x-30)
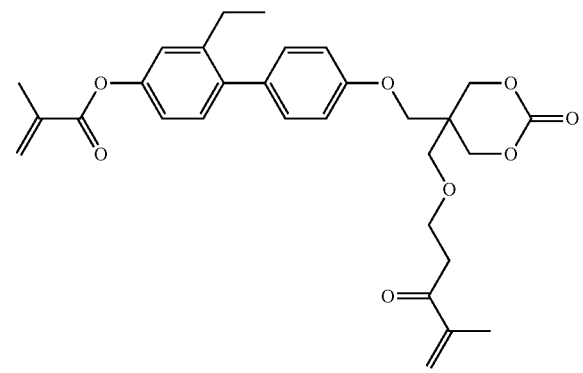
(x-29)
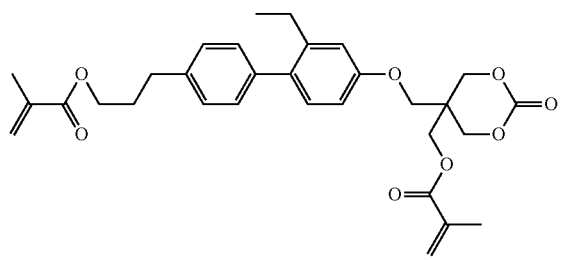
(x-31)
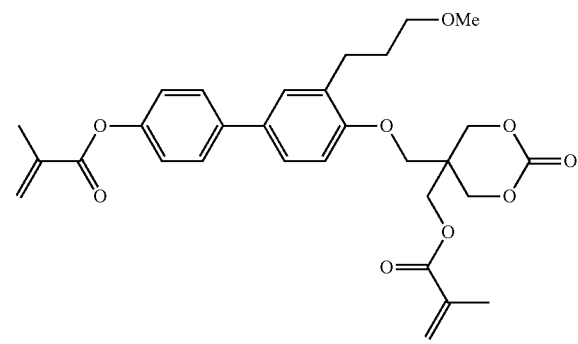

-continued

[Chem. 30]

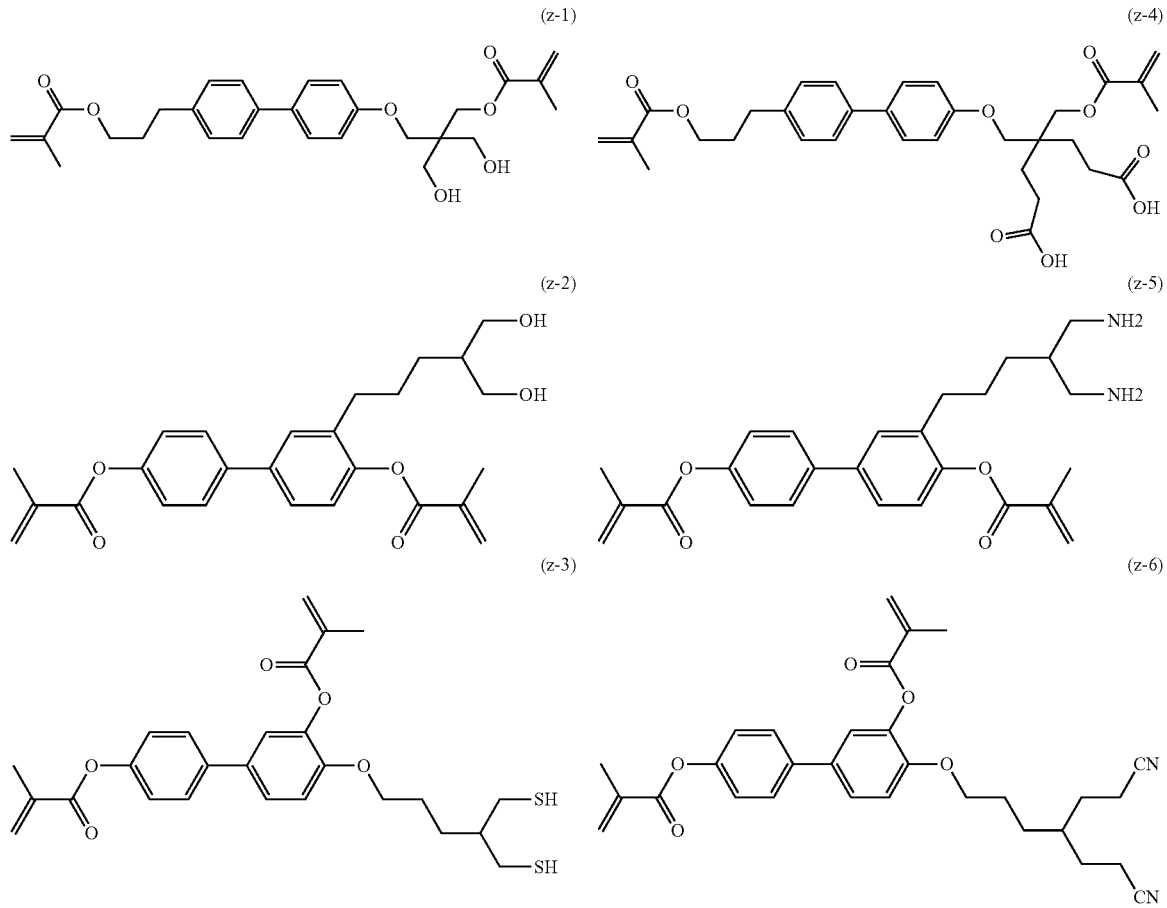

As stated, it is particularly preferred that compound(s) A, represented by general formula (Y), be compound(s) having a total m+n of 1. This means the compounds represented by formulae (x-1) to (x-12), (x-14) to (x-21), (y-1) to (y-12), (y-14) to (y-21), and (z-1) to (z-6) are preferred.

As stated, furthermore, it is preferred that compound(s) A, represented by general formula (Y), be compound(s) having a single bond as at least one of $S^{y1}$ or $S^{y2}$. This means the compounds represented by formulae (x-1) to (x-6), (x-8) to (x-12), (x-14) to (x-20), (y-1) to (y-6), (y-8) to (y-12), (y-14) to (y-20), (z-2), (z-3), (z-5), and (z-6) are preferred.

The liquid crystal composition according to the present invention may contain one compound A, represented by general formula (Y) above, or may contain two or more. By using two or more compounds A, represented by general formula (Y) above, with different polymerization rates in combination, the manufacturer can control the rate of polymerization in the liquid crystal composition according to the present invention properly. The residual monomer content is reduced, and an appropriate pretilt angle is also imparted. The use of two or more compounds represented by general formula (Y) above, furthermore, helps make the balance between the storage stability of and the rate of polymerization in the liquid crystal composition according to the present invention better.

Compound(s) A, represented by general formula (Y), can be insufficiently effective in improving the voltage holding ratio (VHR) if its percentage is too small, and affect the magnitude of change in pretilt angle if its percentage is too large.

It is, therefore, preferred that the minimum total percentage of compounds A, represented by general formula (Y), be 0.01% by mass, preferably 0.02% by mass, preferably 0.03% by mass, preferably 0.04% by mass, preferably 0.05% by mass, preferably 0.06% by mass, preferably 0.07% by mass, preferably 0.08% by mass, preferably 0.09% by mass, preferably 0.1% by mass, preferably 0.12% by mass, preferably 0.15% by mass, preferably 0.17% by mass, preferably 0.2% by mass, preferably 0.22% by mass, preferably 0.25% by mass, preferably 0.27% by mass, preferably 0.3% by mass, preferably 0.32% by mass, preferably 0.35% by mass, preferably 0.37% by mass, preferably 0.4% by mass, preferably 0.42% by mass, preferably 0.45% by mass, preferably 0.5% by mass, preferably 0.55% by mass of the entire liquid crystal composition according to the present invention.

It is, furthermore, preferred that the maximum total percentage of compounds A, represented by general formula (Y), be 3% by mass, preferably 2.5% by mass, preferably 2% by mass, preferably 1.5% by mass, preferably 1.3% by mass, preferably 1% by mass, preferably 0.95% by mass, preferably 0.9% by mass, preferably 0.85% by mass, preferably 0.8% by mass, preferably 0.75% by mass, preferably 0.7% by mass, preferably 0.65% by mass, preferably 0.6% by mass, preferably 0.55% by mass, preferably 0.5% by mass, preferably 0.45% by mass, preferably 0.4% by mass of the entire liquid crystal composition according to the present invention.

The preferred range for the total percentage of compounds A, represented by general formula (Y), can be determined by combining the above maxima and minima considering the effects of adding compound(s) A, the anchoring strength of the liquid crystal composition, the residual monomer content after the reaction of compound(s) A, the duration of the reaction, the impact on the reliability of the liquid crystal, etc. Of such ranges, 0.1% by mass to 3% by mass, 0.2% by mass to 2% by mass, 0.2% by mass to 1.3% by mass, 0.2% by mass to 1% by mass, and 0.2% by mass to 0.55% by mass of the entire liquid crystal composition according to the present invention are particularly preferred.

1-2. Polymerizable Compound(s) B

Preferably, the liquid crystal composition according to the present invention contains one polymerizable compound B, different from compound(s) A, or two or more polymerizable compounds B besides above-described compound(s) A, represented by general formula (Y). When containing polymerizable compound(s) B, the liquid crystal composition according to the present invention achieves a higher VHR and is suitable for use in the production of PSA liquid crystal display elements in particular.

Preferably, polymerizable compound(s) B is compound(s) represented by general formula (P) below. Any compound represented by general formula (Y), described above, is excluded from the compounds represented by general formula (P).

[Chem. 31]

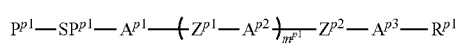

(P)

In general formula (P), $R^{p1}$ represents a hydrogen atom, a fluorine atom, a cyano group, a C1 to C15 alkyl group, or -$Sp^{p2}$-$P^{p2}$, optionally with one —$CH_2$— in the alkyl group, or nonadjacent two or more —$CH_2$-s in the alkyl group, substituted with —CH=CH—, —C≡C—, —O—, —CO—, —COO—, or —OCO— in such a manner that oxygen atoms are not consecutively next to each other, optionally with one hydrogen atom in the alkyl group, or each of two or more independently, substituted with a cyano group, a fluorine atom, or a chlorine atom.

$P^{p1}$ and $P^{p2}$ each independently represent polymerizable groups.

$Sp^{p1}$ and $Sp^{p2}$ each independently represent a single bond or a spacer group.

$Z^{p1}$ and $Z^{p2}$ each independently represent a single bond, —O—, —S—, —$CH_2$—, —$OCH_2$—, —$CH_2O$—, —CO—, —$C_2H_4$—, —COO—, —OCO—, —$OCOOCH_2$—, —$CH_2OCOO$—, —$OCH_2CH_2O$—, —CO—$NR^{ZP1}$—, —$NR^{ZP1}$—CO—, —$SCH_2$—, —$CH_2S$—, —CH=$CR^{ZP1}$—COO—, —CH=$CR^{ZP1}$—OCO—, —COO—$CR^{ZP1}$=CH—, —OCO—$CR^{ZP1}$=CH—, —COO—$CR^{ZP1}$=CH—COO—, —COO—$CR^{ZP1}$=CH—OCO—, —OCO—$CR^{ZP1}$=CH—COO—, —OCO—$CR^{ZP1}$=CH—OCO—, —($CH_2$)$_z$—COO—, —($CH_2$)$_z$—OCO—, —OCO— ($CH_2$)$_z$—, —(C=O)—O—($CH_2$)$_z$—, —CH=CH—, —CF=CF—, —CF=CH—, —CH=CF—, —$CF_2$—, —$CF_2O$—, —$OCF_2$—, —$CF_2CH_2$—, —$CH_2CF_2$—, —$CF_2CF_2$—, or —C≡C— (In the formulae, z at each occurrence independently represents an integer of 1 to 4, $R^{ZP1}$ at each occurrence independently represents a hydrogen atom or a $C_1$ to $C_4$ alkyl group, and if there are multiple $R^{ZP1}$s in the molecule, the $R^{ZP1}$s may be identical or different.).

$A^{p1}$ and $A^{p2}$ each independently represent a group selected from the group consisting of:

($a^p$) a 1,4-cyclohexylene group (One or two or more —$CH_2$-s present in the group may be substituted with —O— unless oxygen atoms come consecutively next to each other.);

($b^p$) a 1,4-phenylene group (One or two or more —CH=s present in the group may be substituted with —N=.); and ($c^p$) a naphthalene-2,6-diyl, naphthalene-1,4-diyl, naphthalene-1,5-diyl, 1,2,3,4-tetrahydronaphthalene-2,6-diyl, decahydronaphthalene-2,6-diyl, phenanthrene-2,7-diyl, or anthracene-2,6-diyl group (One or two or more —CH=s present in the group may be substituted with —N=.), optionally with one hydrogen atom present in the group ($a^p$), ($b^p$), or ($c^p$), or each of two or more independently, substituted with a cyano group, a halogen atom, a C1 to C8 alkyl group, a C1 to C8 alkoxy group, a C1 to C8 alkenyl group, or -$Sp^{p2}$-$P^{p2}$.

$A^{p3}$ represents a group selected from the group consisting of groups ($a^p$), ($b^p$), and ($c^p$) above and a single bond, and if $m^{p1}$ is 0 and if $A^{p1}$ is a group represented by group ($c^p$), $A^{p3}$ may be a single bond.

$m^{p1}$ represents 0, 1, 2, or 3.

If there are multiple $Z^{p1}$s, $A^{p2}$s, $Sp^{p2}$s, and/or $P^{p2}$s, the referents may be identical or different.

If $m^{p1}$ is 0 and if $A^{p1}$ is a group other than a naphthalenediyl, phenanthrene-2,7-diyl, or anthracene-2,6-diyl group, however, $A^{p3}$ represents a group, not a single bond.

Preferably, in general formula (P), $R^{p1}$ is -$Sp^{p2}$-$P^{p2}$.

Preferably, in general formula (P), $P^{p1}$ and $P^{p2}$ each independently represent any of general formulae ($P^{p1}$-1) to ($P^{p1}$-8) below, more preferably any of general formulae ($P^{p1}$-1) to ($P^{p1}$-3), even more preferably general formula ($P^{p1}$-1).

[Chem. 32]

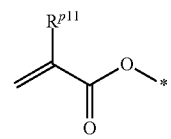

($P^{p1}$-1)

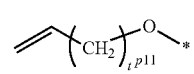

($P^{p1}$-2)

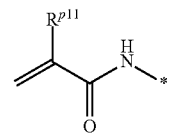

($P^{p1}$-3)

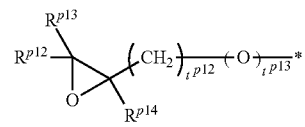

($P^{p1}$-4)

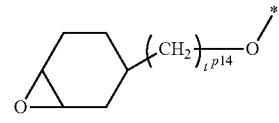

($P^{p1}$-5)

-continued

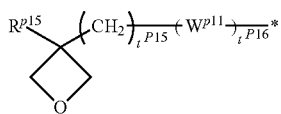
(P$^{p1}$-6)

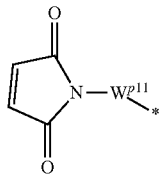
(P$^{p1}$-7)

HS—*  (P$^{p1}$-8)

In general formulae (P$^{p1}$-1) to (P$^{p1}$-8), R$^{p11}$, R$^{p12}$, R$^{p13}$, R$^{p14}$, and R$^{p15}$ each independently represent a hydrogen atom, a C1 to C5 alkyl group, or a C1 to C5 halogenated alkyl group.

W$^{p11}$ represents a single bond, —O—, —COO—, or a C1 to C5 alkylene group.

t$^{p11}$ represents 0, 1, or 2.

t$^{p12}$ and t$^{p13}$ each independently represent 0, 1, or 2. If t$^{p12}$ and/or t$^{p13}$ represents 0, that position(s) represents single bond(s).

t$^{p14}$ represents 0, 1, or 2.

t$^{p15}$ and t$^{p16}$ each independently represent 0, 1, or 2. If t$^{p15}$ and/or t$^{p16}$ represents 0, that position(s) represents single bond(s).

If there are multiple R$^{p11}$s, multiple R$^{p12}$s, multiple R$^{p13}$s, multiple R$^{p14}$s, multiple R$^{p15}$s, multiple W$^{p11}$s, multiple t$^{p11}$s, multiple t$^{p12}$s, multiple t$^{p13}$s, multiple t$^{p14}$s, multiple t$^{p15}$s, and multiple t$^{p16}$s, the referents may be identical or different.

Preferably, in general formula (P$^{p1}$-1) to (P$^{p1}$-8), each of R$^{p11}$, R$^{p12}$, and R$^{p13}$ is independently a hydrogen atom or a methyl group.

Preferably, t$^{p11}$ is 0 or 1.

Preferably, t$^{p14}$ is 0 or 1.

Preferably, each of t$^{p15}$ and t$^{p16}$ is independently 0 or 1.

Preferably, W$^{p11}$ is a single bond, —O—, —CH$_2$—, or —C$_2$H$_4$—.

Groups represented by general formulae (P$^{p1}$-1) to (P$^{p1}$-8) can further be groups represented by general formulae (P$^{p11}$-1) to (P$^{p11}$-10).

[Chem. 33]

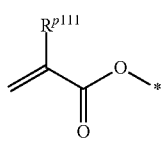
(P$^{p11}$-1)

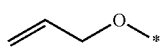
(P$^{p11}$-2)

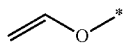
(P$^{p11}$-3)

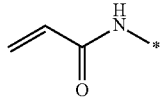
(P$^{p11}$-4)

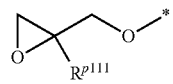
(P$^{p11}$-5)

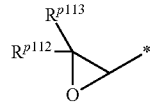
(P$^{p11}$-6)

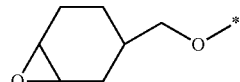
(P$^{p11}$-7)

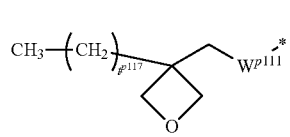
(P$^{p11}$-8)

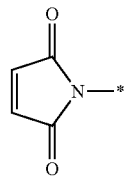
(P$^{p11}$-9)

HS—*  (P$^{p11}$-10)

In general formula (P$^{p11}$-1) to (P$^{p11}$-10), R$^{p111}$, R$^{p112}$, R$^{p113}$, and W$^{p111}$ express the same meaning as R$^{p11}$, R$^{p12}$, R$^{p13}$, and W$^{p11}$, respectively, and t$^{p117}$ represents 0, 1, or 2. If there are multiple R$^{p11}$s, R$^{p12}$s, W$^{p11}$s, and/or t$^{p11}$s, the referents may be identical or different.

In general formula (P), it is preferred that each of Z$^{p1}$ and Z$^{p2}$ be independently a single bond, —OCH$_2$—, —CH$_2$O—, —CO—, —C$_2$H$_4$—, —COO—, —OCO—, —COOC$_2$H$_4$—, —OCOC$_2$H$_4$—, —C$_2$H$_4$OCO—, —C$_2$H$_4$COO—, —CH=CH—, —CF$_2$—, —CF$_2$O—, —(CH$_2$)$_2$—COO—, —(CH$_2$)$_2$—OCO—, —OCO—(CH$_2$)$_2$—, —CH=CH—COO—, —COO—CH=CH—, —OCOCH=CH—, —COO—(CH$_2$)$_2$—, —OCF$_2$—, or —C≡C—. Of these, it is more preferred that each of Z$^{p1}$ and Z$^{p2}$ be independently a single bond, —OCH$_2$—, —CH$_2$O—, —C$_2$H$_4$—, —COO—, —OCO—, —COOC$_2$H$_4$—, —OCOC$_2$H$_4$—, —C$_2$H$_4$OCO—, —C$_2$H$_4$COO—, —CH=CH—, —(CH$_2$)$_2$—COO—, —(CH$_2$)$_2$—OCO—, —OCO—(CH$_2$)$_2$—, —CH=CH—COO—, —COO—CH=CH—, —OCOCH=CH—, —COO—(CH$_2$)$_2$—, or —C≡C—.

Preferably, only one of Z$^{p1}$ or Z$^{p2}$ present in the molecule is —OCH$_2$—, —CH$_2$O—, —C$_2$H$_4$—, —COO—, —OCO—, —COOC$_2$H$_4$—, —OCOC$_2$H$_4$—, —C$_2$H$_4$OCO—, —C$_2$H$_4$COO—, —CH=CH—, —(CH$_2$)$_2$—COO—, —(CH$_2$)$_2$—OCO—, —OCO—(CH$_2$)$_2$—, —CH=CH—COO—, —COO—CH=CH—, —OCOCH=CH—, —COO—(CH$_2$)$_2$—, or —C≡C—, and all the rest is single bond(s). More preferably, only one of Z$^{p1}$ or Z$^{p2}$ present in the molecule is —OCH$_2$—, —CH$_2$O—, —C$_2$H$_4$—, —COO—, or —OCO—, and all the rest is single bond(s). Even more preferably, all of Z$^{p1}$(s) and Z$^{p2}$ present in the molecule are single bonds.

Preferably, furthermore, only one of Z$^{p1}$ or Z$^{p2}$ present in the molecule is a linking group selected from the group consisting of —CH=CH—COO—, —COO—CH=CH—, —(CH$_2$)$_2$—COO—, —(CH$_2$)$_2$—OCO—, —O—CO—(CH$_2$)$_2$—, and —COO—(CH$_2$)$_2$—, and all the rest is single bond(s).

In general formula (P), Sp$^{p1}$ and Sp$^{p2}$ each independently represent a spacer group. Preferably, the spacer group represents a single bond or a linear or branched C1 to C30 alkylene group, optionally with one —CH$_2$— in the alkylene group, or nonadjacent two or more —CH$_2$-s in the alkylene group, substituted with —O—, —CO—, —COO—, —OCO—, —CH═CH—, or —C≡C— unless oxygen atoms are directly connected together, optionally with one or two or more hydrogen atoms in the alkylene group substituted with a fluorine atom. It is particularly preferred that each of Sp$^{p1}$ and Sp$^{p2}$ be independently a linear C1 to C10 alkylene group or a single bond.

In general formula (P), A$^{p1}$, A$^{p2}$, and A$^{p3}$ each independently represent a group selected from the group consisting of groups (a$^p$), (b$^p$), and (c$^p$) above. It is more preferred that A$^{p1}$, A$^{p2}$, and A$^{p1}$ each independently represent group (a$^p$) or (b$^p$), preferably a 1,4-phenylene or 1,4-cyclohexylene group, more preferably a 1,4-phenylene group. If m$^{p1}$ is 0 and if A$^{p1}$ is a group represented by group (c$^p$), it is preferred that A$^{p3}$ represent a single bond.

Preferably, furthermore, one or two or more hydrogen atoms present in the group (a$^p$), (b$^p$), or (c$^p$) are substituted with a fluorine atom, a C1 to C18 alkyl group, a C1 to C18 alkoxy group, a C2 to C18 alkenyl group, a cyano group, or -Sp$^{p2}$-P$^{p2}$. It is particularly preferred that the hydrogen atom(s) be substituted with a fluorine atom, a C1 to C8 alkyl group, a C1 to C8 alkoxy group, or -Sp$^{p2}$-P$^{p2}$. If A$^{p1}$, A$^{p2}$, and A$^{p3}$ each represent a 1,4-phenylene group, it is preferred that A$^{p1}$, A$^{p2}$, and A$^{p3}$ be each independently substituted with one fluorine atom, one methyl group, or one methoxy group. This is because this helps improve miscibility with the liquid crystal molecules (liquid crystal compound(s)).

Preferably, in general formula (P), m$^{p1}$ is 0, 1, or 2, preferably 0 or 1.

One preferred form of a polymerizable compound represented by general formula (P) is a compound represented by general formula (RM) below.

[Chem. 34]

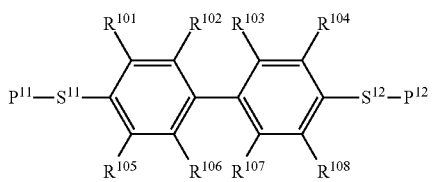

(RM)

In general formula (RM), R$^{101}$, R$^{102}$, R$^{103}$, R$^{104}$, R$^{105}$, R$^{106}$, R$^{107}$, and R$^{108}$ each independently represent P$^{13}$—S$^{13}$—, a C1 to C18 alkyl group optionally substituted by fluorine atom(s), a C1 to C18 alkoxy group optionally substituted by fluorine atom(s), a fluorine atom, or a hydrogen atom, P$^{11}$, P$^{12}$, and P$^{13}$ each independently represent a polymerizable group, S$^{11}$, S$^{12}$, and S$^{13}$ each independently represent a single bond or a C1 to C15 alkylene group, optionally with one —CH$_2$— in the alkylene group, or nonadjacent two or more —CH$_2$-s in the alkylene group, substituted with —O—, —OCO—, or —COO— in such a manner that oxygen atoms are not directly connected, and if there are multiple P$^{13}$s and S$^{13}$s, the multiple P$^{13}$s may be identical or different, and the multiple S$^{13}$s may be identical or different.

In general formula (RM), R$^{101}$, R$^{102}$, R$^{103}$, R$^{104}$, R$^{105}$, R$^{106}$, R$^{107}$, and R$^{108}$ each independently represent P$^{13}$—S$^{13}$—, a C1 to C18 alkyl group optionally substituted by fluorine atom(s), a C1 to C18 alkoxy group optionally substituted by fluorine atom(s), a fluorine atom, or a hydrogen atom. Preferred numbers of carbon atoms in an alkyl or alkoxy group range from 1 to 16. More preferably, the number of carbon atoms is 1 to 10, even more preferably 1 to 8, still more preferably 1 to 6, yet more preferably 1 to 3. The alkyl or alkoxy group may be linear or branched, but a linear one is particularly preferred.

Preferably, in general formula (RM), R$^{101}$, R$^{102}$, R$^{103}$, R$^{104}$, R$^{105}$, R$^{106}$, R$^{107}$, and R$^{108}$ each independently represent any of P$^{13}$—S$^{13}$—, a C1 to C3 alkyl group, a C1 to C3 alkoxy group, a fluorine atom, or a hydrogen atom, more preferably any of P$^{13}$—S$^{13}$—, a C1 to C3 alkoxy group, a fluorine atom, or a hydrogen atom. An alkoxy group preferably has one or more and three or fewer carbon atoms, more preferably one or more and two or fewer. It is particularly preferred that the number of carbon atoms is one, or that the alkoxy group be a methoxy group.

In general formula (RM), P$^{11}$, P$^{12}$, and P$^{13}$ may all be identical polymerizable groups or may be different polymerizable groups. Preferably, each of P$^{11}$, P$^{12}$, and P$^{13}$ is independently a polymerizable group represented by any of formulae (Re-1) to (Re-9).

[Chem. 35]

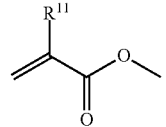

(Re-1)

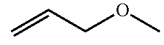

(Re-2)

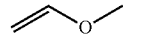

(Re-3)

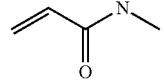

(Re-4)

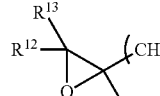

(Re-5)

(Re-6)

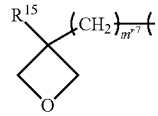

(Re-7)

-continued

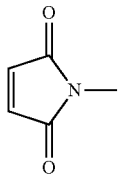
(Re-8)

HS— (Re-9)

In formulae (Re-1) to (Re-9), $R^{11}$, $R^{12}$, $R^{13}$, $R^{14}$, and $R^{15}$ each independently represent a C1 to C5 alkyl group, a fluorine atom, or a hydrogen atom, and $m^{r5}$, $m^{r7}$, $n^{r5}$, and $n^{r7}$ each independently represent 0, 1, or 2. If $m^{r5}$, $m^{r7}$, $n^{r5}$, and/or $n^{r7}$ represents 0, that position (s) represents single bond(s).

It is particularly preferred that each of $P^{11}$, $P^{12}$, and $P^{13}$ be independently a group represented by formula (Re-1), (Re-2), (Re-3), (Re-4), (Re-5), or (Re-7), more preferably a group represented by formula (Re-1), (Re-2), (Re-3), or (Re-4), even more preferably a group represented by formula (Re-1), in particular an acrylic or methacrylic group. Preferably, at least one of $P^{11}$ or $P^{12}$ is formula (Re-1), more preferably an acrylic or methacrylic group, even more preferably a methacrylic group. It is particularly preferred that $P^{11}$ and $P^{12}$ be methacrylic groups.

Preferably, in general formula (RM) above, each of $S^{11}$, $S^{12}$, and $S^{13}$ is independently a single bond or a C1 to C5 alkylene group, in particular a single bond. If the drive technology of the liquid crystal display element according to the present invention is PSA or PSVA, it is preferred that each of $S^{11}$, $S^{12}$, and $S^{13}$ in general formula (RM) above be independently a single bond. This is because this ensures, in the production of liquid crystal display elements according to the present invention, that the residual amount of polymerizable compound(s) B after the irradiation with actinic rays of energy will be sufficiently small, and that display defects (e.g., image-sticking) caused by a change in pretilt angle will be eliminated or significantly reduced. If the drive technology of the liquid crystal display element according to the present invention is NPS, it is preferred that $S^{11}$, $S^{12}$, and $S^{13}$ in general formula (RM) above have one to three carbon atoms.

One preferred form of polymerizable compound B represented by general formula (P) is a compound represented by general formula (i) below.

[Chem. 36]

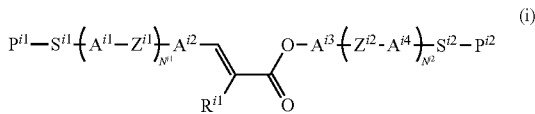
(i)

In general formula (i), $P^{i1}$ and $P^{i2}$ each independently represent a polymerizable group.

$S^{i1}$ and $S^{i2}$ each independently represent a spacer group. $Z^{i1}$ and $Z^{i2}$ each independently represent a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^{ZP1}$—, —NR$^{ZP1}$—CO—, —SCH$_2$—, —CH$_2$S—, —CH=CR$^{ZP1}$—COO—, —CH=CR$^{ZP1}$—OCO—, —COO—CR$^{ZP1}$=CH—, —OCO—CR$^{ZP1}$=CH—, —COO—CR$^{ZP1}$=CH—COO—, —COO—CR$^{ZP1}$=CH—OCO—, —OCO—CR$^{ZP1}$=CH—COO—, —OCO—CR$^{ZP1}$=CH—OCO—, —(CH$_2$)$_2$—COO—, —(CH$_2$)$_2$—OCO—, —OCO—(CH$_2$)$_2$—, —(C=O)—O—(CH$_2$)$_2$—, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C— (In the formulae, $R^{ZP1}$ at each occurrence independently represents a hydrogen atom or a C1 to C4 alkyl group, and if there are multiple $R^{ZP1}$s in the molecule, they may be identical or different.).

$A^{i1}$, $A^{i2}$, $A^{i3}$, and $A^{i4}$ each independently represent a group selected from the group consisting of:

($a^p$) a 1,4-cyclohexylene group (One or two or more —CH$_2$-s present in the group may be substituted with —O— unless oxygen atoms come consecutively next to each other.);

($b^p$) a 1,4-phenylene group (One or two or more —CH=s present in the group may be substituted with —N=.); and ($c^p$) a naphthalene-2,6-diyl, naphthalene-1,4-diyl, naphthalene-1,5-diyl, 1,2,3,4-tetrahydronaphthalene-2,6-diyl, decahydronaphthalene-2,6-diyl, phenanthrene-2,7-diyl, or anthracene-2,6-diyl group (One or two or more —CH=s present in the group may be substituted with —N=.), optionally with one hydrogen atom present in the group ($a^p$), ($b^p$), or ($c^p$), or each of two or more independently, substituted with a cyano group, a C1 to C18 alkyl group optionally substituted by fluorine atom(s), or -Sp$^{p2}$-P$^{p2}$, optionally with one —CH$_2$— in the alkyl group, or each of nonadjacent two or more —CH$_2$-s in the alkyl group independently, substituted by —CH=CH—, —C≡C—, —O—, —CO—, —COO—, or —OCO— in such a manner that oxygen atoms are not consecutively next to each other.

$R^{i1}$ represents a C$_1$ to C$_5$ alkyl group, a fluorine atom, or a hydrogen atom, and $n^{i1}$ and $n^{i2}$ each independently represent 0, 1, 2, or 3, with the proviso that $n^{i1}+n^{i2}$ represents 0, 1, 2, or 3.

If there are multiple $A^{i1}$s, multiple $A^{i4}$s, multiple $Z^{i1}$s, and multiple $Z^{i2}$s in the molecule, the referents may be identical or different.

Preferably, each of $A^{i1}$ and $A^{i4}$ is independently a 1,4-phenylene, 1,4-cyclohexylene, pyridine-2,5-diyl, pyrimidine-2,5-diyl, or naphthalene-2,6-diyl group, preferably a 1,4-cyclohexylene, 1,4-phenylene, or naphthalene-2,6-diyl group. One or two or more hydrogen atoms in the group may be substituted with a fluorine atom, a C to C8 alkyl group, a C1 to C8 alkoxy group, or -Sp$^{p2}$-P$^{p2}$ and preferably are substituted with a fluorine atom, a methyl group, or a methoxy group. This is because this helps improve miscibility with the liquid crystal molecules (liquid crystal compound(s)).

Preferably, $A^{i2}$ is a 1,4-phenylene group. One or two or more hydrogen atoms in the 1,4-phenylene group may be substituted with a fluorine atom, a C1 to C8 alkyl group, a C1 to C8 alkoxy group, or -Sp$^{p2}$-P$^{p2}$ and preferably are substituted with a fluorine atom, a methyl group, or a methoxy group. This is because this helps improve miscibility with the liquid crystal molecules (liquid crystal compound(s)).

Preferably, $A^{i3}$ represents a 1,4-cyclohexylene or 1,4-phenylene group, a naphthalene-1,4-diyl group, a naphthalene-1,5-diyl group, or a naphthalene-2,6-diyl group. Of these, it is more preferred that $A^{i3}$ represent a 1,4-phenylene group. One or two or more hydrogen atoms in the 1,4-phenylene group may be substituted with a fluorine atom, a C1 to C8 alkyl group, a C1 to C8 alkoxy group, or -Sp$^{p2}$-P$^{p2}$ and preferably are substituted with a fluorine atom, a methyl group, or a methoxy group. This is because this helps improve miscibility with the liquid crystal molecules (liquid crystal compound(s)).

Preferably, $P^{i1}$ and $P^{i2}$ each independently represent any of general formulae ($P^{p1}$-1) to ($P^{p1}$-8) above, more preferably any of general formulae ($P^{p1}$-1) to ($P^{p1}$-3), even more preferably general formula ($P^{p1}$-1).

Preferably, $S^{i1}$ and $S^{i2}$ each independently represent a single bond or a linear or branched C1 to C30 alkylene group, optionally with one —$CH_2$— in the alkylene group, or nonadjacent two or more —$CH_2$-s in the alkylene group, substituted with —O—, —CO—, —COO—, —OCO—, —CH=CH—, or —C≡C— unless oxygen atoms are directly connected together, optionally with one or two or more hydrogen atoms in the alkylene group substituted with a fluorine atom. It is particularly preferred that each of $S^{i1}$ and $S^{i2}$ be independently a linear C1 to C10 alkylene group or a single bond.

Preferably, each of $Z^{i1}$ and $Z^{i2}$ is independently —O—, —$OCH_2$—, —$CH_2O$—, —COO—, —OCO—, —$C_2H_4$—, —C≡C—, or a single bond, more preferably —$OCH_2$—, —$CH_2O$—, —COO—, —OCO—, or a single bond, for easier alignment of the liquid crystal.

Preferably, $R^{i1}$ is a methyl group, an ethyl group, a fluorine atom, or a hydrogen atom, more preferably a hydrogen atom.

Preferably, $n^{i1}$ and $n^{i2}$ are the combination of 0 and 0, that of 1 for $n^{i1}$ and 0 for $n^{i2}$, that of 2 for $n^{i1}$ and 0 for $n^{i2}$, that of 1 for $n^{i1}$ and 1 for $n^{i2}$, or that of 0 for $n^{i1}$ and 2 for $n^{i2}$.

Preferred examples of polymerizable compounds B represented by general formula (P) include the polymerizable compounds represented by formulae (P-1-1) to (P-1-48) below.

[Chem. 37]

(P-1-1)

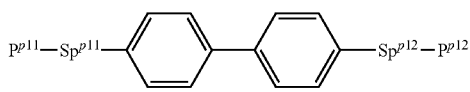

(P-1-2)

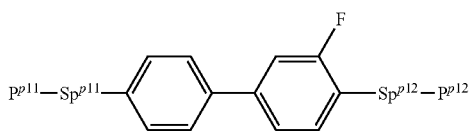

(P-1-3)

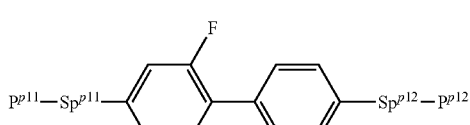

(P-1-4)

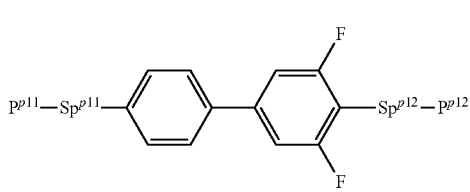

(P-1-5)

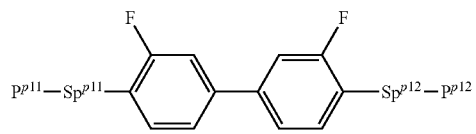

(P-1-6)

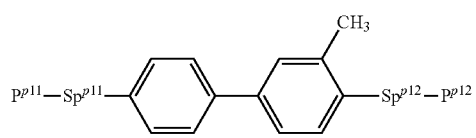

(P-1-7)

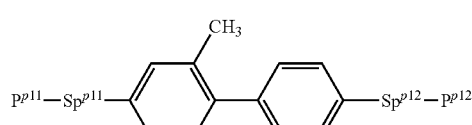

(P-1-8)

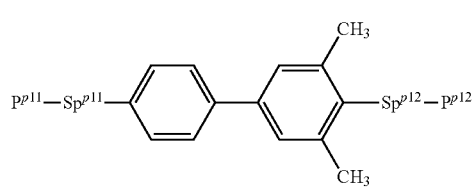

(P-1-9)

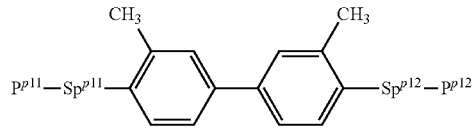

[Chem. 38]

(P-1-10)

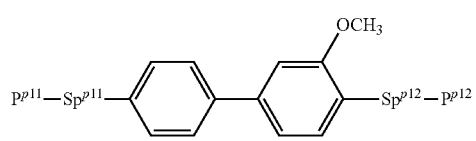

(P-1-11)

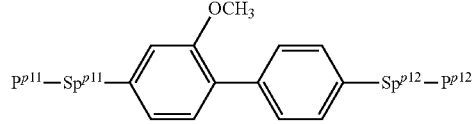

(P-1-12)

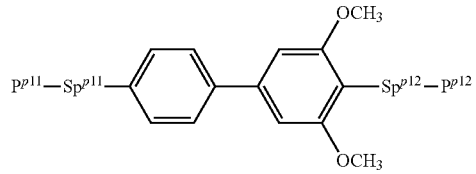

(P-1-13)

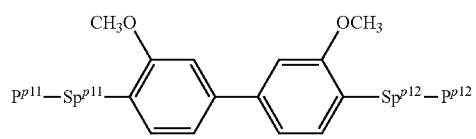

(P-1-14)
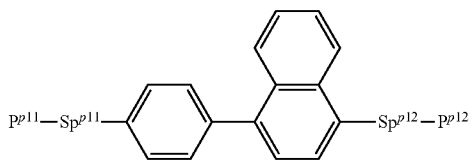
[Chem. 39]
(P-1-21)
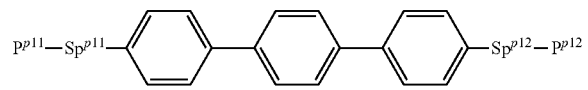
(P-1-22)
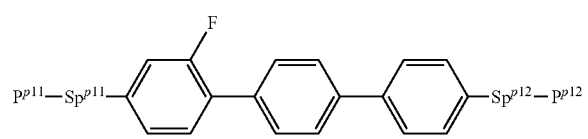
(P-1-23)
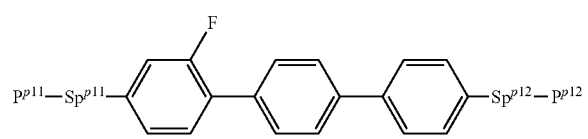
(P-1-24)
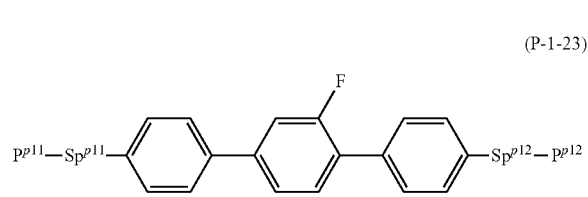
(P-1-25)
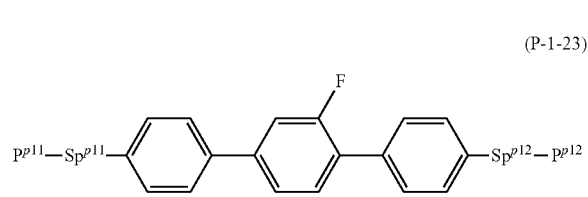
(P-1-26)
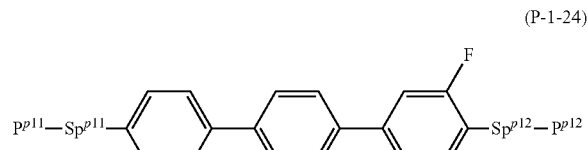
(P-1-27)
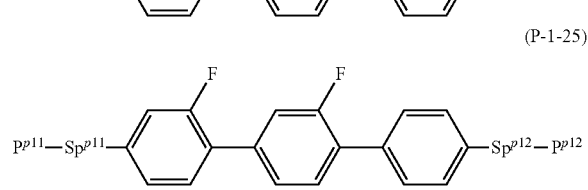
[Chem. 40]
(P-1-32)
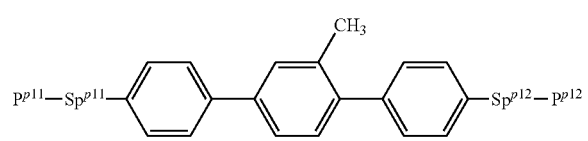
[Chem. 41]
(P-1-41)
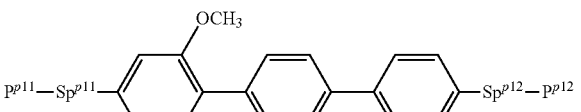
(P-1-42)
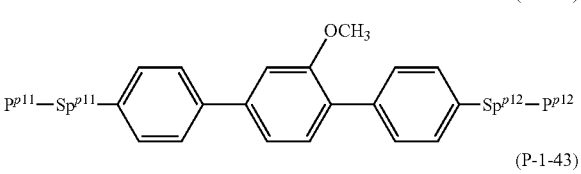
(P-1-43)
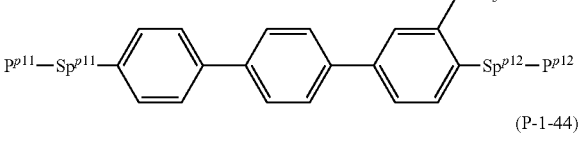
(P-1-44)
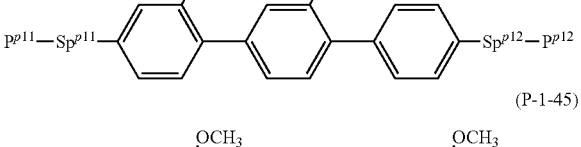
(P-1-45)
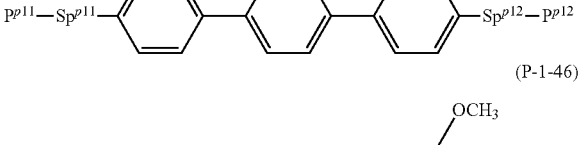
(P-1-46)
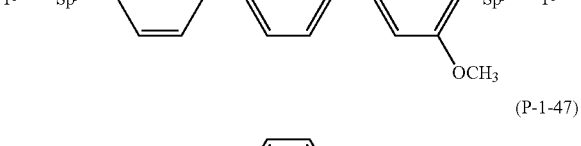
(P-1-47)
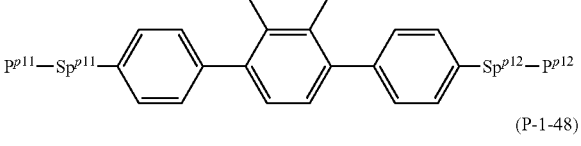
(P-1-48)
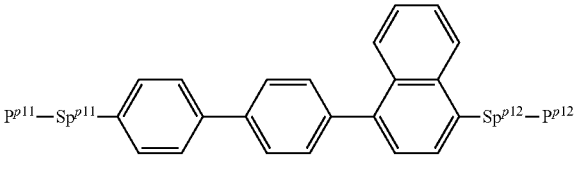
In formulae (P-1-1) to (P-1-48), $P^{p11}$, $P^{p12}$, $Sp^{p11}$, and $Sp^{p12}$ express the same meaning as $P^{p1}$, $P^{p2}$, $Sp^{p1}$, and $Sp^{p2}$ in general formula (P).
The polymerizable compounds represented by formulae (P-2-1) to (P-2-18) below are also preferred examples of polymerizable compounds represented by general formula (P).

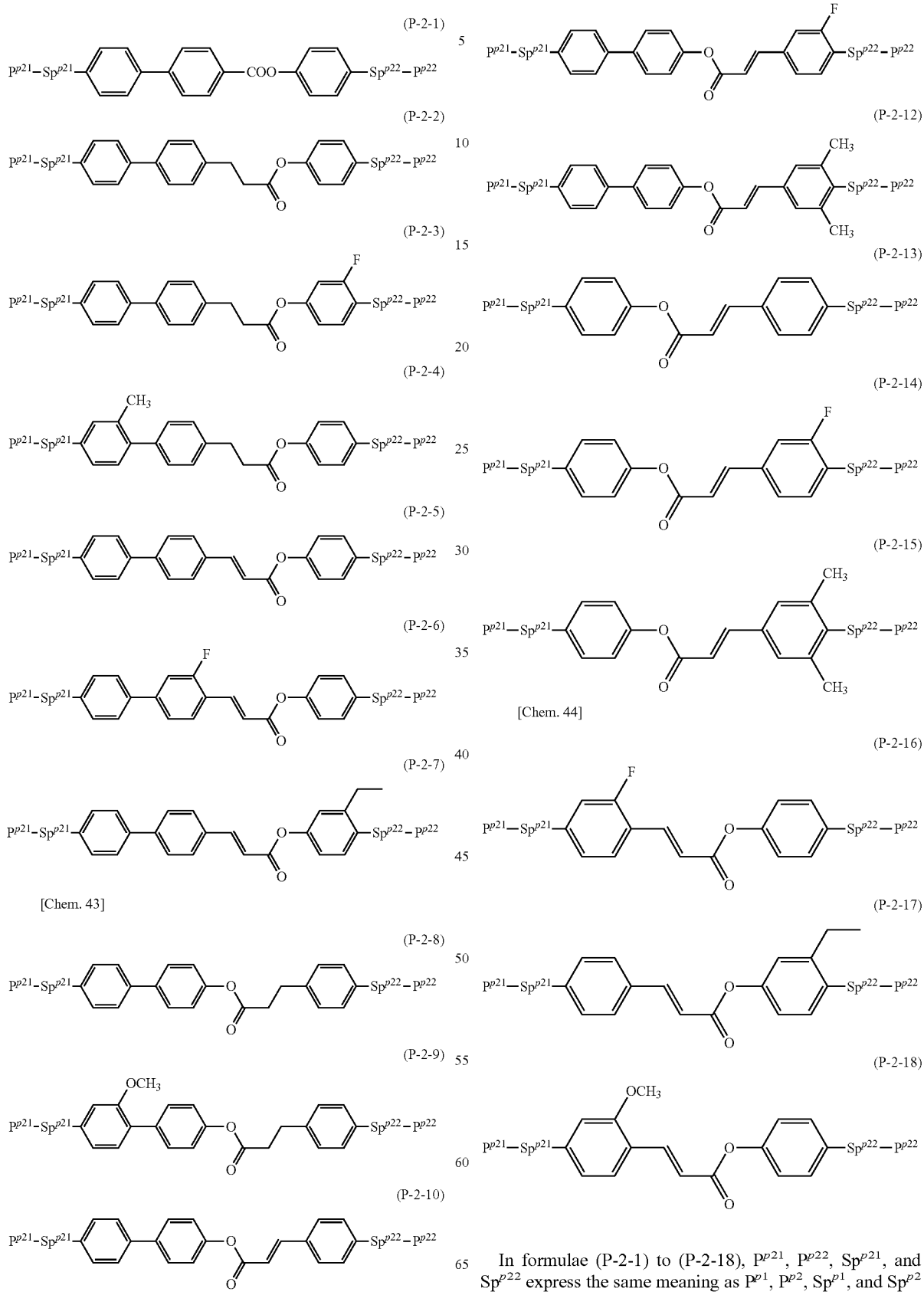
In formulae (P-2-1) to (P-2-18), $P^{p21}$, $P^{p22}$, $Sp^{p21}$, and $Sp^{p22}$ express the same meaning as $P^{p1}$, $P^{p2}$, $Sp^{p1}$, and $Sp^{p2}$ in general formula (P).

The polymerizable compounds represented by formulae (P-3-1) to (P-3-15) below are also preferred examples of polymerizable compounds represented by general formula (P).

[Chem. 45]

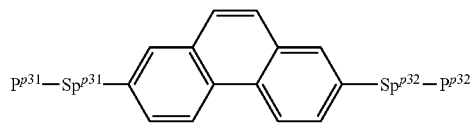

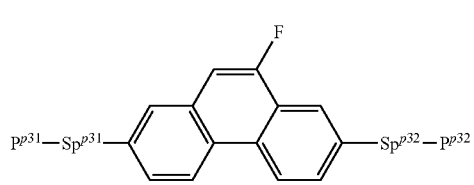

In formulae (P-3-1) to (P-3-15), $P^{p31}$, $P^{p32}$, $Sp^{p31}$, and $Sp^{p32}$ express the same meaning as $P^{p1}$, $P^{p2}$, $Sp^{p1}$, and $Sp^{p2}$ in general formula (P).

The polymerizable compounds represented by formulae (P-4-1) to (P-4-19) below are also preferred examples of polymerizable compounds represented by general formula (P).

[Chem. 47]
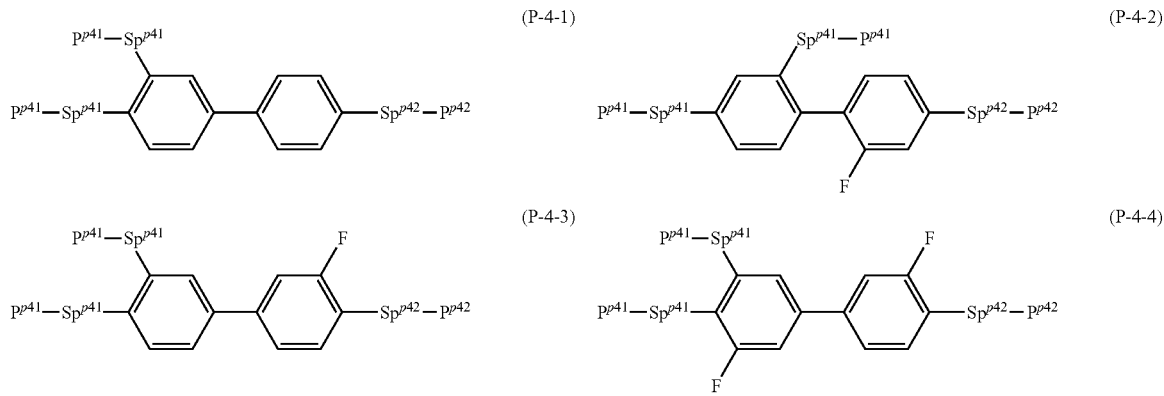
[Chem. 48]
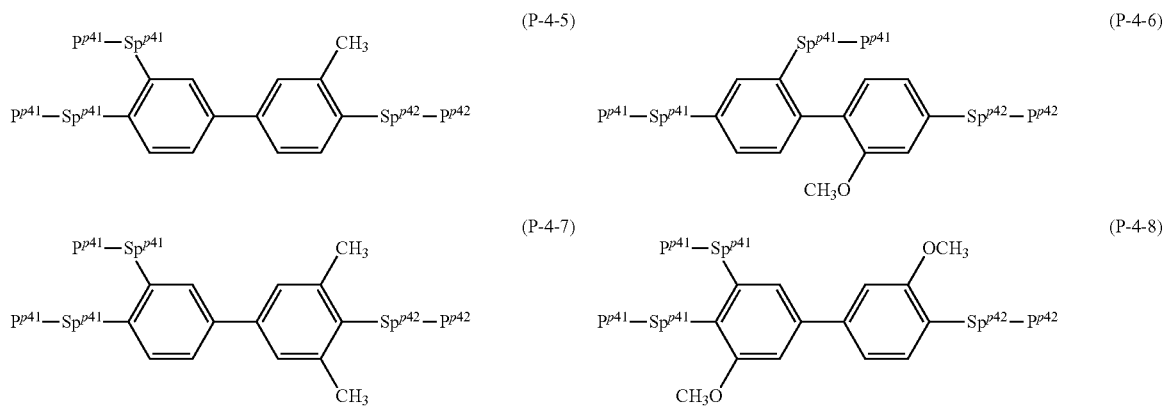
[Chem. 49]
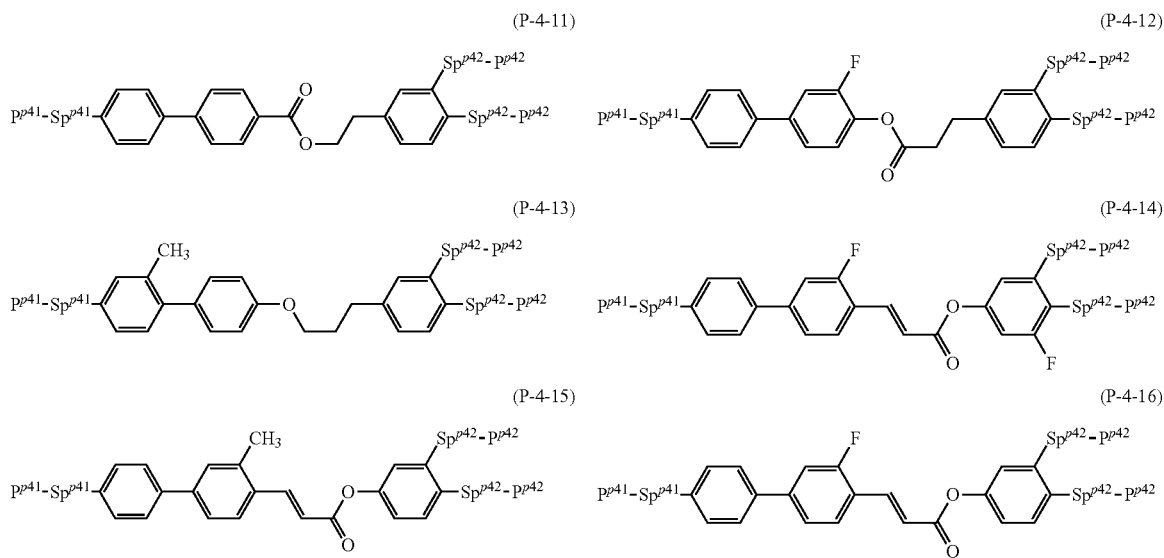
[Chem. 50]
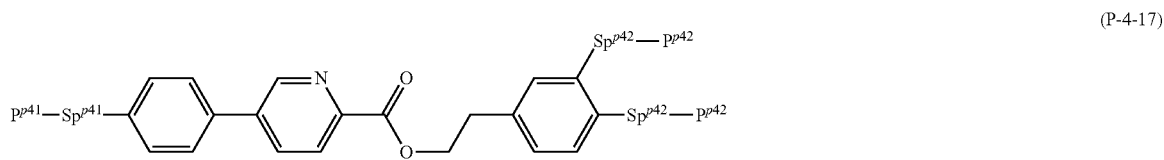

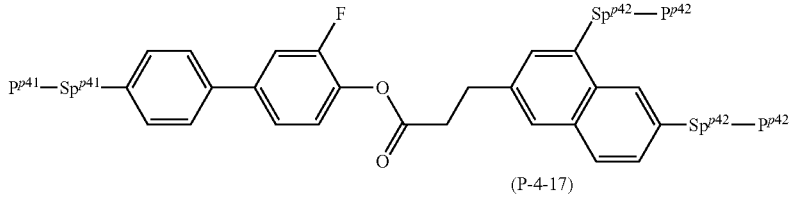
(P-4-17)

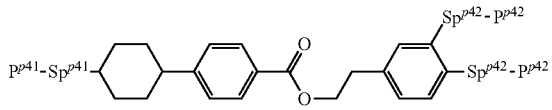
(P-4-18)

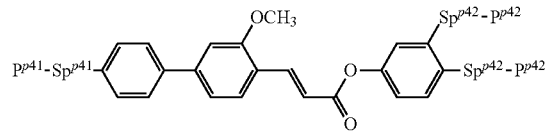
(P-4-18)

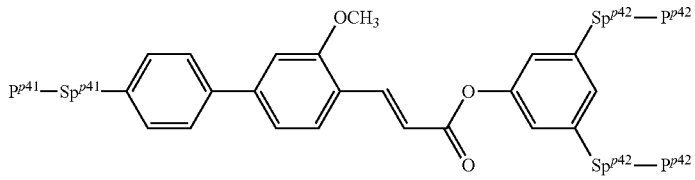
(P-4-19)

In formulae (P-4-1) to (P-4-19), $P^{p41}$, $P^{p42}$, $Sp^{p41}$, and $Sp^{p42}$ express the same meaning as $P^{p1}$, $P^{p2}$, $Sp^{p1}$, and $Sp^{p2}$ in general formula (P).

The liquid crystal composition according to the present invention may contain one polymerizable compound B represented by general formula (P) above or may contain two or more. By using two or three or more compounds B represented by general formula (P) above with different polymerization rates in combination, the manufacturer can control the rate of polymerization in the liquid crystal composition according to the present invention properly. The residual monomer content is reduced, and an appropriate pretilt angle is also imparted. The use of two or more compounds B represented by general formula (P) above, furthermore, helps make the balance between the storage stability of and the rate of polymerization in the liquid crystal composition according to the present invention better.

It is particularly preferred that the polymerizable compound(s) B represented by general formula (P) in the liquid crystal composition according to the present invention be one or two or more compounds selected from the group consisting of the compounds represented by general formula (RM) above and those represented by general formula (i).

Preferably, the minimum total percentage of polymerizable compounds B represented by general formula (P) is 0.01% by mass, preferably 0.02% by mass, preferably 0.03% by mass, preferably 0.04% by mass, preferably 0.05% by mass, preferably 0.06% by mass, preferably 0.07% by mass, preferably 0.08% by mass, preferably 0.09% by mass, preferably 0.1% by mass, preferably 0.12% by mass, preferably 0.15% by mass, preferably 0.17% by mass, preferably 0.2% by mass, preferably 0.22% by mass, preferably 0.25% by mass, preferably 0.27% by mass, preferably 0.3% by mass, preferably 0.32% by mass, preferably 0.35% by mass, preferably 0.37% by mass, preferably 0.4% by mass, preferably 0.42% by mass, preferably 0.45% by mass, preferably 0.5% by mass, preferably 0.55% by mass of the entire liquid crystal composition according to the present invention.

Preferably, furthermore, the maximum total percentage of polymerizable compounds B represented by general formula (P) is 10% by mass, preferably 8% by mass, preferably 5% by mass, preferably 4.5% by mass, preferably 4% by mass, preferably 3.5% by mass, preferably 3% by mass, preferably 2.5% by mass, preferably 2% by mass, preferably 1.5% by mass, preferably 1.3% by mass, preferably 1% by mass, preferably 0.95% by mass, preferably 0.9% by mass, preferably 0.85% by mass, preferably 0.8% by mass, preferably 0.75% by mass, preferably 0.7% by mass, preferably 0.65% by mass, preferably 0.6% by mass, preferably 0.55% by mass, preferably 0.5% by mass, preferably 0.45% by mass, preferably 0.4% by mass of the entire liquid crystal composition according to the present invention.

The preferred range for the total percentage of polymerizable compounds B represented by general formula (P) can be determined by combining the above maxima and minima considering the effects of adding polymerizable compound(s) B, the anchoring strength of the liquid crystal composition, the residual monomer content after the reaction of polymerizable compound(s) B, the duration of the reaction, the impact on the reliability of the liquid crystal, etc. Of such ranges, 0.05% by mass to 10% by mass, 0.1% by mass to 8% by mass, 0.1% by mass to 5% by mass, 0.1% by mass to 3% by mass, 0.2% by mass to 2% by mass, 0.2% by mass to 1.3% by mass, 0.2% by mass to 1% by mass, and 0.2% by mass to 0.55% by mass of the entire liquid crystal composition according to the present invention are particularly preferred.

1-[2]3. Compound(s) C

Preferably, the liquid crystal composition according to the present invention contains one compound C, represented by general formula (II), or two or more compounds C besides above-described compound(s) A, represented by general formula (Y). Any compound A as described above, represented by general formula (Y), and any polymerizable compound B as described above, represented by general formula (P), are excluded from compounds C, represented by general formula (II). As stated later, at least one of $R^{J11}$ or $R^{J12}$ represents a C2 to C10 alkenyl group, so compounds C are generally referred to as "alkenyl compounds." The presence of compound(s) C, in particular, in the liquid crystal composition according to the present invention makes it certain that quick response will be achieved.

[Chem. 51]

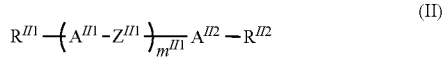
(II)

In general formula (II), $R^{II1}$ represents a C1 to C10 alkyl group or a C2 to C10 alkenyl group, optionally with one —$CH_2$— in the alkyl group, or each of nonadjacent two or more —$CH_2$-s in the alkyl group independently, substituted by —CH=CH—, —C≡C—, —O—, —CO—, —COO—, or —OCO— unless oxygen atoms come consecutively next to each other.

$R^{II2}$ represents a hydrogen atom, a halogen atom, a cyano group, a C1 to C10 alkyl group, or a C2 to C10 alkenyl group, optionally with one —$CH_2$— in the alkyl group, or each of nonadjacent two or more —$CH_2$-s in the alkyl group independently, substituted by —CH=CH—, —C≡C—, —O—, —CO—, —COO—, or —OCO— unless oxygen atoms come consecutively next to each other, optionally with one or two or more hydrogen atoms in the alkyl group substituted with a halogen atom.

At least one of $R^{II1}$ or $R^{II2}$, however, represents a C2 to C10 alkenyl group.

$A^{II1}$ and $A^{II2}$ each independently represent a group selected from the group consisting of:

(a) a 1,4-cyclohexylene group (One —$CH_2$— or two or more nonadjacent —$CH_2$-s present in the group may be replaced by —O— unless oxygen atoms come consecutively next to each other.);

(b) a 1,4-phenylene group (One —CH= or two or more nonadjacent —CH=s present in the group may be replaced by —N=.); and (c) a 2,6-naphthalenediyl, 1,2,3,4-tetrahydronaphthalene-2,6-diyl, or decahydronaphthalene-2,6-diyl group (One or two or more —CH=s present in the group may be replaced by —N=.), optionally with the groups (a), (b), and (c) each independently substituted with a cyano group or a halogen atom.

$Z^{II1}$ represents a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—.

$m^{II1}$ represents 1, 2, 3, or 4.

If $m^{II1}$ represents 2, 3, or 4, the multiple $A^{II1}$s may be identical or different, and the multiple $Z^{II1}$s may be identical or different.

In general formula (II), at least one of $R^{II1}$ or $R^{II2}$ represents a C2 to C10 alkenyl group. It is particularly preferred that $R^{II1}$ and/or $R^{II2}$ represent a C2 to C8 alkenyl group, preferably a C2 to C5 alkenyl group, preferably a C2 or C3 alkenyl group, preferably a C2 alkenyl group.

Preferably, at least one of $R^{II1}$ or $R^{II2}$ represents a group selected from the group consisting of formulae (R1) to (R5) below. More preferably, $R^{II1}$ and/or $R^{II2}$ represents formula (R1) or (R2), even more preferably formula (R1), because in those cases the compound is more effective in reducing the rotational viscosity ($\gamma_1$) of the liquid crystal composition.

[Chem. 52]

(R1)

(R2)

(R3)

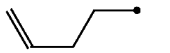
(R4)

(R5)

The black dot in each formula represents a carbon atom in the ring structure represented by $A^{II1}$ or $A^{II2}$.

Compound(s) C, represented by general formula (II), may be nonpolar, or dielectrically substantially neutral, compound(s) or may be compound(s) having a negative dielectric anisotropy ($\Delta\varepsilon$).

The liquid crystal composition according to the present invention may contain one or two or more compounds in at least one of the categories of nonpolar compounds represented by general formula (II) and compounds having a negative dielectric anisotropy ($\Delta\varepsilon$) represented by general formula (II) or may contain one or two or more nonpolar compounds represented by general formula (II) and one or two or more compounds having a negative dielectric anisotropy ($\Delta\varepsilon$) represented by general formula (II).

It is particularly preferred that the liquid crystal composition according to the present invention contain one or two or more of at least nonpolar compounds represented by general formula (II). This is because nonpolar compounds represented by general formula (II) are highly effective in reducing the rotational viscosity ($\gamma_1$) of the liquid crystal composition, thereby helping improve the response time of the liquid crystal composition.

It should be noted that the dielectric anisotropy ($\Delta\varepsilon$) of a compound of interest herein is a value given as a measured dielectric anisotropy at 20° C. of a dielectrically substantially neutral ($\Delta\varepsilon$ is in the range of −2 or more and 2 or less) base composition with the compound of interest therein minus that of the base composition without the compound of interest.

Preferred minimum percentages of compound(s) C, represented by general formula (II), are 1% by mass, 3% by mass, 5% by mass, 7% by mass, 10% by mass, 12% by mass, 15% by mass, 20% by mass, 25% by mass, 25.5% by mass, and 30% by mass of the entire liquid crystal composition according to the present invention. Preferred maximum percentages of compound(s) C, represented by general formula (I), are 60% by mass, 55% by mass, 50% by mass, 45% by mass, 40% by mass, 38% by mass, 35% by mass, and 33% by mass.

The preferred range for the percentage of compound(s) C, represented by general formula (II), can be determined by combining the above maxima and minima. Setting the percentage of above-described compound(s) C, represented by general formula (II), within a range determined by combining preferred maximum and minimum percentages helps lower the rotational viscosity ($\gamma_1$) of the liquid crystal composition, expand the range of temperatures in which the composition exhibits the nematic phase, and improve storage at low temperatures.

<Nonpolar Compound(s) Represented by General Formula (II)>

Preferably, compound(s) C, represented by general formula (II), in the liquid crystal composition according to the present invention is one or two or more compounds selected from the group consisting of the compounds represented by general formulae (II-NU-01), (II-NU-02), (II-NU-03), (II-NU-04), (II-NU-05), and (II-NU-06) below.

[Chem. 53]

$R^{IINU11}$—⬡—⬡—$R^{IINU12}$ (II-NU-01)

$R^{IINU11}$—⬡—⬢—$R^{IINU12}$ (II-NU-02)

$R^{IINU11}$—⬢—⬢—$R^{IINU12}$ (II-NU-03)

$R^{IINU11}$—⬡—⬡—⬢—$R^{IINU12}$ (II-NU-04)

$R^{IINU11}$—⬡—⬢—⬢—$R^{IINU12}$ (II-NU-05)

$R^{IINU11}$—⬢—⬢(F)—⬢—$R^{IINU12}$ (II-NU-06)

In each formula above, $R^{IINU11}$ and $R^{IINU12}$ each independently represent a C1 to C10 alkyl group, optionally with one —CH$_2$— in the alkyl group, or each of nonadjacent two or more —CH$_2$-s in the alkyl group independently, substituted by —CH=CH—, —C≡C—, —O—, —CO—, —COO—, or —OCO— unless oxygen atoms come consecutively next to each other, optionally with one or two or more hydrogen atoms in the alkyl group substituted with a halogen atom.

In each formula, however, at least one of $R^{IINU11}$ or $R^{IINU12}$ represents a C2 to C10 alkenyl group.

The compounds represented by general formulae (II-NU-01) to (II-NU-06) are nonpolar compounds; they are compounds dielectrically substantially neutral at 20° C., specifically having a dielectric anisotropy (Δε) at 20° C. of −2 or more and 2 or less.

In each of general formulae (II-NU-01) to (II-NU-06), it is preferred that at least one of $R^{IINU11}$ or $R^{IINU12}$ represent a C2 to C8 alkenyl group, preferably a C2 to C5 alkenyl group, preferably a C2 or C3 alkenyl group.

It is particularly preferred that $R^{IINU11}$ be a C2 to C8 alkenyl group, preferably a C2 to C5 alkenyl group, preferably a C2 or C3 alkenyl group, preferably a C2 alkenyl group.

Preferably, $R^{IINU11}$ represents a group selected from the group consisting of formulae (R1) to (R5) below. More preferably, $R^{IINU11}$ represents formula (R1) or (R2), even more preferably formula (R1), because in those cases the compound is more effective in reducing the rotational viscosity ($\gamma_1$) of the liquid crystal composition.

[Chem. 54]

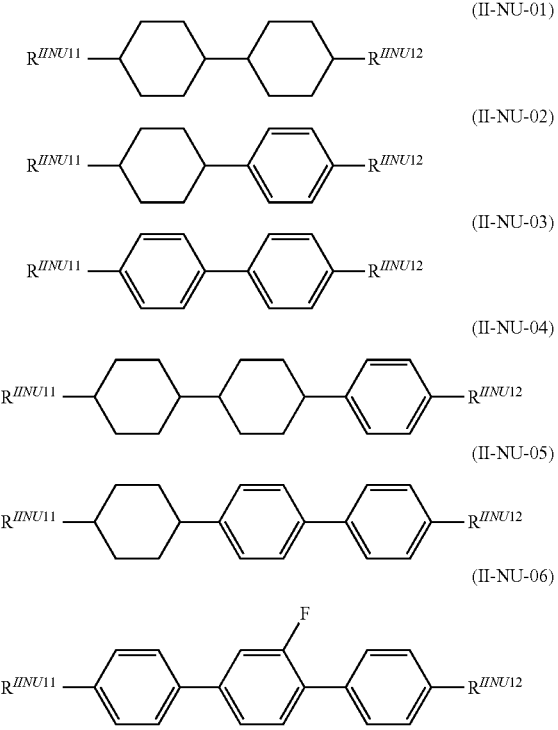

(R1)
(R2)
(R3)
(R4)
(R5)
(R6)

The black dot in each formula represents a carbon atom in the ring structure.

It is, furthermore, preferred that $R^{IINU12}$ represent a C1 to C8 alkyl group or a C1 to C8 alkoxy group, a C1 to C5 alkyl group in particular, more preferably a C1 to C3 alkyl group.

$R^{IINU11}$ and $R^{IINU12}$ may each independently have one or two or more hydrogen atoms in the group substituted with a halogen atom or may not. For dielectric anisotropy reasons, however, it is preferred that they do not. The halogen atom can be, for example, a fluorine or chlorine atom.

Preferably, the minimum percentage of the compound(s) represented by any of general formulae (II-NU-01) to (II-NU-06) is 1% by mass, 5% by mass, 10% by mass, 15% by mass, 20% by mass, 25% by mass, 25.5% by mass, or 30% by mass of the entire liquid crystal composition according to the present invention. Preferably, the maximum percentage of the compound(s) represented by any of general formulae (II-NU-01) to (II-NU-06) is 50% by mass, 45% by mass, 40% by mass, or 35% by mass of the entire liquid crystal composition according to the present invention.

The specific range of preferred percentages of the compound(s) represented by any of general formulae (II-NU-01) to (II-NU-06) can be determined as needed by combining the above maxima and minima. Of such ranges, the percentage is in the range of 5% to 50% by mass, in the range of 20% to 40% by mass, or in the range of 30% to 35% by mass of the entire liquid crystal composition according to the present invention in particular. Setting the percentage of the compound(s) represented by general formulae (II-NU-01) to (II-NU-06) within any of these ranges helps accelerate the response time of the liquid crystal composition because it helps reduce the rotational viscosity ($\gamma_1$) of the liquid crystal composition while maintaining the nematic-isotropic liquid phase transition temperature ($T_{ni}$).

Preferably, the compound(s) represented by general formula (II) above in the liquid crystal composition according to the present invention is one or two or more selected from the group consisting of the compounds represented by general formulae (II-NU-01A), (II-NU-02A), (II-NU-03A), (II-NU-04A), and (II-NU-05A) below.

[Chem. 55]

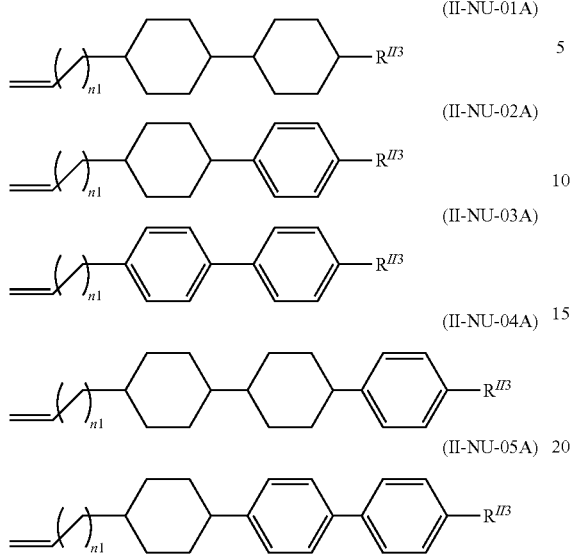

(In each formula above, $R^{II3}$ at each occurrence independently represents a C1 to C8 alkyl group, optionally with one —CH$_2$— in the alkyl group, or nonadjacent two or more —CH$_2$-s in the alkyl group, substituted with —CH=CH—, —C≡C—, —O—, —CO—, —COO—, or —OCO— unless oxygen atoms come consecutively next to each other, optionally with one or two or more hydrogen atoms in the alkyl group substituted with a halogen atom.

n1 at each occurrence independently represents an integer of 0 to 6.)

In general formulae (II-NU-01A) to (II-NU-05A), n1 at each occurrence independently represents an integer of 0 to 6. It is particularly preferred that n1 represent any integer of 0, 1, 2, 3, or 4, more preferably any integer of 0, 1, or 2. If accelerated response time is a priority, it is particularly preferred that n1 be 0.

In general formulae (II-NU-01A) to (II-NU-05A), it is preferred that $R^{II3}$ at each occurrence independently represent a C1 to C5 alkyl group, more preferably a C1 to C3 alkyl group. This is because this makes the compound more advantageous for accelerating the response time of the liquid crystal composition.

$R^{II3}$ may have one or two or more hydrogen atoms in the group substituted with a halogen atom or may not. For dielectric anisotropy reasons, however, it is preferred that it do not. The halogen atom can be, for example, a fluorine or chlorine atom.

Preferably, the percentage of the compound(s) represented by any of general formulae (II-NU-01A) to (II-NU-05A) is in the range of 1% to 50% by mass, in the range of 10% to 40% by mass, or in the range of 20% to 30% by mass of the entire liquid crystal composition so that the compound(s) will produce its effect of accelerating the response time of the liquid crystal composition.

Preferably, the liquid crystal composition according to the present invention contains one or two or more compounds in at least one of the categories of the compounds represented by general formula (II-NU-01A) and those represented by general formula (II-NU-04A) to combine a high speed with high reliability. It is particularly preferred that the liquid crystal composition contain one or two or more compounds represented by general formula (II-NU-01A).

Preferably, the liquid crystal composition according to the present invention contains one or two or more compounds represented by general formula (II-NU-01A$_1$). This is because such compounds, having low viscosity or low rotational viscosity, contributes greatly to both characteristics of improved reliability and improved response time.

[Chem. 56]

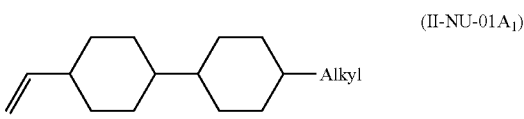

In the formula, Alkyl represents a C1 to C8 alkyl group.

It is particularly preferred that Alkyl, in general formula (II-NU-01A$_1$), be a C1 to C5 alkyl group, a C1 to C3 alkyl group, a C2 or C3 alkyl group, or a C3 alkyl group because in those cases the compound(s) is highly effective in both characteristics improvements, improved reliability and improved response time.

Preferably, the percentage of the compound(s) represented by general formula (II-NU-01A$_1$) is in the range of 0% to 50% by mass, in the range of 10% to 40% by mass, or in the range of 20% to 30% by mass of the entire liquid crystal composition according to the present invention. Setting the percentage of the compound(s) represented by general formula (II-NU-01A$_1$) within any of these ranges helps lower the rotational viscosity ($\gamma_1$) of the liquid crystal composition, expand the range of temperatures in which the composition exhibits the nematic phase, and improve storage at low temperatures.

Specific examples of compounds represented by general formula (II-NU-01A$_1$) include the compounds represented by formulae (II-NU-01A$_{11}$) to (II-NU-01A$_{14}$) below. Of these, the compound represented by formula (II-NU-01A$_{12}$) is particularly suitable for use because it acts better in accelerating the response time.

[Chem. 57]

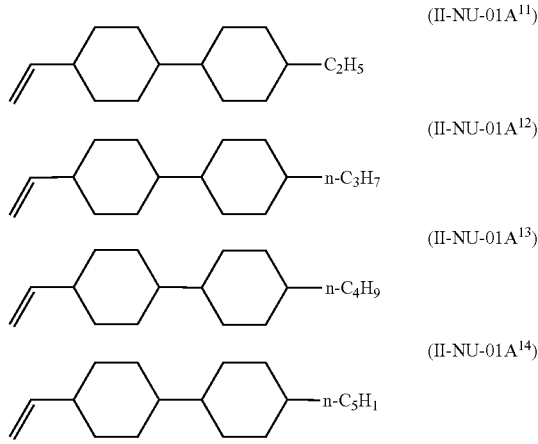

<Compound(s) Having a Negative Dielectric Anisotropy (Δε) Represented by General Formula (II)>

Preferably, compound(s) C, represented by general formula (II), in the liquid crystal composition according to the present invention is one or two or more compounds selected from the group consisting of the compounds represented by general formulae (II-N-01), (II-N-02), (II-N-03), (II-N-04), and (II-N-05) below.

[Chem. 58]

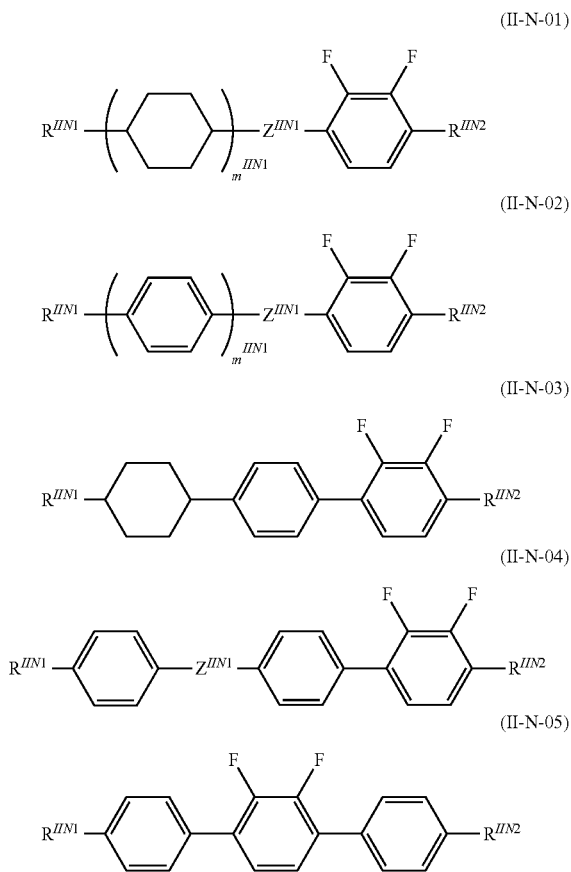

(In the formulae, $R^{IIN1}$ and $R^{IIN2}$ each independently represent a C1 to C10 alkyl group, optionally with one —CH$_2$— in the alkyl group, or each of nonadjacent two or more —CH$_2$-s in the alkyl group independently, substituted by —CH=CH—, —C≡C—, —O—, —CO—, —COO—, or —OCO— unless oxygen atoms come consecutively next to each other, optionally with one or two or more hydrogen atoms in the alkyl group substituted with a halogen atom.

In each formula, however, at least one of $R^{IIN1}$ or $R^{IIN2}$ represents a C$_2$ to C$_{10}$ alkenyl group.

$Z^{IIN1}$ at each occurrence independently represents a single bond, —CH$_2$CH$_2$—, —OCH$_2$—, —CH$_2$O—, —COO—, —OCO—, —OCF$_2$—, —CF$_2$O—, —CH=CH—, —CF=CF—, or —C≡C—.

$m^{IIN1}$ at each occurrence independently represents 1 or 2.

Any compound represented by general formula (I), however, is excluded.)

The compounds represented by general formulae (II-N-01) to (II-N-05) are compounds having a negative dielectric anisotropy (Δε) and are alkenyl compounds because they have alkenyl group(s). The term compound having a negative dielectric anisotropy (Δε) refers to a compound having a dielectric anisotropy (Δε) with a negative sign and an absolute value greater than 2. It is particularly preferred that the absolute Δε be 3 or greater.

In general formulae (II-N-01) to (II-N-05), it is preferred that at least one of $R^{IIN1}$ or $R^{IIN2}$ represent a C2 to C8 alkenyl group, preferably a C2 to C5 alkenyl group, preferably a C2 or C3 alkenyl group. It is particularly preferred that $R^{IIN1}$ be a C2 to C8 alkenyl group, preferably a C2 to C5 alkenyl group, preferably a C2 or C3 alkenyl group, preferably a C2 alkenyl group Preferably, $R^{IIN1}$ represents a group selected from the group consisting of formulae (R1) to (R5) below. More preferably, $R^{IIN1}$ represents formula (R1) or (R2), even more preferably formula (R1), because in those cases the compound is more effective in reducing the rotational viscosity ($\gamma_1$) of the liquid crystal composition.

[Chem. 59]

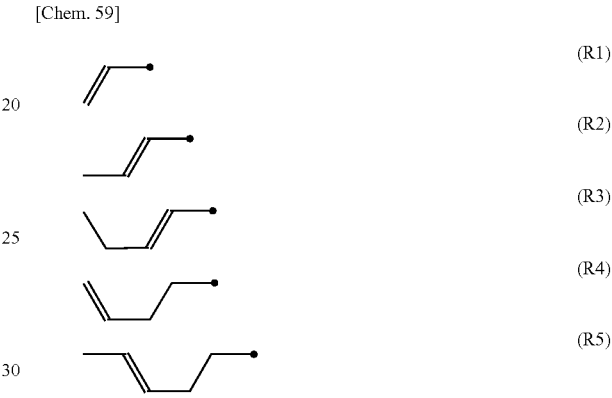

(The black dot in each formula represents a carbon atom in the ring structure.)

Preferably, $R^{IIN2}$ represents a C1 to C8 alkyl group or a C1 to C8 alkoxy group, more preferably a C1 to C5 alkyl group or a C1 to C4 alkoxy group, even more preferably a C1 to C4 alkoxy group.

To make the absolute Δε greater, furthermore, it is preferred that $R^{IIN2}$ represent a C1 to C8 alkoxy group or a C2 to C8 alkenyloxy group.

$R^{IIN1}$ and $R^{IIN2}$ may each independently have one or two or more hydrogen atoms in the group substituted with a halogen atom or may not. For dielectric anisotropy reasons, however, it is preferred that they do not. The halogen atom can be, for example, a fluorine or chlorine atom.

Preferably, $Z^{IIN1}$ is a single bond, —CH$_2$CH$_2$—, —OCH$_2$—, or —CH$_2$O—, more preferably a single bond or —CH$_2$O—. If $m^{IIN1}$ is 1, it is preferred that $Z^{IIN1}$ is a single bond. If $m^{IIN1}$ is 2, it is preferred that $Z^{IIN1}$ is —CH$_2$CH$_2$— or —CH$_2$O—.

In general formulae (II-N-01) to (II-N-05), the fluorine atoms may be substituted with chlorine atoms, which are in the same group of halogens. The percentage of chlorine-substituted compounds, however, should be as small as possible. Preferably, the liquid crystal composition contains no such compound.

In general formulae (II-N-01) to (II-N-05), one or two or more hydrogen atoms on the rings may be further substituted with a fluorine or chlorine atom. The percentage of chlorine-substituted compounds, however, should be as small as possible. Preferably, the liquid crystal composition contains no such compound.

Of the compounds represented by general formulae (II-N-01) to (II-N-05), those represented by general formula (II-N-01) are particularly preferred as they can have large Δn and Δε despite their low rotational viscosity ($\gamma_1$). With their potential to have large Δn and Δε, the compounds help enhance the advantages of accelerated response time and lower voltage requirement of the liquid crystal composition.

Preferably, the minimum percentage of the compound(s) represented by any of general formulae (II-N-01) to (II-N-05) is 0% by mass, 3% by mass, or 5% by mass of the entire liquid crystal composition according to the present invention. Preferably, the percentage of the compound(s) represented by any of general formulae (II-N-01) to (II-N-05) is 15% by mass, 10% by mass, or 7% by mass of the entire liquid crystal composition according to the present invention.

The preferred range for the percentage of the compound(s) represented by any of general formulae (II-N-01) to (II-N-05) can be determined as needed by combining the above maxima and minima. Of such ranges, the percentage is in the range of 0% to 15% by mass, in the range of 3% to 10% by mass, or in the range of 5% to 7% by mass of the entire liquid crystal composition according to the present invention in particular.

Setting the percentage of the compound(s) represented by general formulae (II-N-01) to (II-N-05) within any of these ranges helps improve the nematic-isotropic liquid phase transition temperature ($T_{ni}$) and accelerate the response time of the liquid crystal composition.

The liquid crystal composition in the present invention, furthermore, may further contain one or two or more compounds represented by general formula (II-N-06).

[Chem. 60]

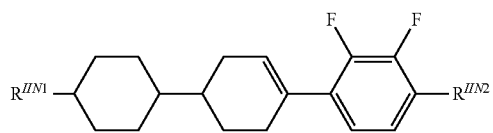

(II-N-06)

(In the formula, $R^{IIN1}$ and $R^{IIN2}$ express the same meaning as stated above.)

Minimum total percentages, to the entire liquid crystal composition according to the present invention, of the compound(s) selected from the group consisting of the compounds represented by general formulae (II-NU-01), (II-NU-02), (II-NU-03), (II-NU-04), (II-NU-05), and (II-NU-06) and the compound(s) selected from the group consisting of the compounds represented by general formulae (II-N-01), (II-N-02), (II-N-03), (II-N-04), and (II-N-05) can be the same as those of the compound(s) represented by general formula (II). Maximum total percentages can be the same as those the compound(s) represented by general formula (II).

1-4. Compound(s) D, Represented by General Formula (N-1), (N-2), or (N-3)

The liquid crystal composition according to the present invention can further contain one compound D, selected from the group consisting of the compounds represented by general formulae (N-1), (N-2), and (N-3), or two or more compounds D. In general formulae (N-1), (N-2), and (N-3), any compound represented by general formula (Y), (P), or (II) is excluded, in general formulae (N-2) and (N-3), any compound represented by general formula (N-1) is excluded, and in general formula (N-3), any compound represented by general formula (N-2) is excluded.

[Chem. 61]

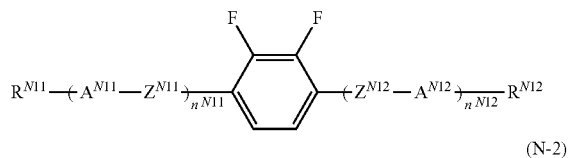

(N-1)

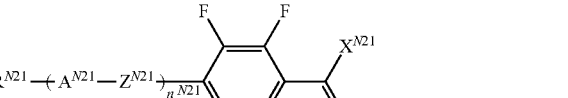

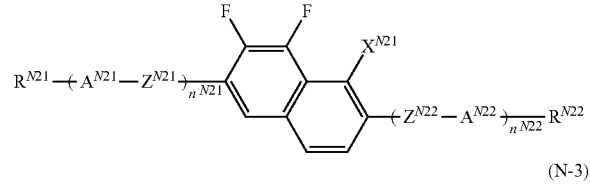

(N-2)

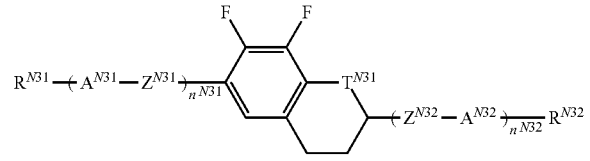

(N-3)

In the formulae, $R^{N11}$, $R^{N12}$, $R^{N21}$, $R^{N22}$, $R^{N31}$, and $R^{N32}$ each independently represent a C1 to C8 alkyl group, optionally with one —$CH_2$— in the alkyl group, or each of nonadjacent two or more —$CH_2$-s in the alkyl group independently, substituted by —CH=CH—, —C≡C—, —O—, —CO—, —COO—, or —OCO— unless oxygen atoms come consecutively next to each other.

$A^{N11}$, $A^{N12}$, $A^{N21}$, $A^{N22}$, $A^{N31}$, and $A^{N32}$ each independently represent a group selected from the group consisting of:

(a) a 1,4-cyclohexylene group (One —$CH_2$— or two or more nonadjacent —$CH_2$—S present in the group may be replaced by —O— unless oxygen atoms come consecutively next to each other.);

(b) a 1,4-phenylene group (One or two or more —CH=s present in the group may be replaced by —N=·); and (c) a naphthalene-2,6-diyl, 1,2,3,4-tetrahydronaphthalene-2,6-diyl, or decahydronaphthalene-2,6-diyl group (One or two or more —CH=s present in these groups may be replaced by —N=.), optionally with one hydrogen atom in the group (a), (b), or (c), or each of two or more independently, substituted with a cyano group or a halogen atom.

$Z^{N11}$, $Z^{N12}$, $Z^{N21}$, $Z^{N22}$, $Z^{N31}$, and $Z^{N32}$ each independently represent a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—.

$X^{N21}$ represents a hydrogen atom or a halogen atom, preferably a fluorine atom.

$T^{N31}$ represents —$CH_2$— or an oxygen atom.

$n^{N11}$, $n^{N12}$, $n^{N21}$, $n^{N22}$, $n^{N31}$, and $n^{N32}$ each independently represent an integer of 0, 1, 2, or 3, with the proviso that $n^{N11}+n^{N12}$, $n^{N21}+n^{N22}$, and $n^{N31}+n^{N32}$ each independently represent 1, 2, or 3.

If there are multiple $A^{N11}$s, multiple $A^{N12}$s, multiple $A^{N21}$s, multiple $A^{N22}$s, multiple $A^{N31}$s, and multiple $A^{N32}$s, the referents may be identical or different.

If there are multiple $Z^{N11}$s, multiple $Z^{N12}$s, multiple $Z^{N21}$s, multiple $Z^{N22}$s, multiple $Z^{N31}$s, and multiple $Z^{N32}$s, the referents may be identical or different.

The compounds represented by general formulae (N-1), (N-2), and (N-3) are compounds that exhibit a negative dielectric anisotropy but not are compounds represented by general formula (I) or (II), having a Δε with a negative sign and an absolute value greater than 2. Of the compounds represented by general formulae (N-1), (N-2), and (N-3), those having an absolute Δε of 3 or greater are particularly preferred.

Preferably, in general formulae (N-1), (N-2), and (N-3), each of $R^{N11}$, $R^{N12}$, $R^{N21}$, $R^{N22}$, $R^{N31}$, and $R^{N32}$ is independently a C1 to C8 alkyl group, a C1 to C8 alkoxy group, or a C2 to C8 alkenyl group, preferably a C1 to C5 alkyl group, a C1 to C5 alkoxy group, or a C2 to C5 alkenyl group, preferably a C1 to C5 alkyl group, more preferably a C2 to C5 alkyl group.

If $R^{N11}$, $R^{N12}$, $R^{N21}$, $R^{N22}$, $R^{N31}$, and $R^{N32}$ each bind with a phenyl ring (aromatic) structure, furthermore, it is preferred that the referents be linear C1 to C5 alkyl groups or linear C1 to C4 alkoxy groups. If they each bind with a saturated ring structure, such as cyclohexane, pyran, or dioxane, it is preferred that the referents be linear C1 to C5 alkyl group or linear C1 to C4 alkoxy groups. To stabilize the nematic phase, it is preferred that the total number of carbon atoms and any oxygen atom be 5 or smaller, preferably in a linear structure.

$R^{N11}$, $R^{N12}$, $R^{N21}$, $R^{N22}$, $R^{N31}$, and $R^{N32}$ may each independently have one or two or more hydrogen atoms in the group substituted with a halogen atom or may not. For dielectric anisotropy reasons, however, it is preferred that they do not. The halogen atom can be, for example, a fluorine or chlorine atom.

Preferably, each of $A^{N11}$, $A^{N12}$, $A^{N21}$, $A^{N22}$, $A^{N31}$, and $A^{N32}$ is independently, if a large Δn is needed, an aromatic. For improved response time, it is preferred that each of them be an aliphatic, preferably representing a trans-1,4-cyclohexylene, 1,4-phenylene, 2-fluoro-1,4-phenylene, 3-fluoro-1,4-phenylene, 3,5-difluoro-1,4-phenylene, 2,3-difluoro-1,4-phenylene, 1,4-cyclohexenylene, 1,4-bicyclo[2.2.2]octylene, piperidine-1,4-diyl, naphthalene-2,6-diyl, decahydronaphthalene-2,6-diyl, or 1,2,3,4-tetrahydronaphthalene-2,6-diyl group, more preferably any of the following structures:

[Chem. 62]

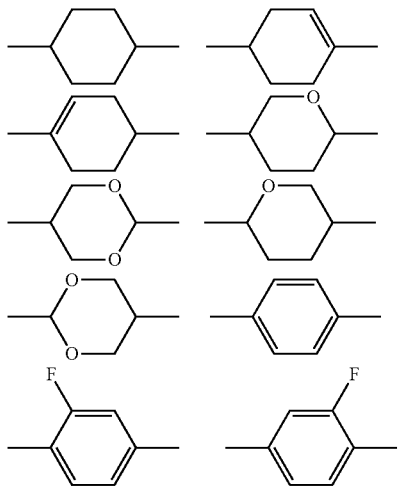

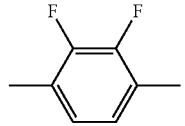

even more preferably a trans-1,4-cyclohexylene, 1,4-cyclohexenylene, or 1,4-phenylene group.

Preferably, $Z^{N11}$, $Z^{N12}$, $Z^{N21}$, $Z^{N22}$, $Z^{N31}$, and $Z^{N32}$ each independently represent —CH$_2$O—, —CF$_2$O—, —CH$_2$CH$_2$—, —CF$_2$CF$_2$—, or a single bond. More preferably, each of them is —CH$_2$O—, —CH$_2$CH$_2$—, or a single bond, —CH$_2$O— or a single bond in particular.

Preferably, $X^{N21}$ is a fluorine atom.
Preferably, $T^{N31}$ is an oxygen atom.
Preferably, $n^{N11}+n^{N12}$, $n^{N21}+n^{N22}$, and $n^{N31}+n^{N32}$ are 1 or 2. The combination of 1 for $n^{N11}$ and 0 for $n^{N12}$, that of 2 for $n^{N11}$ and 0 for $n^{N12}$, that of 1 for $n^{N11}$ and 1 for $n^{N12}$, that of 2 for $n^{N11}$ and 1 for $n^{N12}$, that of 1 for $n^{N21}$ and 0 for $n^{N22}$, that of 2 for $n^{N21}$ and 0 for $n^{N22}$, that of 1 for $n^{N31}$ and 0 for $n^{N32}$, and that of 2 for $n^{N31}$ and 0 for $n^{N32}$ are preferred.

Preferably, the liquid crystal composition according to the present invention contains one or two or more compounds represented by general formula (N-1). It is, furthermore, preferred that the compound(s) represented by general formula (N-1) be one or two or more selected from the group consisting of the compounds represented by general formulae (N-01), (N-02), (N-03), (N-04), and (N-05), excluding any compound represented by general formula (Y), (P), or (II).

[Chem. 63]

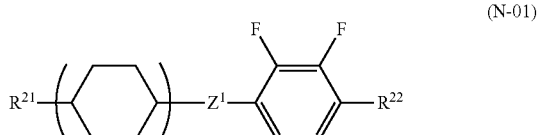
(N-01)

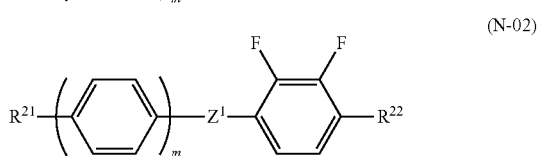
(N-02)

(N-03)

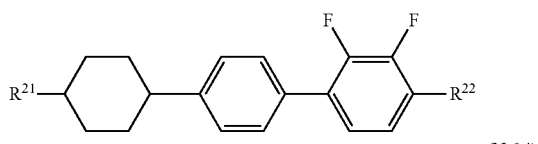
(N-04)

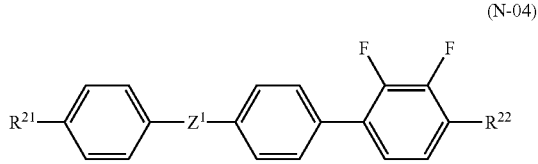
(N-05)

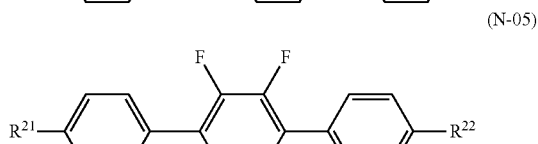

In each formula above, $R^{21}$ and $R^{22}$ each independently represent a C1 to C8 alkyl group, optionally with one —$CH_2$— in the alkyl group, or nonadjacent two or more —$CH_2$-s in the alkyl group, substituted by —C≡C—, —O—, —CO—, —COO—, or —OCO— unless oxygen atoms are consecutively next to each other, optionally with one or two or more hydrogen atoms in the alkyl group substituted with a halogen atom.

$Z^1$ at each occurrence independently represents a single bond, —$CH_2CH_2$—, —$OCH_2$—, —$CH_2O$—, —COO—, —OCO—, —$OCF_2$—, —$CF_2O$—, —CH=CH—, —CF=CF—, or —C≡C—.

m at each occurrence independently represents 1 or 2.

The compounds represented by general formulae (N-01) to (N-05) are non-alkenyl compounds having a dielectric anisotropy (Δε) with a negative sign and an absolute value greater than 2 at 20° C. Of the compounds represented by general formulae (N-01) to (N-05), those having an absolute Δε of 3 or greater are particularly preferred.

Preferably, $R^{21}$ is a C1 to C8 alkyl group, more preferably a C1 to C5 alkyl group, even more preferably a C1 to C4 alkyl group. If $Z^1$ represents anything other than a single bond, however, it is preferred that $R^{21}$ be a C1 to C3 alkyl group.

One or two or more hydrogen atoms in the alkyl group represented by $R^{21}$ may be substituted with a halogen atom or may not. For dielectric anisotropy reasons, however, it is preferred that they be not. Preferably, the halogen atom is a fluorine or chlorine atom, more preferably a fluorine atom.

Preferably, $R^{22}$ is a C1 to C8 alkyl group or a C1 to C8 alkoxy group. It is particularly preferred that $R^{22}$ represent a C1 to C8 alkoxy group because this helps increase the absolute Δε. More preferably, $R^{22}$ is a C1 to C4 alkoxy group. One or two or more hydrogen atoms in the alkyl or alkoxy group may be substituted with a halogen atom or may not. For dielectric anisotropy reasons, however, it is preferred that they be not. Preferably, the halogen atom is a fluorine or chlorine atom, more preferably a fluorine atom.

Preferably, $Z^1$, which at each occurrence independently represents a single bond, —$CH_2CH_2$—, —$OCH_2$—, —$CH_2O$—, —COO—, —OCO—, —$OCF_2$—, —$CF_2O$—, —CH=CH—, —CF=CF—, or —C≡C—, is a single bond, —$CH_2CH_2$—, —$OCH_2$—, —$CH_2O$—, more preferably a single bond or —$CH_2O$—. If m is 1, it is preferred that $Z^1$ be a single bond. If m is 2, it is preferred that $Z^1$ be —$CH_2CH_2$— or —$CH_2O$—.

In the compound(s) represented by any of general formulae (N-01) to (N-05), the fluorine atoms may be substituted with chlorine atoms, which are in the same group of halogens. The percentage of chlorine-substituted compounds should be as small as possible. Preferably, the liquid crystal composition contains no such compound.

In the compound(s) represented by any of general formulae (N-01) to (N-05), one or two or more hydrogen atoms on the rings may be further substituted with a fluorine or chlorine atom. The percentage of chlorine-substituted compounds, however, should be as small as possible. Preferably, the liquid crystal composition contains no such compound.

Preferably, the compound(s) represented by general formula (N-01) in the liquid crystal composition according to the present invention is one or two or more selected from the group of compounds represented by general formulae (N-01-1) and (N-01-2) below.

[Chem. 64]

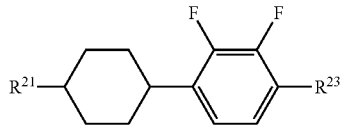

(N-01-1)

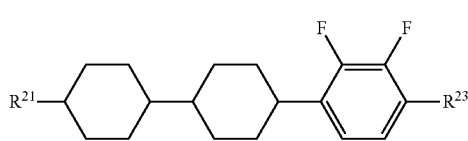

(N-01-2)

In the formulae, $R^{21}$ expresses the same meaning as stated above. $R^{23}$ at each occurrence independently represents a C1 to C4 alkoxy group, optionally with one or two or more hydrogen atoms in the alkoxy group substituted with a fluorine atom. Any compound represented by general formula (Y), (P), or (II) is excluded.

It is, furthermore, the compound(s) represented by general formula (N-01) in the liquid crystal composition according to the present invention be one or two or more selected from the group of compounds represented by general formulae (N-01-3) and (N-01-4) below.

[Chem. 65]

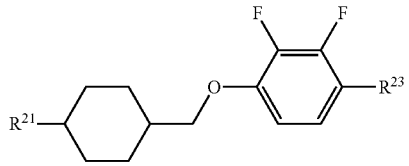

(N-01-3)

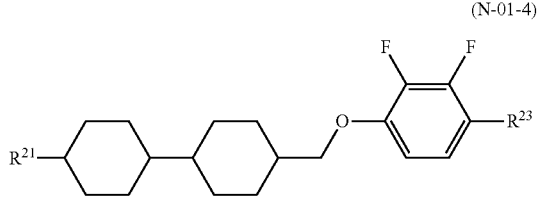

(N-01-4)

(In the formulae, $R^{21}$ expresses the same meaning as stated above. $R^{23}$ at each occurrence independently represents a C1 to C4 alkoxy group, optionally with one or two or more hydrogen atoms in the alkoxy group substituted with a fluorine atom. Any compound represented by general formula (Y), (P), or (II) is excluded.

It is particularly preferred that the liquid crystal composition according to the present invention contain one or two or more compounds in at least one of the categories of the compounds represented by general formula (N-01-3) and those represented by general formula (N-01-4). This is because this helps increase the Δε of the liquid crystal composition.

In general formulae (N-01-3) and (N-01-4), preferred forms of $R^{21}$ are as stated above. Preferably, $R^{23}$, which at each occurrence independently represents a $C_1$ to $C_4$ alkoxy group, represents a C1 to C3 alkoxy, more preferably a C1 or C2 alkoxy.

Specific examples of compounds represented by general formula (N-01-3) include the compounds represented by formulae (N-01-3a) to (N-01-3e) below. Of these, the compound represented by formula (N-01-3b) is particularly preferred for use.

[Chem. 66]

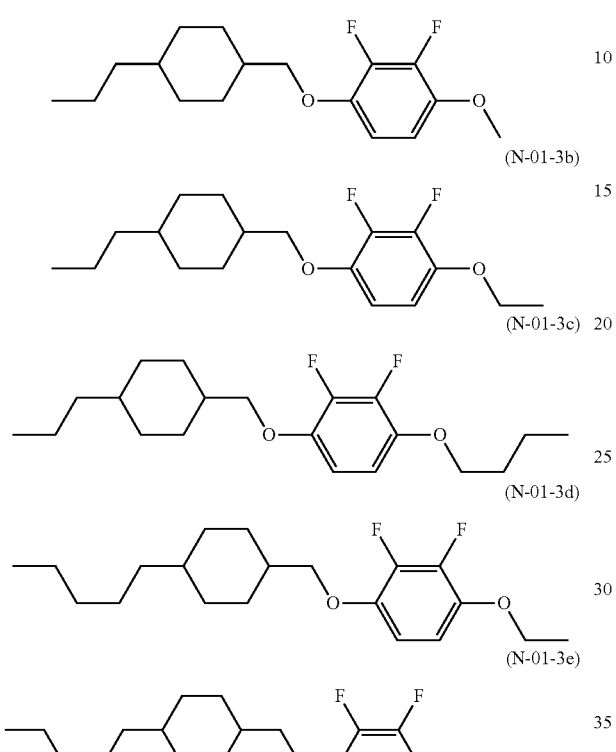

Specific examples of compounds represented by general formula (N-01-4) include the compounds represented by formulae (N-01-4a) to (N-01-4f) below. Of these, the compound represented by formula (N-01-4d) is particularly preferred for use.

[Chem. 67]

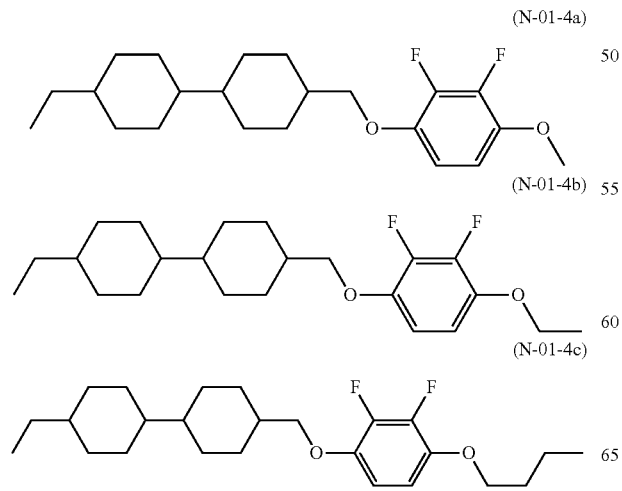

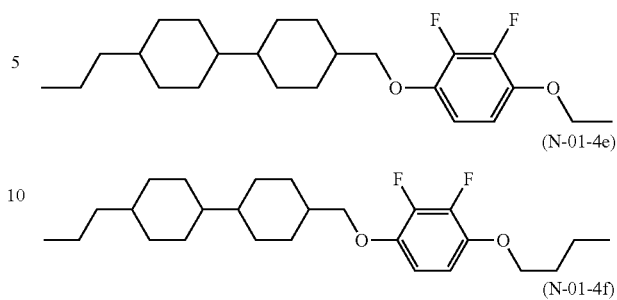

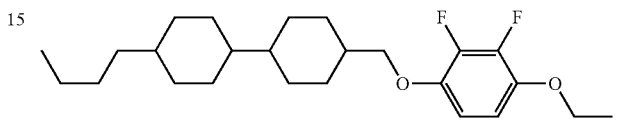

Preferably, the liquid crystal composition according to the present invention contains the compound represented by formula (N-01-3b), the compound represented by formula (N-01-4d), or both.

Preferably, the compound(s) represented by general formula (N-02) in the liquid crystal composition according to the present invention is one or two or more selected from the group consisting of the compounds represented by general formulae (N-02-1) to (N-02-3) below.

[Chem. 68]

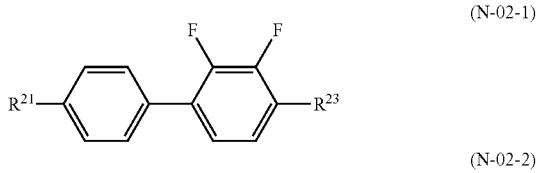

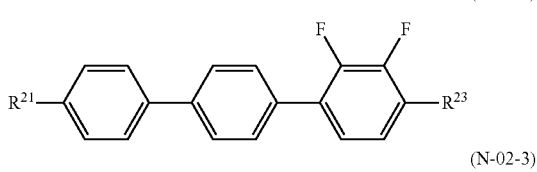

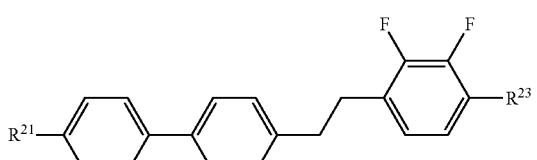

In the formulae, $R^{21}$ expresses the same meaning as stated above. $R^{23}$ at each occurrence independently represents a C1 to C4 alkoxy group, optionally with one or two or more hydrogen atoms in the alkoxy group substituted with a fluorine atom. Any compound represented by general formula (II) is excluded.)

Preferably, the liquid crystal composition according to the present invention contains compound(s) in at least one of the categories of the compounds represented by general formula (N-02-1) and those represented by general formula (N-02-3).

Preferably, the compound(s) represented by general formula (N-03) in the liquid crystal composition according to the present invention is one or two or more of compounds represented by general formula (N-03-1) below.

[Chem. 69]

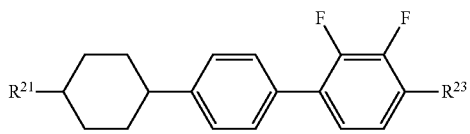

(N-03-1)

In the formulae, $R^{21}$ expresses the same meaning as stated above. $R^{23}$ represents a C1 to C4 alkoxy group, optionally with one or two or more hydrogen atoms in the alkoxy group substituted with a fluorine atom. Any compound represented by general formula (Y), (P), or (II) is excluded.

Preferably, the compound(s) represented by general formula (N-04) in the liquid crystal composition according to the present invention is one or two or more of compounds represented by general formula (N-04-1) below.

[Chem. 70]

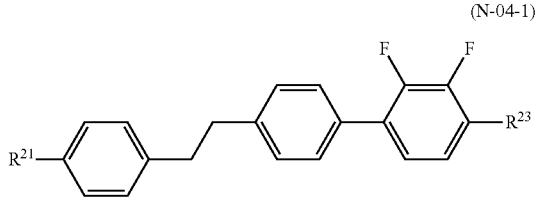

(N-04-1)

In the formulae, $R^{21}$ expresses the same meaning as stated above. $R^{23}$ represents a C1 to C4 alkoxy group, optionally with one or two or more hydrogen atoms in the alkoxy group substituted with a fluorine atom. Any compound represented by general formula (Y), (P), or (II) is excluded.

Preferably, the compound(s) represented by general formula (N-05) in the liquid crystal composition according to the present invention is one or two or more selected from the group consisting of the compounds represented by formulae (N-05-1) to (N-05-3) below.

[Chem. 71]

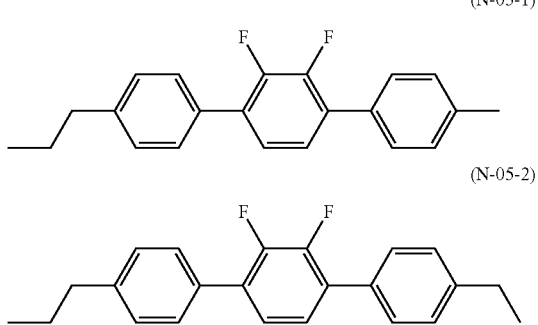

(N-05-1)

(N-05-2)

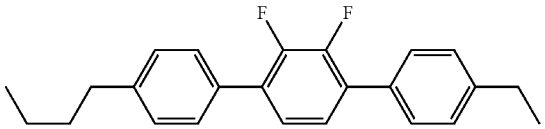

(N-05-3)

It is particularly preferred that the liquid crystal composition according to the present invention contain compound(s) represented by general formula (N-01-1), compound(s) represented by general formula (N-01-4), and compound(s) represented by general formula (N-02-1) at the same time.

It is particularly preferred that the liquid crystal composition according to the present invention contain compound(s) represented by general formula (N-01-1), compound(s) represented by general formula (N-01-4), and compound(s) represented by general formula (N-02-3) at the same time.

It is particularly preferred that the liquid crystal composition according to the present invention contain compound(s) represented by general formula (N-01-1), compound(s) represented by general formula (N-01-4), and compound(s) represented by general formula (N-03-1) at the same time.

It is particularly preferred that the liquid crystal composition according to the present invention contain compound(s) represented by general formula (N-01-1), compound(s) represented by general formula (N-01-4), and compound(s) represented by general formula (N-04-1) at the same time.

Preferred minimum percentages, to the entire liquid crystal composition according to the present invention, of compounds represented by general formula (N-01) are 0% by mass, 1% by mass, 5% by mass, 8% by mass, 10% by mass, 15% by mass, 20% by mass, 30% by mass, 40% by mass, 50% by mass, 55% by mass, 60% by mass, 65% by mass, 70% by mass, 75% by mass, and 80% by mass. Preferred maximum percentages are 95% by mass, 85% by mass, 75% by mass, 65% by mass, 55% by mass, 45% by mass, 35% by mass, 25% by mass, 20% by mass, 15% by mass, and 10% by mass.

Preferred minimum percentages, to the entire liquid crystal composition according to the present invention, of compounds represented by general formula (N-02) are 0% by mass, 1% by mass, 5% by mass, 10% by mass, 20% by mass, 30% by mass, 40% by mass, 50% by mass, 55% by mass, 60% by mass, 65% by mass, 70% by mass, 75% by mass, and 80% by mass. Preferred maximum percentages are 95% by mass, 85% by mass, 75% by mass, 65% by mass, 55% by mass, 45% by mass, 35% by mass, 25% by mass, 20% by mass, 15% by mass, and 10% by mass.

Preferred minimum percentages, to the entire liquid crystal composition according to the present invention, of compounds represented by general formula (N-03) are 0% by mass, 1% by mass, 5% by mass, 10% by mass, 20% by mass, 30% by mass, 40% by mass, 50% by mass, 55% by mass, 60% by mass, 65% by mass, 70% by mass, 75% by mass, and 80% by mass. Preferred maximum percentages are 95% by mass, 85% by mass, 75% by mass, 65% by mass, 55% by mass, 45% by mass, 35% by mass, 25% by mass, 20% by mass, 15% by mass, and 10% by mass.

Preferred minimum percentages, to the entire liquid crystal composition according to the present invention, of compounds represented by general formula (N-04) are 0% by mass, 1% by mass, 5% by mass, 10% by mass, 20% by mass, 30% by mass, 40% by mass, 50% by mass, 55% by mass, 60% by mass, 65% by mass, 70% by mass, 75% by mass, and 80% by mass. Preferred maximum percentages are 95% by mass, 85% by mass, 75% by mass, 65% by mass, 55% by mass, 45% by mass, 35% by mass, 25% by mass, 20% by mass, 15% by mass, and 10% by mass.

Preferred minimum percentages, to the entire liquid crystal composition according to the present invention, of compounds represented by general formula (N-05) are 0% by mass, 2% by mass, 5% by mass, 8% by mass, 10% by mass, 13% by mass, 15% by mass, 17% by mass, and 20% by mass. Preferred maximum percentages are 30% by mass, 28% by mass, 25% by mass, 23% by mass, 20% by mass, 18% by mass, 15% by mass, and 13% by mass.

The liquid crystal composition according to the present invention, furthermore, may further contain one or two or more compounds represented by general formula (N-06).

[Chem. 72]

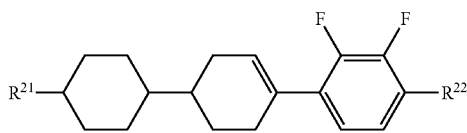

(N-06)

In the formula, $R^{21}$ and $R^{22}$ express the same meaning as stated above. Any compound represented by general formula (Y), (P), or (II) is excluded.

The compounds represented by general formula (N-06) are effective if the manufacturer wants to modify characteristics. In particular, they can be used to attain a large refractive-index anisotropy (Δn), a high nematic-isotropic liquid phase transition temperature ($T_m$), and a great Δε.

Preferred minimum percentages, to the entire liquid crystal composition according to the present invention, of compounds represented by general formula (N-06) are 0% by mass, 2% by mass, 5% by mass, 8% by mass, 10% by mass, 13% by mass, 15% by mass, 17% by mass, and 20% by mass. Preferred maximum percentages are 30% by mass, 28% by mass, 25% by mass, 23% by mass, 20% by mass, 18% by mass, 15% by mass, 13% by mass, 10% by mass, and 5% by mass.

The compound(s) represented by general formula (N-1) in the liquid crystal composition according to the present invention, furthermore, may be one or two or more of the compounds represented by general formulae (N-07-1) and (N-07-2) below.

[Chem. 73]

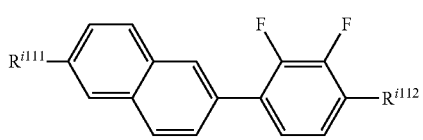

(N-07-1)

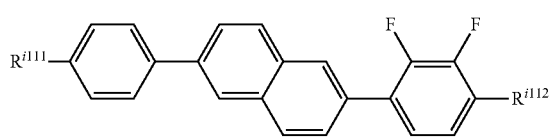

(N-07-2)

In the formulae, $R^{i111}$ and $R^{i112}$ express the same meaning as $R^{N11}$ and $R^{N12}$ in general formula (N-1). Any compound represented by general formula (Y), (P), or (II) is excluded.

The compounds represented by general formulae (N-07-1) and (N-07-2) are effective in improving the reactivity of the monomer(s) in particular; they help shorten the duration of UV irradiation when the monomer(s) is processed into polymer(s).

1-5. Compound(s) E, Represented by General Formula (L)

The liquid crystal composition according to the present invention may further contain one compound E, represented by general formula (L), or two or more compounds E.

[Chem. 74]

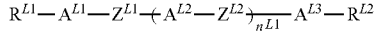

(L)

In the formula, $R^{L1}$ and $R^{L2}$ each independently represent a C1 to C8 alkyl group, optionally with one —CH$_2$— in the alkyl group, or each of nonadjacent two or more CH$_2$-s in the alkyl group independently, substituted by —CH=CH—, —C≡C—, —O—, —CO—, —COO—, or —OCO— unless oxygen atoms come consecutively next to each other, $A^{L1}$, $A^{L2}$, and $A^{L3}$ each independently represent a group selected from the group consisting of:

(a) a 1,4-cyclohexylene group (One —CH$_2$— or two or more nonadjacent —CH$_2$-s present in the group may be replaced by —O— unless oxygen atoms come consecutively next to each other.);

(b) a 1,4-phenylene group (One or two or more —CH=s present in the group may be replaced by —N=.); and (c) a naphthalene-2,6-diyl, 1,2,3,4-tetrahydronaphthalene-2,6-diyl, or decahydronaphthalene-2,6-diyl group (One or two or more —CH=s present in the group may be replaced by —N=.), optionally with one hydrogen atom in the group (a), (b), or (c), or each of two or more independently, substituted with a cyano group or a halogen atom, $Z^{L1}$ and $Z^{L2}$ each independently represent a single bond, —CH$_2$CH$_2$—, —(CH$_2$)$_4$—, —OCH$_2$—, —CH$_2$O—, —COO—, —OCO—, —OCF$_2$—, —CF$_2$O—, —CH=N—N=CH—, —CH=CH—, —CF=CF—, or —C≡C—, $n^{L1}$ represents 0, 1, 2, or 3, if $n^{L1}$ is 2 or 3 and if, therefore, there are multiple $A^{L2}$s, the multiple $A^{L2}$s may be identical or different, and if $n^{L1}$ is 2 or 3 and if, therefore, there are multiple $Z^{L3}$s, the multiple $Z^{L3}$s may be identical or different.

Any compound represented by general formula (Y), (P), (II), (N-1), (N-2), or (N-3) is excluded.

The compounds represented by general formula (L) are dielectrically substantially neutral compounds. Specifically, it is preferred that the compound(s) represented by general formula (L) have a dielectric anisotropy (Δε) at 20° C. of −2 or more and 2 or less.

Preferably, the compound(s) represented by general formula (L) in the liquid crystal composition according to the present invention is one or two or more selected from the group consisting of the compounds represented by general formulae (NU-01) to (NU-06) below.

[Chem. 75]

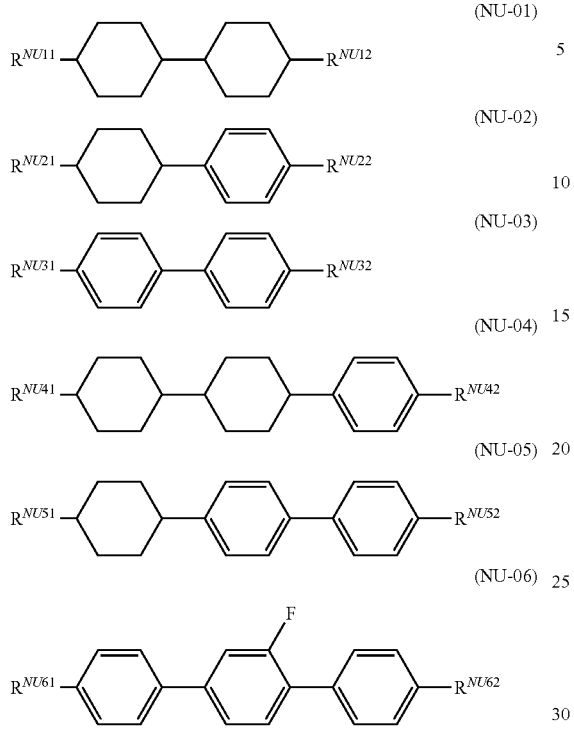

In the formulae, $R^{NU11}$, $R^{NU12}$, $R^{NU21}$, $R^{NU22}$, $R^{NU31}$, $R^{NU32}$, $R^{NU41}$, $R^{NU42}$, $R^{NU51}$, $R^{NU52}$, $R^{NU61}$, and $R^{NU62}$ each independently represent a C1 to C8 alkyl group, optionally with one —CH$_2$— in the group, or each of nonadjacent two or more —CH$_2$-s in the group independently, substituted by —C=C—, —C≡C—, —O—, —CO—, —COO—, or —OCO— unless oxygen atoms come consecutively next to each other. Any compound represented by general formula (Y), (P), (II), (N-1), (N-2), or (N-3) is excluded.

Preferably, in general formulae (NU-01) to (NU-06), each of $R^{NU11}$, $R^{NU12}$, $R^{NU21}$, $R^{NU22}$, $R^{NU31}$, $R^{NU32}$, $R^{NU41}$, $R^{NU42}$, $R^{NU51}$, $R^{NU52}$, $R^{NU61}$, and $R^{NU62}$ is independently a C1 to C8 alkyl or C1 to C8 alkoxy group, more preferably a C1 to C5 alkyl or C1 to C5 alkoxy group, even more preferably a C1 to C5 alkyl group.

Preferably, the liquid crystal composition according to the present invention contains one or two or more of at least the compounds represented by general formula (NU-01).

Preferably, the liquid crystal composition according to the present invention contains one or two or more of at least the compounds represented by general formula (NU-04).

Preferably, the liquid crystal composition according to the present invention contains one or two or more of at least the compounds represented by general formula (NU-06).

Preferably, the liquid crystal composition according to the present invention contains one or two or more of the compounds represented by general formula (NU-01) and of the compounds represented by general formula (NU-02).

Preferably, the liquid crystal composition according to the present invention contains one or two or more of the compounds represented by general formula (NU-01) and of the compounds represented by general formula (NU-03).

Preferably, the liquid crystal composition according to the present invention contains one or two or more of the compounds represented by general formula (NU-01) and of the compounds represented by general formula (NU-06).

Preferably, the liquid crystal composition according to the present invention contains compound(s) represented by general formula (NU-01), compound(s) represented by general formula (NU-02), and compound(s) represented by general formula (NU-04).

Preferably, the liquid crystal composition according to the present invention contains compound(s) represented by general formula (NU-01), compound(s) represented by general formula (NU-03), and compound(s) represented by general formula (NU-05).

Preferably, the liquid crystal composition according to the present invention contains compound(s) represented by general formula (NU-01), compound(s) represented by general formula (NU-02), compound(s) represented by general formula (NU-03), and compound(s) represented by general formula (NU-05).

Preferably, the liquid crystal composition according to the present invention contains compound(s) represented by general formula (NU-03), compound(s) represented by general formula (NU-04), and compound(s) represented by general formula (NU-05).

Specific examples of compounds represented by general formula (NU-01) include the compounds represented by formulae (NU-01-1) to (NU-01-7) below.

[Chem. 76]

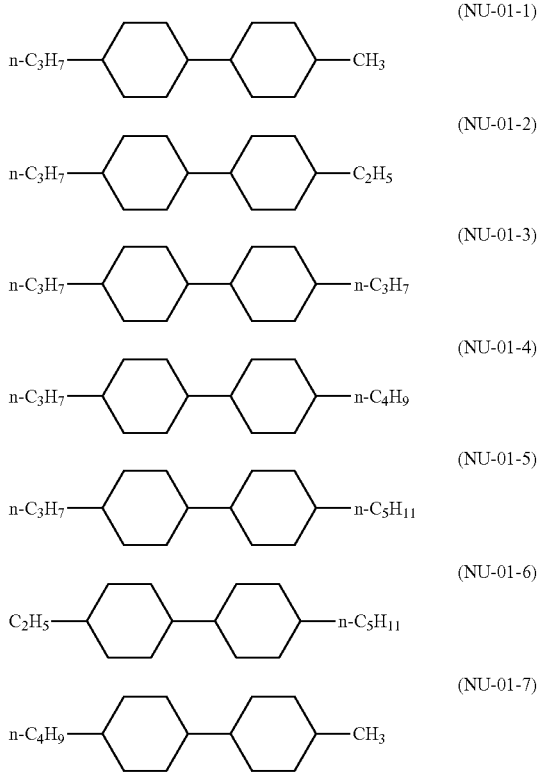

Specific examples of compounds represented by general formula (NU-02) include the compounds represented by formulae (NU-02-1) to (NU-02-6) below.

[Chem. 77]

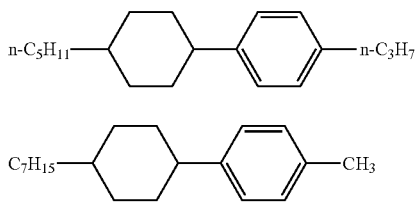

(NU-02-1)
(NU-02-2)

Specific examples of compounds represented by general formula (NU-03) include the compounds represented by formulae (NU-03-1) to (NU-03-7) below. Of these, the compound represented by formula (NU-03-1) is particularly preferred.

[Chem. 78]

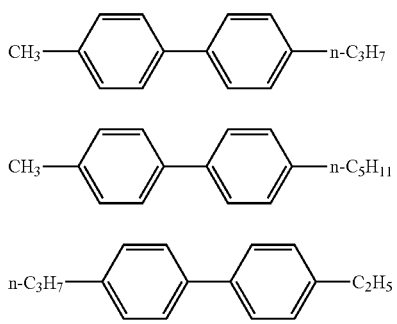

(NU-03-1)
(NU-03-2)
(NU-03-3)

Specific examples of compounds represented by general formula (NU-04) include the compounds represented by formulae (NU-04-4) to (NU-04-6) below. Of these, the compound represented by formula (NU-04-4) is particularly preferred.

[Chem. 79]

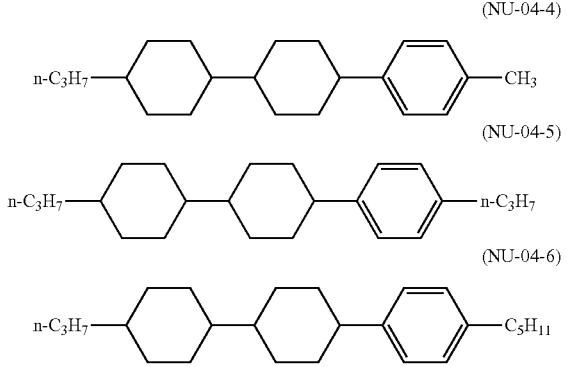

(NU-04-4)
(NU-04-5)
(NU-04-6)

Specific examples of compounds represented by general formula (NU-05) include the compounds represented by formulae (NU-05-1) to (NU-05-7) below. Of these, the compound represented by formula (NU-05-2) is particularly preferred.

[Chem. 80]

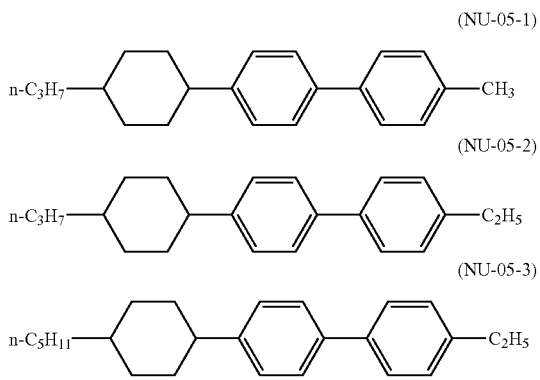

(NU-05-1)
(NU-05-2)
(NU-05-3)

Preferably, the percentage of compounds represented by general formula (NU-01) is 5% to 60% by mass, more preferably 10% to 50% by mass, even more preferably 25% to 45% by mass of the entire liquid crystal composition according to the present invention.

Preferably, the percentage of compounds represented by general formula (NU-02) is 3% to 30% by mass, more preferably 5% to 25% by mass, even more preferably 5% to 20% by mass of the entire liquid crystal composition according to the present invention.

Preferably, the percentage of compounds represented by general formula (NU-03) is 0% to 30% by mass, preferably 0% to 25.5% by mass, preferably 0% to 20% by mass, preferably 0% to 15% by mass, preferably 0% to 10% by mass of the entire liquid crystal composition according to the present invention.

Preferably, the percentage of compounds represented by general formula (NU-04) is 3% to 30% by mass, preferably 3% to 20% by mass, preferably 3% to 17% by mass, preferably 3% to 15% by mass, preferably 3% to 10% by mass of the entire liquid crystal composition according to the present invention.

Preferably, the percentage of compounds represented by general formula (NU-05) is 1% to 30% by mass, preferably 1% to 20% by mass, preferably 3% to 20% by mass, preferably 3% to 17% by mass, preferably 3% to 15% by mass of the entire liquid crystal composition according to the present invention.

Preferably, the percentage of compounds represented by general formula (NU-06) is 1% to 30% by mass, preferably 3% to 20% by mass, preferably 3% to 10% by mass of the entire liquid crystal composition according to the present invention.

The liquid crystal composition according to the present invention may further contain one or two or more compounds selected from the group consisting of the compounds represented by general formulae (N-07-1) to (N-07-12) below.

[Chem. 81]

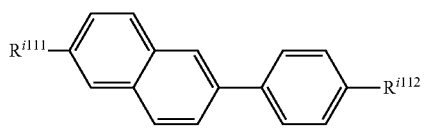

(NU-07-1)

-continued (NU-07-2)
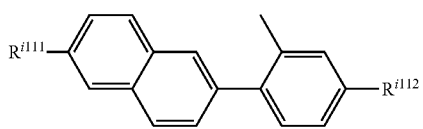

(NU-07-3)
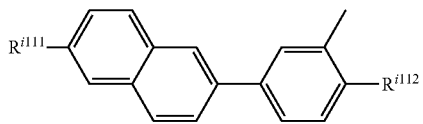

(NU-07-4)
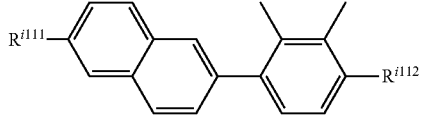

(NU-07-5)
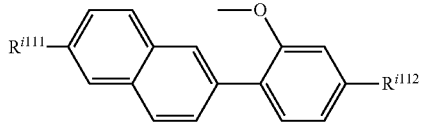

(NU-07-6)
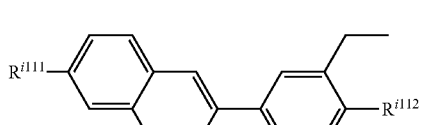

[Chem. 82]

(NU-07-7)

(NU-07-8)

(NU-07-9)

(NU-07-10)

(NU-07-11)

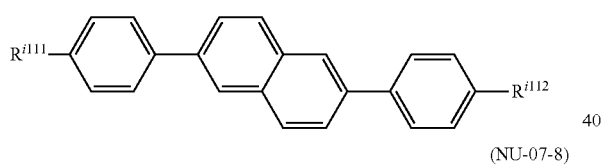

-continued (NU-07-12)
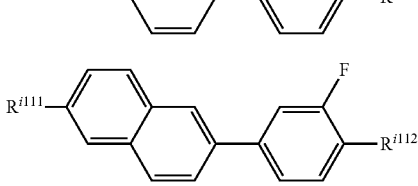

In the formulae, $R^{i111}$ and $R^{i112}$ express the same definition as $R^{L1}$ and $R^{L2}$, respectively, in general formula (L) above.

1-6. Other Compounds Besides compounds A to E above, the liquid crystal composition according to the present invention may contain commonly used compounds, such as nematic liquid crystals, smectic liquid crystals, cholesteric liquid crystals, antioxidants, ultraviolet absorbers, photostabilizers, and infrared absorbers.

For example, the compounds represented by general formulae (Q-1) to (Q-4) below may be added.

[Chem. 83]

(Q-1)

(Q-2)

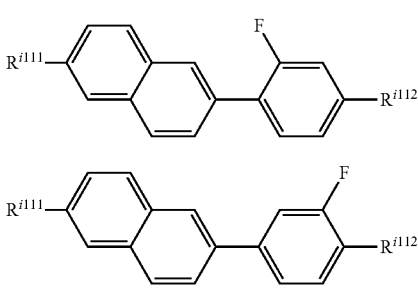

(Q-3)

(Q-4)

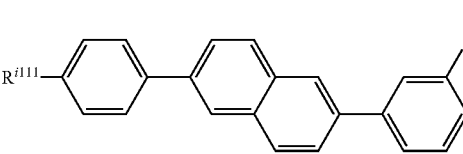

In the formulae, $R^{i111}$ and $R^{i112}$ each independently represent a C1 to C8 alkyl group, optionally with one —$CH_2$— in the alkyl group, or each of nonadjacent two or more —$CH_2$-s in the alkyl group independently, substituted by —CH=CH—, —C≡C—, —O—, —CO—, —COO—, or —OCO— unless oxygen atoms come consecutively next to each other.

It is, furthermore, preferred that the liquid crystal composition according to the present invention contain one or two or more additives selected from the group consisting of antioxidants and photostabilizers. This is because the damage-reducing effect of the antioxidant(s) and/or photostabilizer(s), in addition to those of the combination of the compound(s) represented by general formula (I) and the compound(s) represented by general formula (II), both described above, helps further improve the reliability of the alkenyl-containing liquid crystal composition and devices made therewith. An example of a preferred percentage is 1.0% by mass or less, more preferably 0.5% by mass or less, even more preferably 0.11% by mass or less.
More specifically, the compounds represented by formulae (III-1) to (III-41) below are preferred for use as antioxidants or photostabilizers.
[Chem. 84]
(III-1)
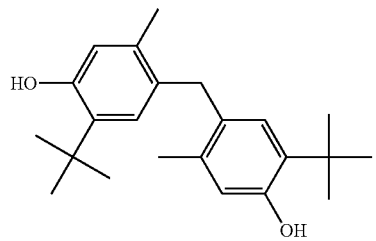
(III-2)
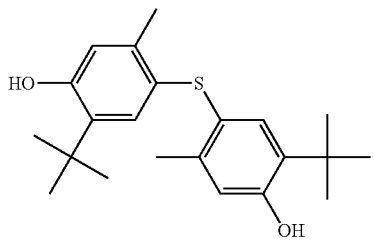
(III-3)
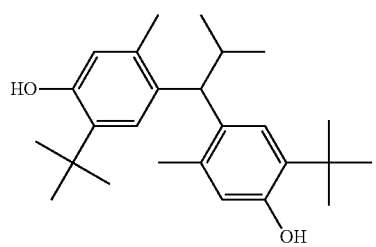
(III-4)
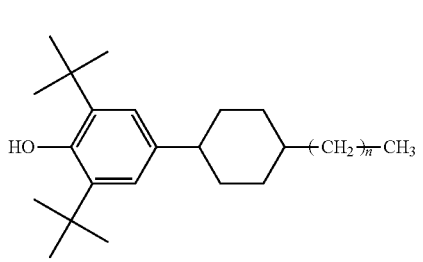
(III-5)
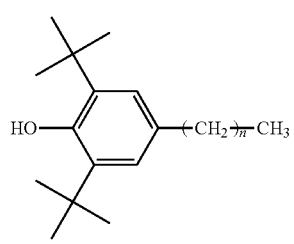
[Chem. 85]
(III-6)
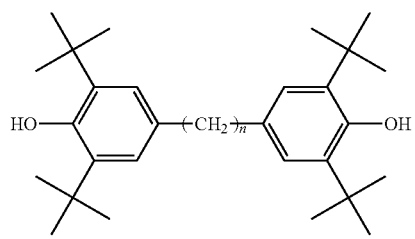
(III-7)
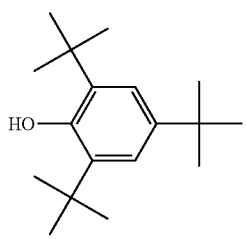
(III-8)
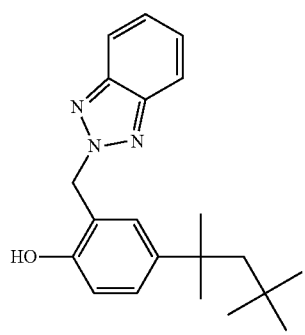
(III-9)
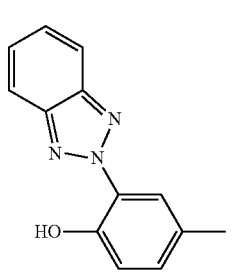

-continued
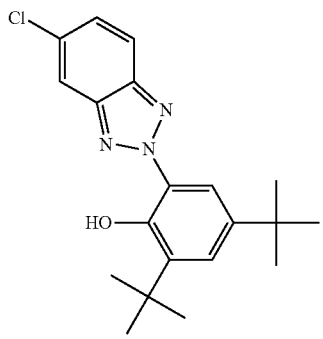
(III-10)
[Chem. 86]
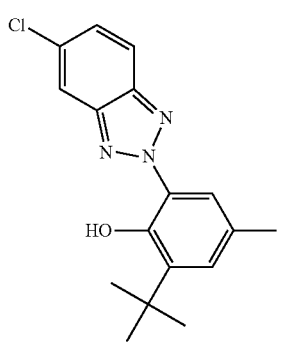
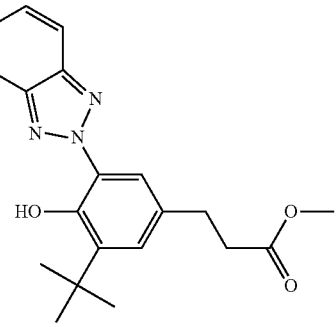
(III-11)                                    (III-12)
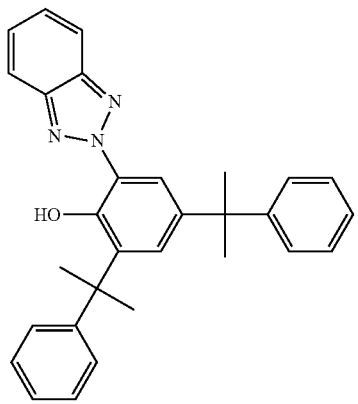
(III-13)
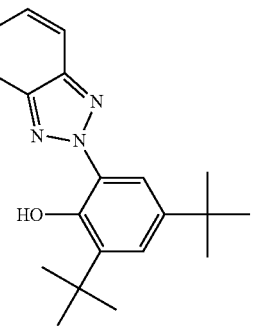
(III-14)
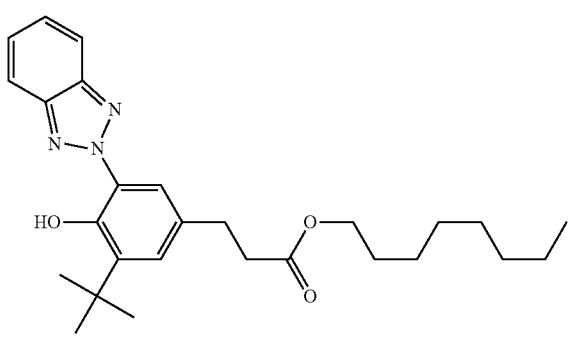
(III-15)

[Chem. 87]
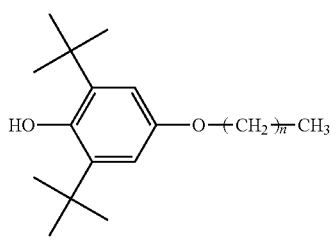 (III-16)
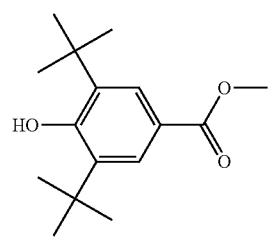 (III-17)
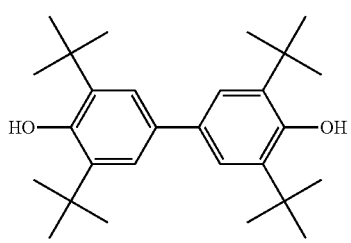 (III-18)
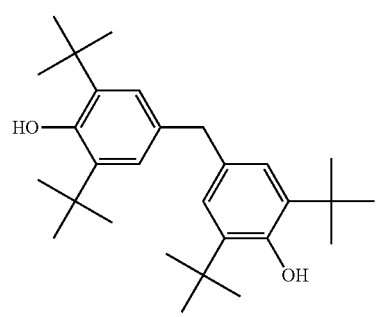 (III-19)
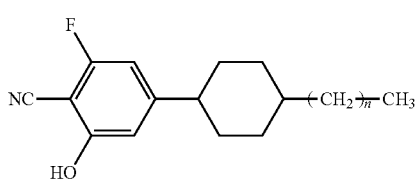 (III-20)
[Chem. 88]
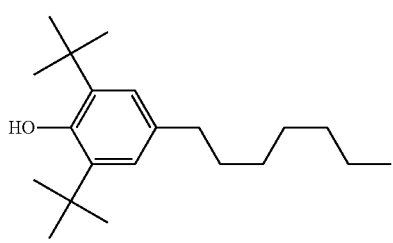 (III-21)
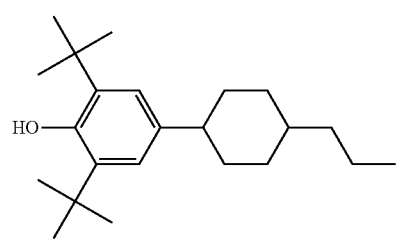 (III-22)
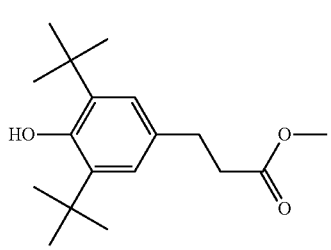 (III-23)
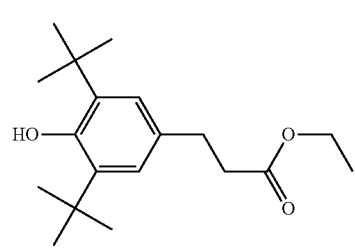 (III-24)

(III-25)
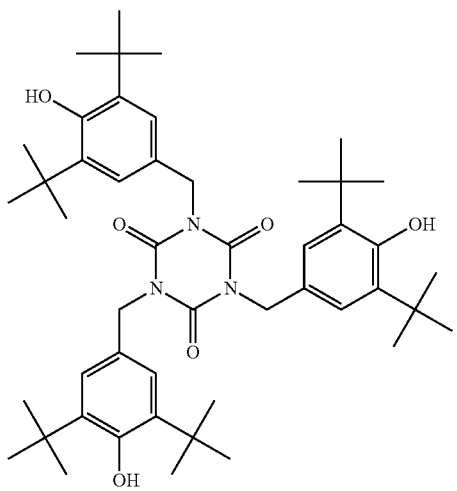
[Chem. 89]
(III-26)
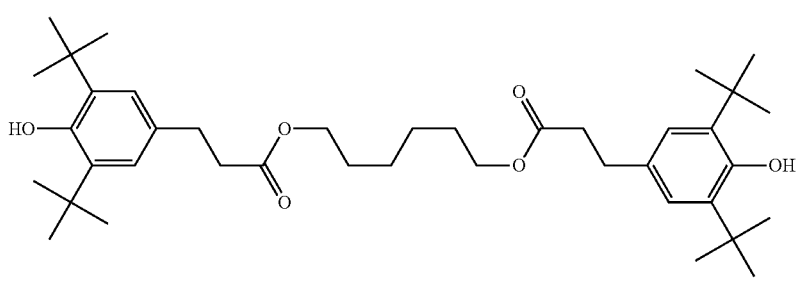
(III-27)
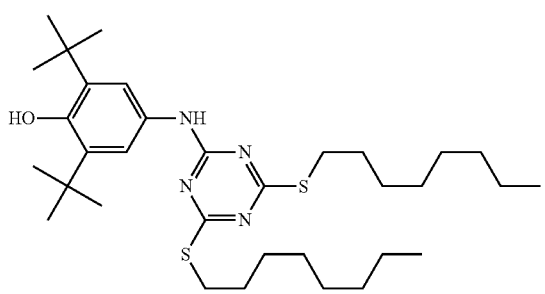
(III-28)
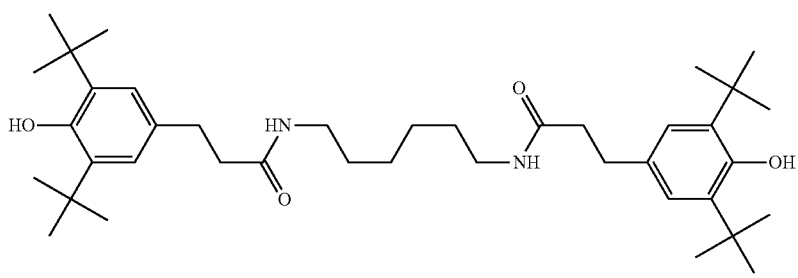
(III-29)
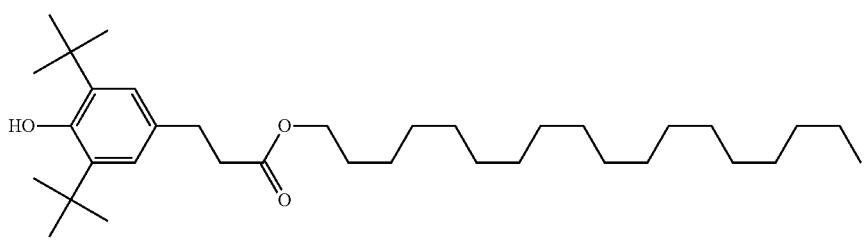

-continued
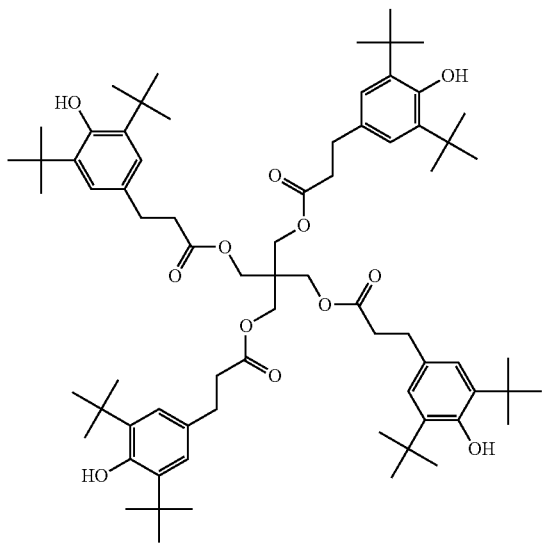
(III-30)
[Chem. 90]
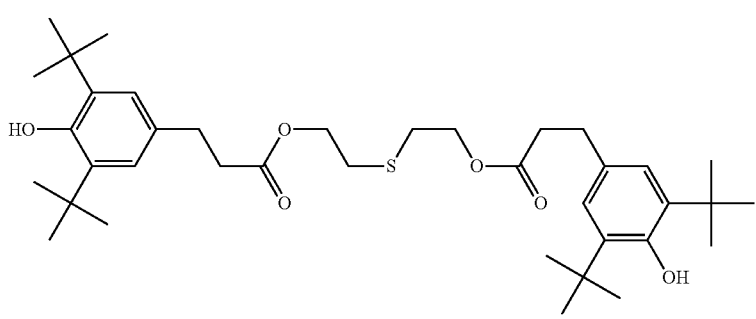
(III-31)
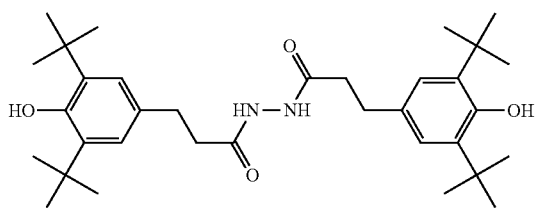
(III-32)
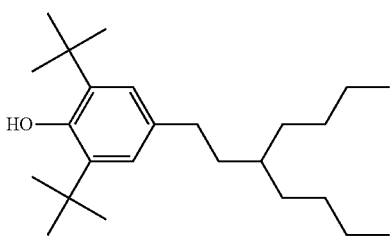
(III-33)
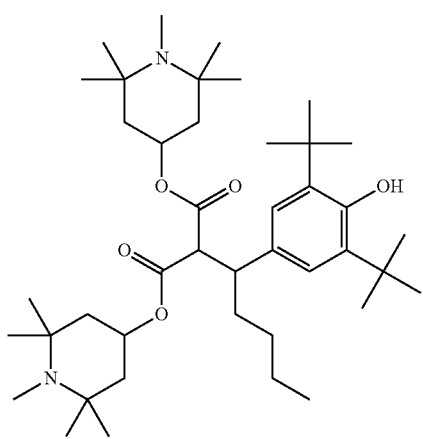
(III-34)
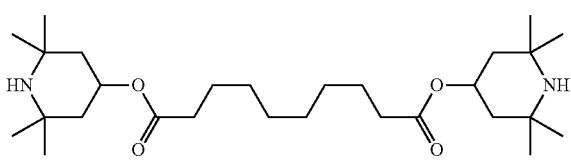
(III-35)

-continued
(III-36)
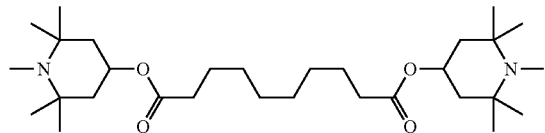
[Chem. 91]
(III-37) (III-38)
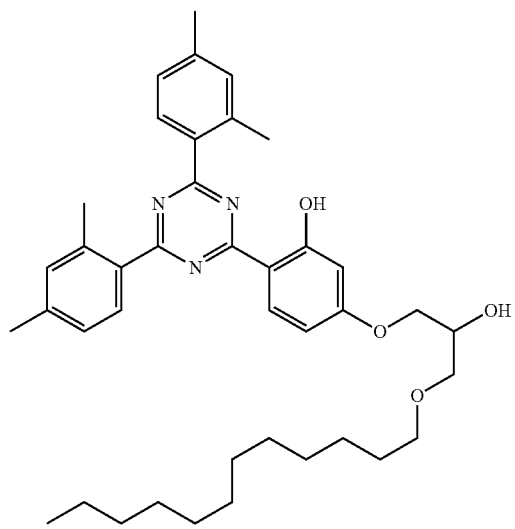 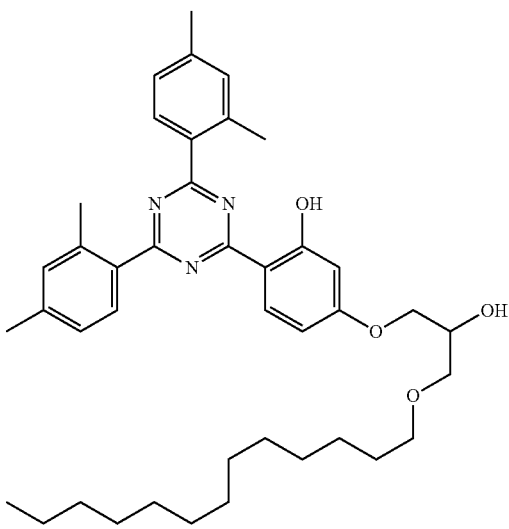
[Chem. 92]
(III-39) (III-40)
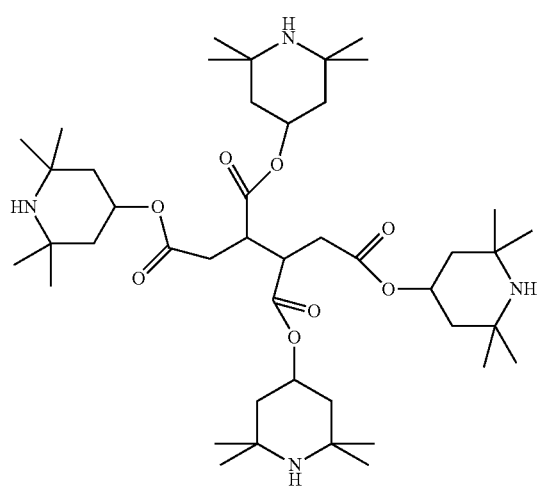 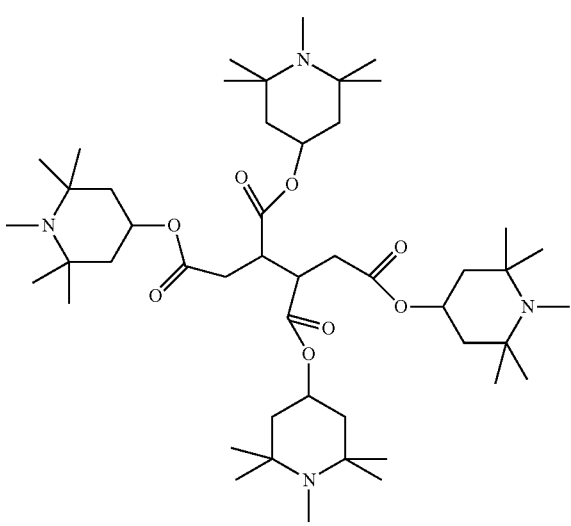
(III-41)
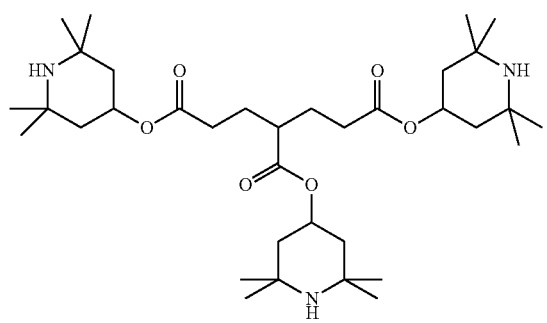

[Chem. 93]

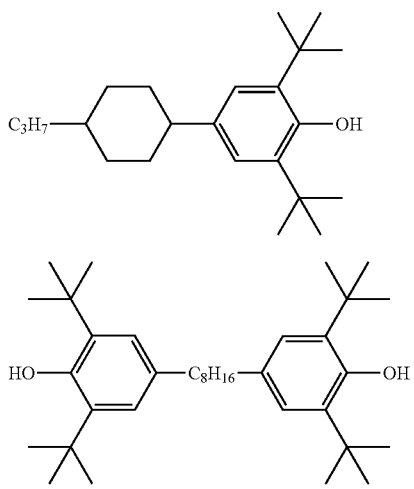
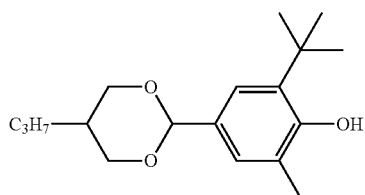
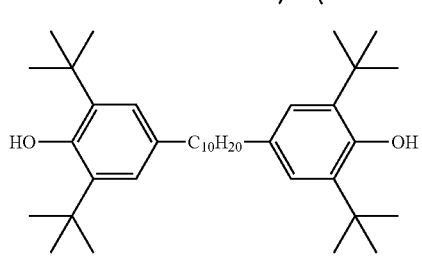

In the formulae, n represents an integer of 0 to 20.

Preferably, the percentage of antioxidants and photostabilizers is from 0.001% by mass to 1% by mass, more preferably from 0.001% by mass to 0.1% by mass, in particular 0.001% by mass to 0.05% by mass of the entire liquid crystal composition according to the present invention.

1-7. Others

Preferably, the liquid crystal composition according to the present invention is configured such that the maximum total percentage of compounds A, represented by general formula (Y), and compounds C, represented by general formula (II), is 100% by mass, 99% by mass, 98% by mass, 97% by mass, 96% by mass, 95% by mass, 94% by mass, 93% by mass, 92% by mass, 91% by mass, 90% by mass, 89% by mass, 88% by mass, 87% by mass, 86% by mass, 85% by mass, or 84% by mass of the entire liquid crystal composition according to the present invention. Preferably, the minimum total percentage of these compounds is 78% by mass, 80% by mass, 81% by mass, 83% by mass, 85% by mass, 86% by mass, 87% by mass, 88% by mass, 89% by mass, 90% by mass, 91% by mass, 92% by mass, 93% by mass, 94% by mass, 95% by mass, 96% by mass, 97% by mass, 98% by mass, 99% by mass, or 100% by mass of the entire liquid crystal composition according to the present invention.

Preferably, the liquid crystal composition according to the present invention is configured such that the maximum total percentage of compounds represented by general formula (I), compounds represented by general formula (II), compounds represented by any of general formulae (N-01) to (N-05), and compounds represented by any of general formulae (NU-01) to (NU-06) is 100% by mass, 99% by mass, 98% by mass, 97% by mass, 96% by mass, 95% by mass, 94% by mass, 93% by mass, 92% by mass, 91% by mass, 90% by mass, 89% by mass, 88% by mass, 87% by mass, 86% by mass, 85% by mass, or 84% by mass of the entire liquid crystal composition according to the present invention. Preferably, the minimum total percentage of these compounds is 78% by mass, 80% by mass, 81% by mass, 83% by mass, 85% by mass, 86% by mass, 87% by mass, 88% by mass, 89% by mass, 90% by mass, 91% by mass, 92% by mass, 93% by mass, 94% by mass, 95% by mass, 96% by mass, 97% by mass, 98% by mass, 99% by mass, or 100% by mass of the entire liquid crystal composition according to the present invention.

Preferably, the liquid crystal composition according to the present invention is configured such that the maximum total percentage of compounds represented by general formula (I), compounds represented by general formula (II), compounds represented by any of general formulae (N-01) to (N-05), and compounds represented by any of general formulae (NU-01) to (NU-06) is 100% by mass, 99% by mass, 98% by mass, 97% by mass, 96% by mass, 95% by mass, 94% by mass, 93% by mass, 92% by mass, 91% by mass, 90% by mass, 89% by mass, 88% by mass, 87% by mass, 86% by mass, 85% by mass, or 84% by mass of the entire liquid crystal composition according to the present invention. Preferably, the minimum total percentage of these compounds is 78% by mass, 80% by mass, 81% by mass, 83% by mass, 85% by mass, 86% by mass, 87% by mass, 88% by mass, 89% by mass, 90% by mass, 91% by mass, 92% by mass, 93% by mass, 94% by mass, 95% by mass, 96% by mass, 97% by mass, 98% by mass, 99% by mass, or 100% by mass of the entire liquid crystal composition according to the present invention.

Preferably, the liquid crystal composition according to the present invention is configured such that the maximum total percentage of compounds represented by general formula (I-1) or (I-2), compounds represented by any of general formulae (II-NU-01) to (II-NU-06), compounds represented by any of general formulae (N-01) to (N-05), and compounds represented by any of general formulae (NU-01) to (NU-06) is 100% by mass, 99% by mass, 98% by mass, 97% by mass, 96% by mass, 95% by mass, 94% by mass, 93% by mass, 92% by mass, 91% by mass, 90% by mass, 89% by mass, 88% by mass, 87% by mass, 86% by mass, 85% by mass, or 84% by mass of the entire liquid crystal composition according to the present invention. Preferably, the minimum total percentage of these compounds is 78% by mass, 80% by mass, 81% by mass, 83% by mass, 85% by mass, 86% by mass, 87% by mass, 88% by mass, 89% by mass, 90% by mass, 91% by mass, 92% by mass, 93% by mass, 94% by mass, 95% by mass, 96% by mass, 97% by mass, 98% by mass, 99% by mass, or 100% by mass of the entire liquid crystal composition according to the present invention.

Preferably, the liquid crystal composition according to the present invention is configured such that the maximum total percentage of compounds represented by any of general formulae (I-1) and (I-2), compounds represented by any of general formulae (II-NU-01) to (II-NU-06), compounds represented by any of general formulae (N-01) to (N-05), compounds represented by any of general formulae (NU-01) to (NU-06), and polymerizable compounds represented by general formula (P) is 100% by mass, 99% by mass, 98% by mass, 97% by mass, 96% by mass, 95% by mass, 94% by mass, 93% by mass, 92% by mass, 91% by mass, 90% by mass, 89% by mass, 88% by mass, 87% by mass, 86% by mass, 85% by mass, or 84% by mass of the entire liquid crystal composition according to the present invention. Preferably, the minimum total percentage of these compounds is 78% by mass, 80% by mass, 81% by mass, 83% by mass, 85% by mass, 86% by mass, 87% by mass, 88% by mass, 89% by mass, 90% by mass, 91% by mass, 92% by mass, 93% by mass, 94% by mass, 95% by mass, 96% by mass, 97% by mass, 98% by mass, 99% by mass, or 100% by mass of the entire liquid crystal composition according to the present invention.

Preferably, the liquid crystal composition according to the present invention contains one or two or more compounds selected from the group consisting of the compounds represented by general formulae (I-1), (I-2), (I-3), (I-4), (I-5), and (I-6), one or two or more compounds selected from the group consisting of the compounds represented by general formulae (II-NU-01), (II-NU-02), (II-NU-03), (II-NU-04), (II-NU-05), and (II-NU-06), one or two or more compounds selected from the group consisting of the compounds represented by general formulae (II-N-01), (II-N-02), (II-N-03), (II-N-04), and (II-N-05), one or two or more compounds selected from the group consisting of the compounds represented by general formulae (N-01), (N-02), (N-03), (N-04), and (N-05), and one or two or more compounds selected from the group consisting of the compounds represented by general formulae (NU-01), (NU-02), (NU-03), (NU-04), (NU-05), and (NU-06). Preferably, the liquid crystal composition contains one or two or more polymerizable compounds represented by general formula (P), preferably one or two or more polymerizable compounds represented by general formula (RM) or (i), besides these compounds.

It is, furthermore, preferred that the liquid crystal composition according to the present invention contain, at least, one or two or more compounds selected from the group consisting of the compounds represented by general formulae (I-1-1), (I-1-2), (I-1-3), (I-1-4), (I-2-1), (I-2-2), (I-2-3), and (I-2-4), one or two or more compounds selected from the group consisting of the compounds represented by general formulae (II-NU-01A), (II-NU-02A), (II-NU-03A), (II-NU-04A), and (II-NU-05A), and one or two or more compounds selected from the group consisting of the compounds represented by general formulae (II-N-01), (II-N-02), (II-N-03), (II-N-04), and (II-N-05). Preferably, the liquid crystal composition contains one or two or more polymerizable compounds represented by general formula (P), preferably one or two or more polymerizable compounds represented by general formula (RM) or (i), besides these compounds.

Preferably, the liquid crystal composition according to the present invention contains one or two or more compounds selected from the group consisting of the compounds represented by general formulae (I-1-1), (I-1-2), (I-1-3), (I-1-4), (I-2-1), (I-2-2), (I-2-3), and (I-2-4) and one or two or more compounds selected from the group consisting of the compounds represented by general formula (II-NU-01$_1$). Preferably, the liquid crystal composition contains one or two or more polymerizable compounds represented by general formula (P), preferably one or two or more polymerizable compounds represented by general formula (RM) or (i), besides these compounds.

Preferably, the liquid crystal composition according to the present invention contains one or two or more compounds selected from the group consisting of the compounds represented by general formulae (I-1-1), (I-1-2), (I-1-3), and (I-1-4) and one or two or more compounds selected from the group consisting of the compounds represented by general formula (II-NU-01$_1$), preferably with the compound(s) represented by general formula (II-NU-01$_1$) being the compound represented by formula (II-NU-01A$_{12}$). Preferably, the liquid crystal composition contains one or two or more polymerizable compounds represented by general formula (P), preferably one or two or more polymerizable compounds represented by general formula (RM) or (i), besides these compounds.

Preferably, the liquid crystal composition according to the present invention contains one or two or more compounds selected from the group consisting of the compounds represented by general formulae (I-2-1), (I-2-2), (I-2-3), and (I-2-4) and one or two or more compounds selected from the group consisting of the compounds represented by general formula (II-NU-01$_1$), preferably with the compound(s) represented by general formula (II-NU-01$_1$) being the compound represented by formula (II-NU-01A$_{12}$). Preferably, the liquid crystal composition contains one or two or more polymerizable compounds represented by general formula (P), preferably one or two or more polymerizable compounds represented by general formula (RM) or (i), besides these compounds.

Preferably, the liquid crystal composition according to the present invention has a nematic-isotropic liquid phase transition temperature ($T_{ni}$) from 70° C. to 120° C., more preferably from 80° C. to 120° C., in particular from 90° C. to 110° C. A $T_{ni}$ of 80° C. or above is herein described as high.

Preferably, the liquid crystal composition according to the present invention has a refractive-index anisotropy (Δn) at 20° C. from 0.08 to 0.14, more preferably from 0.09 to 0.13, in particular from 0.09 to 0.12. To be more specific, if the liquid crystal composition is for a small cell gap, it is preferred that the Δn at 20° C. be from 0.10 to 0.13, and if the composition is for a large cell gap, it is preferred that the Δn at 20° C. be from 0.08 to 0.10. A Δn of 0.09 or more is herein defined as being large.

The liquid crystal composition according to the present invention has a rotational viscosity ($\gamma_1$) at 20° C. from 50 to 160 mPa·s, but preferably, the $\gamma_1$ at 20° C. is from 55 to 160 mPa·s, preferably from 60 to 160 mPa·s, preferably from 70 to 150 mPa·s, preferably from 75 to 140 mPa·s, preferably from 80 to 130 mPa·s, preferably from 80 to 120 mPa·s.

Preferably, the liquid crystal composition according to the present invention has a negative dielectric anisotropy with an absolute value of 2 or greater. To be more specific, the liquid crystal composition according to the present invention has a dielectric anisotropy (Δε) at 20° C. from −2.0 to −8.0, but preferably, the Δε at 20° C. is from −2.0 to −6.0, more preferably from −2.0 to −5.0, more preferably from −2.5 to −4.0, in particular from −2.5 to −3.5.

2. Liquid Crystal Display Element

A liquid crystal display element according to the present invention is an element made with a liquid crystal composition as described in the "1. Liquid Crystal Composition"

section above. The liquid crystal display element according to the present invention can have a fast response time and be highly reliable because the liquid crystal composition forming its liquid crystal layer contains compound(s) A, represented by general formula (Y), and compound(s) C, represented by general formula (II). The liquid crystal display element according to the present invention, furthermore, can exhibit excellent display quality by virtue of possessing such characteristics.

Preferably, the liquid crystal display element according to the present invention is an active matrix-addressed one. The drive technology of the liquid crystal display element according to the present invention can be PSA, PSVA, VA, IPS, FFS, PS-IPS, PS-FFS, NPS, or ECB. Preferably, the liquid crystal display element according to the present invention is a PSA or PSVA one. It is, furthermore, preferred that the liquid crystal display element according to the present invention be an IPS or FFS one.

The FIGURE is a schematic diagram illustrating an example of a liquid crystal display element according to the present invention. The structure of the liquid crystal display element according to the present invention, however, does not need to be like this example. In the FIGURE, furthermore, the structural elements are illustrated spaced apart for the sake of convenience in explanation. The liquid crystal display element 1 illustrated in the FIGURE includes first and second substrates 2 and 3 opposite each other and a liquid crystal layer 4 between the first and second substrates 2 and 3. As illustrated by way of example in the FIGURE, the first substrate 2 has a pixel-electrode layer 5 formed on its surface on the liquid crystal layer 4 side. The second substrate 3 has a common-electrode layer 6 on its liquid crystal layer 4 side. The first and second substrates 2 and 3 may be sandwiched between a pair of polarizers 7 and 8. On the liquid crystal layer 4 side of the second substrate 3, there may also be a color filter 9.

The liquid crystal layer 4 contains a liquid crystal composition as described in the "1. Liquid Crystal Composition" section above. A liquid crystal display element produced using a liquid crystal composition containing a polymerizable compound has polymers of the polymerizable compound, formed through ultraviolet irradiation during the production of the display element, locally at the interfaces of the liquid crystal layer 4 on the first and second substrate 2 sides. In that case, therefore, the interfaces between the liquid crystal layer 4 and the first and second substrates 2 contain polymers of a polymerizable compound formed there.

Although not illustrated, the liquid crystal display element according to the present invention includes first and second substrates opposite each other and a liquid crystal layer between the first and second substrates, the liquid crystal layer containing a liquid crystal composition as described above, and can have a first alignment film on the surface of the first substrate on the liquid crystal layer side and a second alignment film on the surface of the liquid crystal layer on the second substrate side. That is, the liquid crystal display element according to the present invention can have a structure in which a first polarizer, a first substrate, a first alignment film, a pixel-electrode layer, a liquid crystal layer, a common-electrode layer, a color filter, a second alignment film, a second substrate, and a second polarizer are stacked in this order. The alignment films have the function to align the liquid crystal molecules. The alignment films can be ones commonly used in liquid crystal display elements, such as polyimide alignment films.

The liquid crystal display element according to the present invention can be produced by known methods. If it is a PSA liquid crystal display element, for example, its production can be through the following procedure. First, first and second substrates placed with their alignment film sides facing each other are joined together, giving a blank cell. Between the substrates, spacer projections and a seal component are interposed so that the desired cell gap will be obtained. Then the liquid crystal composition is sandwiched between the first and second substrates of the blank cell, and the seal component is cured to seal the liquid crystal composition between the first and second substrates. Thereafter the polymerizable compound(s) contained in the liquid crystal composition is polymerized through irradiation with actinic rays of energy, such as ultraviolet radiation or electron beams. This gives the desired liquid crystal display element.

The present invention is not limited to the above embodiments. The above embodiments are for illustrative purposes; anything that is structured substantially in the same way, and provides the same advantages, as any technical idea set forth in the claims of the present invention is encompassed in the technical scope of the present invention.

EXAMPLES

The following describes the present invention in further detail by providing examples. The present invention, however, is not limited to these examples. "%" in the context of the compositions of the Examples and Comparative Examples below refers to "% by mass." In the Examples, the following abbreviations are used to describe compounds.

In the Examples, compounds are described using the following abbreviations. n represents a natural number.

| (Side Chains) | | |
|---|---|---|
| -n | —$C_nH_{2n+1}$ | A linear Cn alkyl group |
| n- | $C_nH_{2n+1}$— | A linear Cn alkyl group |
| —On | —$OC_nH_{2n+1}$ | A linear Cn alkoxy group |
| nO— | $C_nH_{2n+1}$O— | A linear Cn alkoxy group |
| —V | —CH=$CH_2$ | |
| V— | $CH_2$=CH— | |
| —V1 | —CH=CH—$CH_3$ | |
| 1V— | $CH_3$—CH=CH— | |
| —F | —F | |
| —$OCF3$ | —$OCF_3$ | |

(Linking Groups)
-1O— —$CH_2$—O—
—O1- —O—$CH_2$—
-2- —$CH_2$—$CH_2$—
—COO— —COO—
—OCO— —OCO—
A single bond
(Ring Structures)

[Chem. 94]

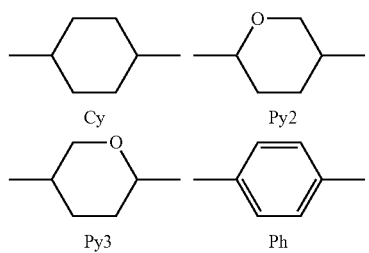

Cy  Py2

Py3  Ph

-continued

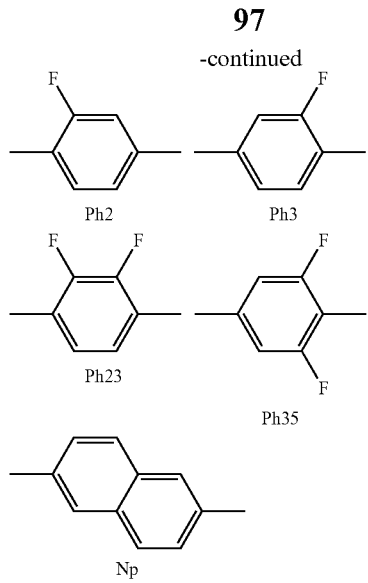

In the Examples, the following characteristics were measured. Unless stated specifically, the characteristics were measured according to the methods set forth in the Standard of Japan Electronics and Information Technology Industries Association JEITA ED-2521B, amended in March 2009, issued by Japan Electronics and Information Technology Industries Association.

$T_{ni}$: Nematic-isotropic liquid phase transition temperature (° C.)

Δn: Refractive-index anisotropy at 20° C.

ΔE: Dielectric anisotropy at 20° C.

$γ_1$: Rotational viscosity (mPa·s) at 20° C.

(1) Synthesis of Compounds A

As compounds A, the compounds represented by formulae (RM-#1) to (RM-#4) below were synthesized. The compounds' structure was identified by 1H-NMR.

(Synthesis of the Compound Represented by Formula (RM-#1))

To a reactor equipped with a stirrer, a condenser, and a thermometer were added 4.4 g (100.83 millimoles) of sodium hydroxide, 20 g (66.2 millimoles) of 5,5-bis(bromomethyl)-2,2-dimethyl-1,3-dioxane, and 120 ml of dimethylsulfoxide. With the reactor kept at 5° C. or below in an ice-cooled bath, 10.0 g (65.7 millimoles) of 2-benzyloxyethanol was slowly added dropwise in a nitrogen gas atmosphere. After the addition finished, the reactor was returned to room temperature, and the materials were allowed to react for 10 hours. The reaction solution was combined with 250 ml of hexane and 250 ml of water, washed with the water and then with a saturated solution of salt in water, and the organic layer was dried with anhydrous sodium sulfate. After the solvent was distilled out, the residue was purified through a column with a five-fold amount (by weight) of silica gel, giving 17.9 g of the compound represented by formula (1) below.

[Chem. 95]

(1)

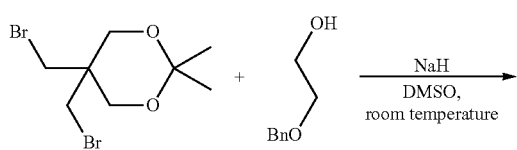

-continued

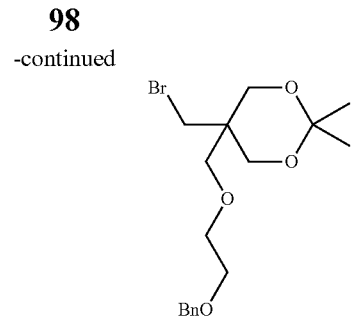

Then 9.6 g (24.09 millimoles) of the resulting compound represented by formula (1), 6.3 g (21.40 millimoles) of 3-fluoro-4'-benzyloxy-1,1'-biphenyl-4-ol, 13.8 g (63.8 millimoles) of tripotassium phosphate, 800 mg (5.33 millimoles) of sodium iodide, and 45 ml of dimethylformamide were added to a reactor equipped with a stirrer, a condenser, and a thermometer, heated to 90° C., and allowed to react for 6 hours. The reaction solution was combined with 100 ml of ethyl acetate and 100 ml of water, washed with the water and then with a saturated solution of salt in water, and the organic layer was dried with anhydrous sodium sulfate. After the solvent was distilled out, the residue was purified through a column with a two-fold amount (by weight) of silica gel, giving 10.3 g of the compound represented by formula (2) below.

[Chem. 96]

(2)

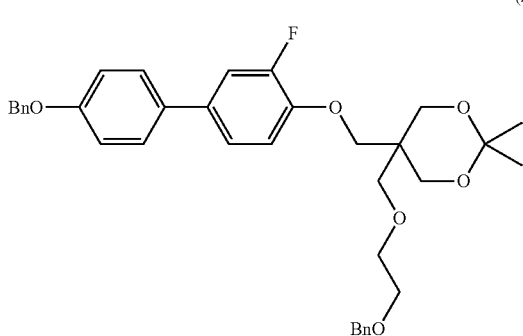

Subsequently, 5.0 g (8.52 millimoles) of the resulting compound represented by formula (2), 500 mg of Kawaken Fine Chem. Co., Ltd.'s 20% palladium hydroxide charcoal catalyst WET, and 40 ml of tetrahydrofuran were added to a reactor equipped with a stirrer and a heater and allowed to react for 5 hours at 50° C. in a pressurized hydrogen gas atmosphere (0.5 MPa). After the catalyst was removed by filtration, the solvent was distilled out, and then the residue was purified through a column with a two-hold amount (by weight) of silica gel, giving 3.3 g of the compound represented by formula (3) below.

[Chem. 97]

(3)

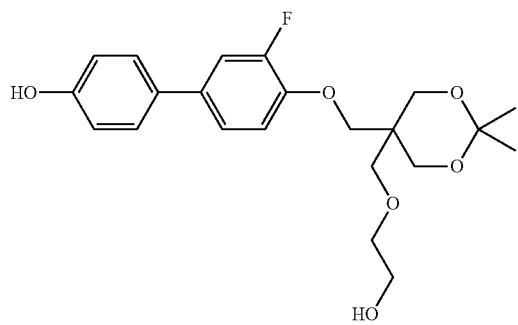

After that, 3.0 g (7.38 millimoles) of the resulting compound illustrated in (3), 1.9 g (22.1 millimoles) of methacrylic acid, 270 mg (2.2 millimoles) of 4-dimethylaminopyridine, and 30 ml of methylene chloride were added to a reactor equipped with a stirrer, a condenser, and a thermometer. With the reactor kept at 5° C. or below in an ice-cooled bath, 3.1 g (24.6 millimoles) of N,N'-diisopropylcarbodiimide was slowly added dropwise in a nitrogen gas atmosphere. After the addition finished, the reactor was returned to room temperature, and the materials were allowed to react for 5 hours. The reaction solution was combined with 20 ml of water, washed with the water and then with a saturated solution of salt in water, and the organic layer was dried with anhydrous sodium sulfate. After the solvent was distilled out, the residue was purified through a column with a two-fold amount (by weight) of silica gel, giving 3.5 g of the compound represented by formula (4) below.

[Chem. 98]

(4)

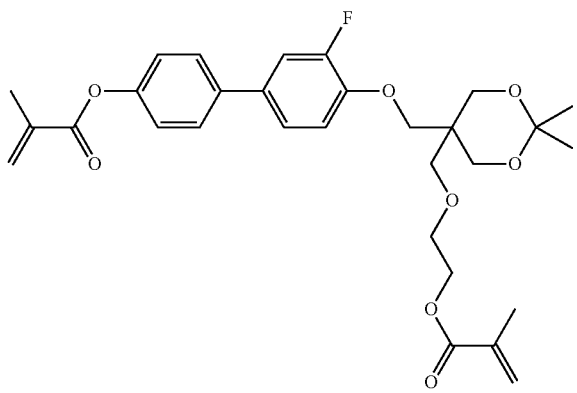

Thereafter, 3.3 g of the resulting compound represented by formula (4), 33 ml of tetrahydrofuran, and 11 ml of 10% hydrochloric acid were added to a reactor equipped with a stirrer, a heater, and a thermometer and allowed to react for 5 hours at 40° C. in a nitrogen gas atmosphere. The reaction solution was combined with 50 ml of ethyl acetate, washed with water and then with a saturated solution of salt in water, and the organic layer was dried with anhydrous sodium sulfate. After the solvent was distilled out, the residue was purified through a column with a two-fold amount (by weight) of silica gel, giving 3.0 g of the compound represented by formula (5) below.

[Chem. 99]

(5)

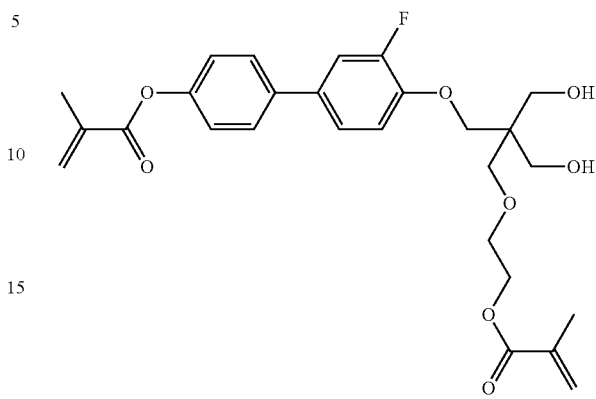

After that, 0.9 g (1.79 millimoles) of the resulting compound represented by formula (5), 0.58 g (5.34 millimoles) of ethyl chloroformate, and 13.5 ml of methylene chloride were added. With the reactor kept at 5° C. or below in an ice-cooled bath, 0.55 g (5.44 millimoles) of triethylamine was slowly added dropwise in a nitrogen gas atmosphere. After the addition finished, the reactor was returned to room temperature, and the materials were allowed to react for 5 hours. The reaction solution was combined with 15 ml of a saturated solution of sodium hydrogen carbonate in water and washed therewith, then washed with water, and then with a saturated solution of salt in water, and the organic layer was dried with anhydrous sodium sulfate. After the solvent was distilled out, the residue was purified through a column with a two-fold amount (by weight) of silica gel, giving 0.41 g of the compound represented by (RM-#1) below. In Tables 2 and 3 below, this compound represented by formula (RM-#1) is written as "a-4."

[Chem. 100]

(RM-#1)

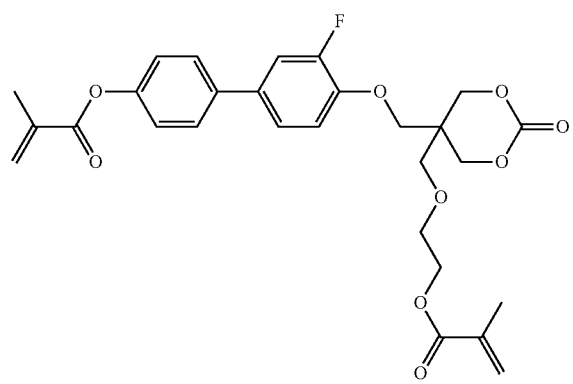

$^1$H-NMR (solvent: deuterated chloroform): δ: 1.91 (s, 3H), 2.08 (s, 3H), 3.71 (s, 2H), 3.74 (d, 2H), 4.12 (s, 2H), 4.30 (d, 2H), 4.45 (t, 2H), 4.49 (t, 2H), 5.55 (s, 1H), 5.78 (s, 1H), 6.07 (s, 1H), 6.37 (s, 1H), 7.01 (dd, 1H), 7.19 (d, 2H), 7.28 (d, 1H), 7.32 (d, 1H), 7.53 (d, 2H)

(Synthesis of the Compound Represented by Formula (RM-#2))

First, the above-described synthesis of the compound represented by formula (1) was done completely in the same way except that benzyl alcohol was added dropwise instead of 2-benzyloxyethanol. This gave 11.5 g of the compound represented by formula (6).

[Chem. 101]

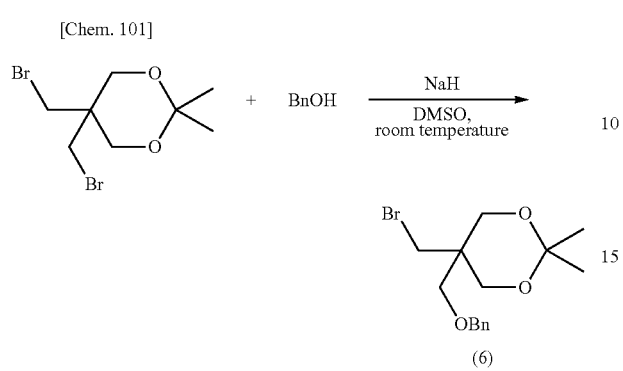

(6)

Then the above-described synthesis of the compound represented by formula (2) was done completely in the same way except that the compound represented by formula (1) was replaced with that represented by formula (6), and that 3-fluoro-4'-benzyloxy-1,1'-biphenyl-4-ol was replaced with 4'-benzyloxy-1,1'-biphenyl-4-ol. This gave 12.7 g of the compound represented by formula (7) below.

[Chem. 102]

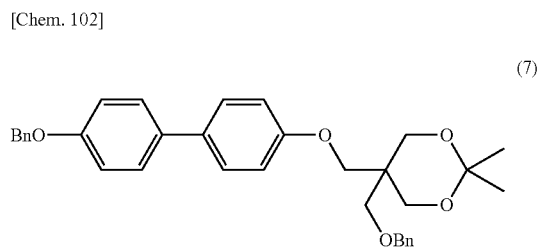

(7)

Subsequently, the above-described synthesis of the compound represented by formula (3) was done completely in the same way except that the compound represented by formula (2) was replaced with that represented by formula (7). This gave 8.3 g of the compound represented by formula (8) below.

[Chem. 103]

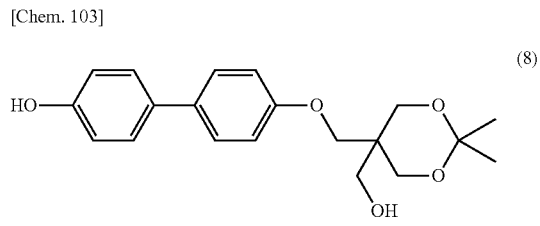

(8)

After that, the above-described synthesis of the compound represented by formula (4) was done completely in the same way except that the compound represented by formula (3) was replaced with that represented by formula (8). This gave 7.7 g of the compound represented by formula (9) below.

[Chem. 104]

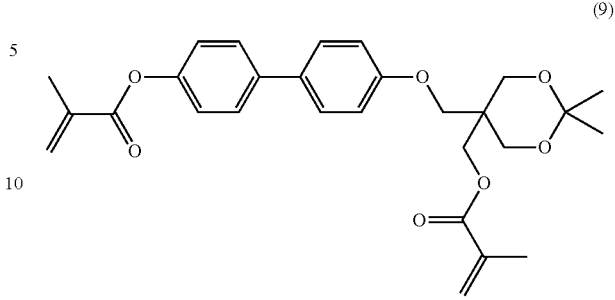

(9)

Thereafter, the above-described synthesis of the compound represented by formula (5) was done completely in the same way except that the compound represented by formula (4) was replaced with that represented by formula (9). This gave 5.1 g of the compound represented by formula (10) below.

[Chem. 105]

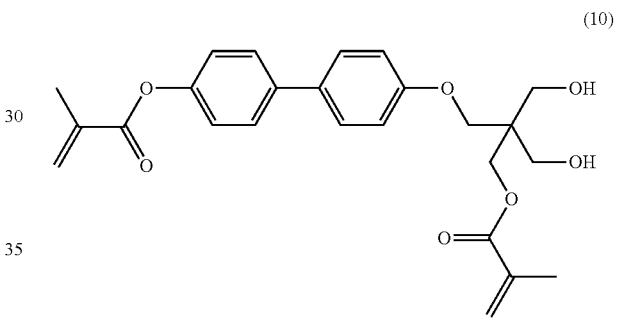

(10)

After that, the above-described synthesis of the compound represented by formula (RM-#1) was done completely in the same way except that the compound represented by formula (5) was replaced with that represented by formula (10). This gave 1.5 g of the compound represented by formula (RM-#2) below. In Tables 2 and 3 below, this compound represented by formula (RM-#2) is written as "a-1."

[Chem. 106]

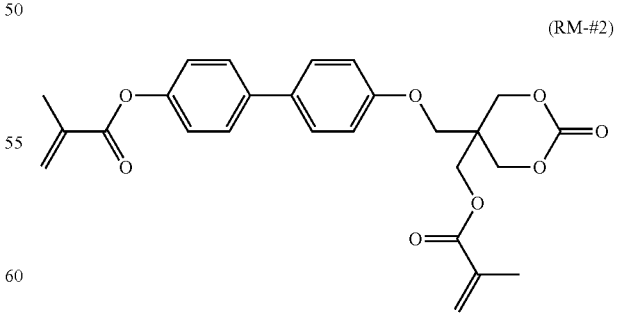

(RM-#2)

$^{1}$H-NMR (solvent: deuterated chloroform): δ: 1.96 (s, 3H), 2.08 (s, 3H), 4.09 (s, 2H), 4.38 (s, 2H), 4.46 (d, 2H), 4.56 (d, 2H), 5.65 (s, 1H), 5.77 (s, 1H), 6.12 (s, 1H), 6.37 (s, 1H), 6.96 (d, 2H), 7.18 (d, 2H), 7.53 (d, 4H)

(Synthesis of the Compound Represented by Formula (RM-#3))

To a reactor equipped with a stirrer, a condenser, and a thermometer were added 2.5 g (5.68 millimoles) of the aforementioned compound represented by (10), 0.65 g (5.34 millimoles) of methyl chloroglyoxylate, and 13.5 ml of methylene chloride. With the reactor kept at 5° C. or below in an ice-cooled bath, 0.55 g (5.44 millimoles) of triethylamine was slowly added dropwise in a nitrogen gas atmosphere. After the addition finished, the reactor was returned to room temperature, and the materials were allowed to react for 5 hours. The reaction solution was combined with 15 ml of a saturated solution of sodium hydrogen carbonate in water and washed therewith, then washed with water, and then with a saturated solution of salt in water, and the organic layer was dried with anhydrous sodium sulfate. After the solvent was distilled out, the residue was purified through a column with a two-fold amount (by weight) of silica gel, giving 1.41 g of the compound represented by (RM-#3) below. Me in the formula represents a methyl group. In Tables 2 and 3 below, this compound represented by formula (RM-#3) is written as "a-2."

[Chem. 107]

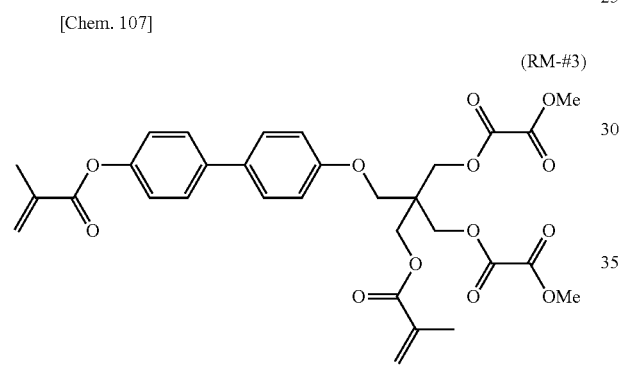

(RM-#3)

$^1$H-NMR (solvent: deuterated chloroform): δ: 1.94 (s, 3H), 2.08 (s, 3H), 3.89 (s, 6H), 4.14 (s, 2H), 4.42 (s, 2H), 4.56 (s, 4H), 5.61 (d, 1H), 5.77 (d, 1H), 6.11 (d, 1H), 6.37 (d, 1H), 6.97 (d, 2H), 7.17 (d, 2H), 7.52 (d, 4H)

(Synthesis of the Compound Represented by Formula (RM-#4))

First, in a reactor equipped with a stirrer, a condenser, and a thermometer and in a nitrogen gas atmosphere, a solution (300 ml) of 100.0 g (303.74 millimoles) of the aforementioned compound represented by formula (6) in tetrahydrofuran was allowed to act on 7.2 g (296.17 millimoles) of magnesium to produce a Grignard reagent. To the resulting mixture, a solution (105 ml) of 35.0 g (99.08 millimoles) of 4-(bromomethyl)-4'-(phenylmethoxy)-1,1'-biphenyl in tetrahydrofuran was slowly added dropwise with the reactor kept at 5° C. or below in an ice-cooled bath. After the addition finished, the reactor was returned to room temperature, and the materials were allowed to react for 5 hours. The reaction solution was combined with 500 ml of a saturated solution of sodium hydrogen carbonate in water and washed therewith, then washed with water, and then with a saturated solution of salt in water, and the organic layer was dried with anhydrous sodium sulfate. After the solvent was distilled out, the residue was purified through a column with a two-fold amount (by weight) of silica gel, giving 27.4 g of the compound represented by formula (11) below.

[Chem. 108]

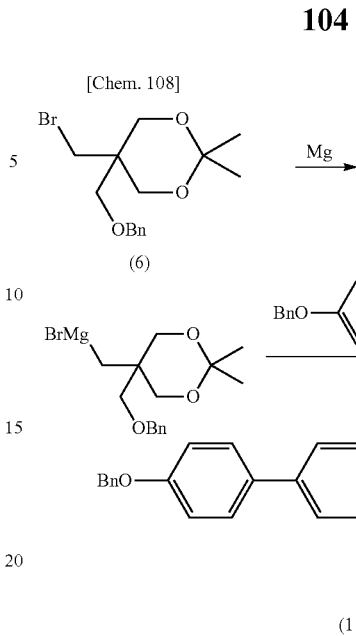

Then the above-described synthesis of the compound represented by formula (3) was done completely in the same way except that the compound represented by formula (2) was replaced with that represented by formula (11). This gave 15.1 g of the compound represented by formula (12) below.

[Chem. 109]

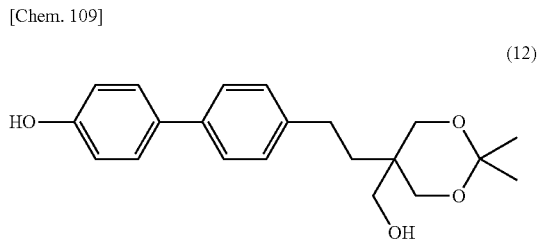

Subsequently, the above-described synthesis of the compound represented by formula (4) was done completely in the same way except that the compound represented by formula (3) was replaced with that represented by formula (12). This gave 14.7 g of the compound represented by formula (13) below.

[Chem. 110]

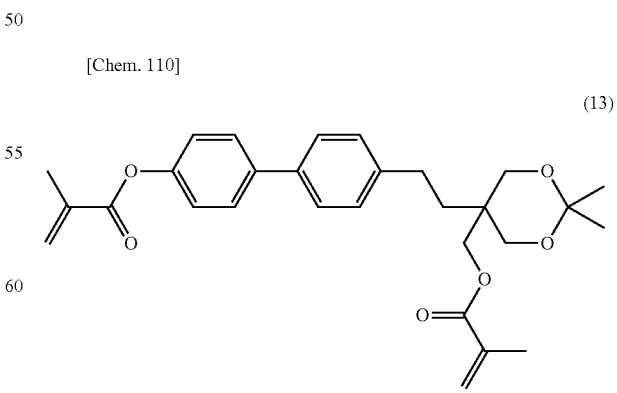

After that, the above-described synthesis of the compound represented by formula (5) was done completely in the same way except that the compound represented by formula (4) was replaced with that represented by formula (13). This gave 12.1 g of the compound represented by formula (14) below.

[Chem. 111]

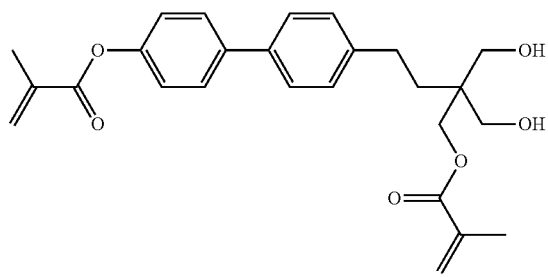

(14)

Then the above-described synthesis of the compound represented by formula (RM-#1) was done completely in the same way except that the compound represented by formula (5) was replaced with that represented by formula (14). This gave 8.2 g of the compound represented by formula (RM-#4) below. In Tables 2 and 3 below, this compound represented by formula (RM-#4) is written as "a-3."

[Chem. 112]

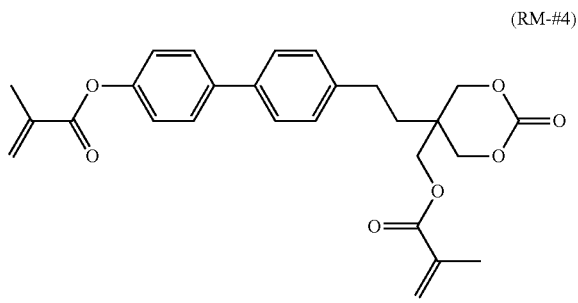

(RM-#4)

$^1$H-NMR (solvent: deuterated chloroform): δ: 1.47 (t, 2H), 1.99 (s, 3H), 2.02 (s, 3H), 2.67 (t, 2H), 3.78 (d, 4H), 4.12 (d, 2H), 6.15 (d, 1H), 6.37 (d, 1H), 6.42 (d, 1H), 6.49 (d, 1H), 7.12 (d, 2H), 7.25 (d, 2H), 7.62 (d, 2H), 7.72 (d, 2H)

(2) Preparation of Polymerizable Compounds B

As polymerizable compounds B, the compounds represented by formulae (b-1) and (b-2) below were prepared. It should be noted that in Tables 2 and 3 below, the compounds represented by formulae (b-1) and (b-2) are written as "b-1" and "b-2."

[Chem. 113]

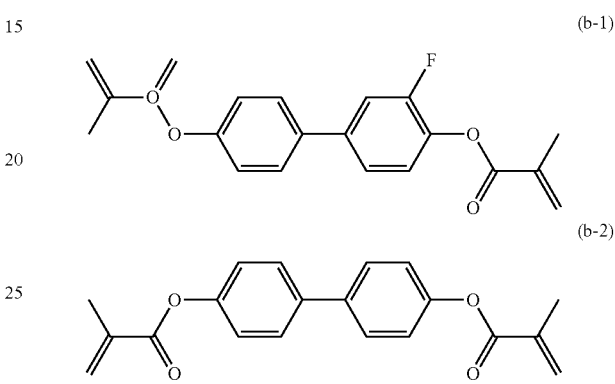

(3) Preparation of Matrix Compositions

Liquid crystal compositions LC-1 to LC-8, to which compound A and/or polymerizable compound B had yet to be added (matrix compositions), were prepared according to Table 1. Then the following characteristics of these matrix compositions were measured. The formula and characteristics of matrix compositions LC-1 to LC-8 are presented in Tables 1 and 2.

$T_{ni}$: Nematic-isotropic liquid phase transition temperature (° C.)

Δn: Refractive-index anisotropy at 25° C.

Δε: Dielectric anisotropy at 25° C.

$γ_1$: Rotational viscosity (mPa·s) at 25° C.

TABLE 1

|  | LC-1 | LC-2 | LC-3 | LC-4 | LC-5 | LC-6 | LC-7 | LC-8 |
|---|---|---|---|---|---|---|---|---|
| 3-Cy-Cy-2 | 18 | 20 | 18.5 | 20 |  |  |  |  |
| 3-Cy-Cy-4 | 8 | 4 |  |  |  |  |  |  |
| 3-Cy-Cy-5 |  |  | 6.75 | 7 |  |  |  |  |
| 5-Cy-Cy-2 |  |  |  |  |  |  |  |  |
| 3-Cy-Cy-V |  |  |  |  | 29 | 43 | 23 | 29 |
| 3-Cy-Cy-V1 |  |  | 10.25 |  |  |  | 10 |  |
| 3-Cy-Ph-O1 |  | 6 |  | 3 |  |  |  |  |
| 3-Ph-Ph-1 | 13 | 12 |  |  | 17 |  | 9 |  |
| 3-Cy-Cy-Ph-1 |  |  | 6 | 7 |  |  |  | 7 |
| 3-Cy-Cy-Ph-3 |  |  |  | 4 |  |  |  | 4 |
| 3-Cy-Ph-Ph-1 |  | 5 |  |  | 7 |  |  |  |
| 3-Cy-Ph-Ph-2 | 6 |  |  |  | 4 |  | 5 |  |
| 5-Cy-Ph-Ph-2 | 4 |  |  |  |  |  |  |  |
| 1V2-Ph-Ph-1 |  |  | 3.75 |  |  |  |  |  |
| 3-Cy-Ph23-O2 |  |  | 11.5 |  |  |  |  |  |
| 3-Ph-Ph23-O2 |  |  | 12 | 10 |  |  | 5 | 10 |
| 3-Cy-Cy-Ph23-1 |  |  | 2.5 |  |  |  |  |  |
| 3-Cy-Cy-Ph23-O1 |  |  | 12 |  |  | 6 |  |  |
| 3-Cy-Cy-Ph23-O2 |  |  |  | 15 |  | 10 |  | 15 |
| 3-Cy-Cy-Ph23-O4 |  |  |  | 15 |  |  |  | 15 |
| 4-Cy-Cy-Ph23-O2 |  |  |  | 10 |  |  |  | 13 |
| 3-Cy-1O-Ph23-O1 | 6 |  |  |  |  |  |  |  |

TABLE 1-continued

|  | LC-1 | LC-2 | LC-3 | LC-4 | LC-5 | LC-6 | LC-7 | LC-8 |
|---|---|---|---|---|---|---|---|---|
| 3-Cy-1O-Ph23-O2 | 7 | 9 |  |  | 6 | 12 | 5 |  |
| 1V-Cy-1O-Ph23-O2 |  |  |  |  |  |  | 6 |  |
| 2-Cy-Cy-1O-Ph23-O2 | 14 |  |  | 12 |  |  |  |  |
| 3-Cy-Cy-1O-Ph23-O2 | 3 | 10 |  | 15 |  |  | 12 |  |
| V-Cy-Cy-1O-Ph23-O2 |  |  |  |  |  |  | 4 |  |
| 1V-Cy-Cy-1O-Ph23-O2 |  | 5 |  |  | 5 |  | 6 |  |
| 2-Cy-Ph-Ph23-O2 |  | 7 | 6 | 5 |  | 7 |  | 5 |
| 3-Cy-Ph-Ph23-O2 |  | 8 | 10.75 | 4 |  | 12 | 5 | 2 |
| 3-Cy-Ph-Ph23-O3 | 6 |  |  |  |  |  |  |  |
| 3-Cy-Ph-Ph23-O4 | 7 | 9 |  |  |  |  |  |  |
| 4-Cy-Ph-Ph23-O3 | 8 |  |  |  |  |  |  |  |
| 3-Ph-Ph23-Ph-2 |  |  |  |  |  | 10 | 5 |  |
| 2-Ph-2-Ph-Ph23-O2 |  |  |  |  |  |  | 5 |  |
| 3-Ph-2-Ph-Ph23-O2 |  | 5 |  |  | 5 |  |  |  |
|  |  |  |  |  |  |  |  |  |
| Total (wt %) | 100 | 100 | 100 | 100 | 100 | 100 | 100 | 100 |
| Tni [° C.] | 73.8 | 76.7 | 74.7 | 111.2 | 74.4 | 79.0 | 72.8 | 110.2 |
| Δn | 0.111 | 0.118 | 0.103 | 0.098 | 0.112 | 0.100 | 0.114 | 0.098 |
| Δε | −3.2 | −3.3 | −3.1 | −3.1 | −2.8 | −3.1 | −3.3 | −3.1 |
| γ1 [mPa·s] | 125 | 132 | 99 | 154 | 105 | 86 | 104 | 135 |

(4) Preparation of the Liquid Crystal Compositions of Examples 1 to 28 and Comparative Examples 1 to 11

The liquid crystal compositions of Examples 1 to 28 were prepared by adding, to a total of 100% by mass of matrix compositions LC-1 to LC-8, a compound represented by any of formulae (RM-#1) to (RM-#4) (compound A) and optionally a compound represented by formula (b-1) or (b-2) (compound B) according to the percentages (% by mass) specified in Tables 3 to 4 below. Likewise, the liquid crystal compositions of Comparative Examples 1 to 11 were prepared by adding a compound represented by formula (b-1) or (b-2) to matrix compositions LC-1 to LC-8 according to the percentage specified in Table 2 below.

(5) Production and Testing of Liquid Crystal Cells and Liquid Crystal Display Elements Liquid crystal cells with a cell gap of 3.5 μm including ITO-coated substrates with a rubbed vertical alignment-inducing polyamide alignment film thereon were filled with the resulting liquid crystal compositions of Examples 1 to 28 and Comparative Examples 1 to 11 by vacuum filling. Then the liquid crystal cells, filled with liquid crystal compositions, were irradiated with ultraviolet radiation for 90 minutes using a fluorescent UV lamp that emits light in the range of 300 to 500 nm, completing liquid crystal display elements. The fluorescent UV lamp was tuned so that the irradiance measured under 313 nm central wavelength conditions would be 3.0 mW/cm².

(Testing of the Voltage Holding Ratio)

The voltage holding ratio (VHR) of the resulting liquid crystal display elements was measured under 1 V, 0.6 Hz, and 60° C. conditions. The display elements were graded A if the measured VHR was 95% or higher, B if it was less than 95% and 90% or more, C if it was less than 90% to 80% or more, or D if it was lower than 80%.

(Testing of Pretilt Angle Formation)

The resulting liquid crystal display elements were irradiated with ultraviolet radiation for 200 seconds under the above irradiation conditions, and the change in the pretilt angle [°] of the liquid crystal display elements was measured before and after that. The measurement process was as follows. First, the pretilt angle of the liquid crystal display element was measured, and this was reported as pretilt angle (initial). Then this liquid crystal display element was irradiated with ultraviolet radiation for 200 seconds while a voltage of 10 V was applied at a frequency of 100 Hz. Then the pretilt angle was measured, and this was reported as pretilt angle (post-UV). The difference of the measured pretilt angle (initial) minus the measured pretilt angle (post-UV) was reported as the change in pretilt angle [°]. The measurement of pretilt angles used SHINTECH's OPTIPRO. The display elements were graded A if the change in pretilt angle [°] was 2.0° or greater, B if it was less than 2.0° and 1.5° or more, C if it was less than 1.5° to 1.0° or more, or D if it was smaller than 1.0°.

(Testing of Storage at Low Temperatures)

A sample for the testing of storage at low temperatures was obtained by weighing out 0.5 g of the liquid crystal composition, which contained compound A and/or polymerizable compound B, into a test tube, degassing the tube for 15 minutes, and then purging it with nitrogen. This sample was stored in a freezer at −20° C. and observed for separation. The liquid crystal compositions were graded ○ if no compound separated out even after 10 days of storage, Δ if the compound(s) separated out in 5 to 9 days, or × if the compound(s) separated out in 5 days. The results of the tests are presented in Table 2.

TABLE 2

|  | Base composition | Compound A Type | Compound A Amount | Polymerizable compound B Type | Polymerizable compound B Amount | Voltage holding ratio | Pretilt angle formation | Storage at low temperatures |
|---|---|---|---|---|---|---|---|---|
| Example 1 | LC-1 | a-1 | 0.4 | b-1 | 0.3 | A | A | ○ |
| Example 2 | LC-2 | a-1 | 0.4 | b-1 | 0.3 | A | A | ○ |
| Example 3 | LC-3 | a-1 | 0.4 | b-1 | 0.3 | A | A | ○ |
| Example 4 | LC-4 | a-1 | 0.4 | b-1 | 0.3 | A | A | ○ |
| Example 5 | LC-5 | a-1 | 0.4 | b-1 | 0.3 | B | A | ○ |
| Example 6 | LC-6 | a-1 | 0.4 | b-1 | 0.3 | A | B | ○ |

TABLE 2-continued

| | Base composition | Compound A Type | Compound A Amount | Polymerizable compound B Type | Polymerizable compound B Amount | Voltage holding ratio | Pretilt angle formation | Storage at low temperatures |
|---|---|---|---|---|---|---|---|---|
| Example 7 | LC-7 | a-1 | 0.4 | b-1 | 0.3 | B | A | ○ |
| Example 8 | LC-8 | a-1 | 0.4 | b-1 | 0.3 | A | B | ○ |
| Example 9 | LC-1 | a-2 | 0.4 | b-1 | 0.3 | A | A | ○ |
| Example 10 | LC-2 | a-2 | 0.4 | b-1 | 0.3 | A | A | ○ |
| Example 11 | LC-3 | a-2 | 0.4 | b-1 | 0.3 | A | A | ○ |
| Example 12 | LC-4 | a-2 | 0.4 | b-1 | 0.3 | A | A | ○ |
| Example 13 | LC-5 | a-2 | 0.4 | b-1 | 0.3 | B | A | ○ |
| Example 14 | LC-6 | a-2 | 0.4 | b-1 | 0.3 | A | B | ○ |
| Example 15 | LC-7 | a-2 | 0.4 | b-1 | 0.3 | B | A | ○ |
| Example 16 | LC-8 | a-2 | 0.4 | b-1 | 0.3 | A | B | ○ |
| Example 17 | LC-4 | a-2 | 0.4 | b-2 | 0.3 | A | A | ○ |
| Example 18 | LC-8 | a-2 | 0.4 | b-2 | 0.3 | A | A | ○ |
| Example 19 | LC-1 | a-1 | 0.4 | — | — | A | A | ○ |
| Example 20 | LC-3 | a-1 | 0.4 | — | — | A | A | ○ |
| Example 21 | LC-5 | a-1 | 0.4 | — | — | A | B | ○ |
| Example 22 | LC-7 | a-1 | 0.4 | — | — | A | B | ○ |
| Example 23 | LC-6 | a-2 | 0.4 | — | — | A | A | ○ |
| Example 24 | LC-6 | a-3 | 0.4 | — | — | A | B | ○ |
| Example 25 | LC-6 | a-4 | 0.4 | — | — | A | A | ○ |
| Example 26 | LC-8 | a-2 | 0.4 | — | — | A | A | ○ |
| Example 27 | LC-8 | a-3 | 0.4 | — | — | A | B | ○ |
| Example 28 | LC-8 | a-4 | 0.4 | — | — | A | A | ○ |
| Comparative Example 1 | LC-1 | — | — | b-1 | 0.3 | B | B | ○ |
| Comparative Example 2 | LC-2 | — | — | b-1 | 0.3 | B | B | ○ |
| Comparative Example 3 | LC-3 | — | — | b-1 | 0.3 | B | B | ○ |
| Comparative Example 4 | LC-4 | — | — | b-1 | 0.3 | B | B | ○ |
| Comparative Example 5 | LC-5 | — | — | b-1 | 0.3 | D | B | ○ |
| Comparative Example 6 | LC-6 | — | — | b-1 | 0.3 | C | C | ○ |
| Comparative Example 7 | LC-7 | — | — | b-1 | 0.3 | D | B | ○ |
| Comparative Example 8 | LC-8 | — | — | b-1 | 0.3 | C | B | ○ |
| Comparative Example 9 | LC-5 | — | — | b-2 | 0.3 | D | B | ○ |
| Comparative Example 10 | LC-6 | — | — | b-2 | 0.3 | C | C | ○ |
| Comparative Example 11 | LC-5 | — | — | b-1 | 0.7 | D | A | × |

As shown in Table 2, the liquid crystal compositions of Examples 1 to 18, containing both compound A and polymerizable compound B, were improved or comparable in the voltage holding ratio and the change in pretilt angle, and were good in storage at low temperatures at the same time, compared with those of Comparative Examples 1 to 10, made with the same matrix compositions and containing polymerizable compound B but containing no compound A, demonstrating better performance. When the liquid crystal compositions of Examples 1 and 2 and that of Comparative Example 1, made with the same matrix composition, were contrasted, Examples 1 and 2 were better than Comparative Example 1 in both the voltage holding ratio and the change in pretilt angle. As stated, the liquid crystal compositions of Examples 1 and 2 contained compound A, represented by general formula (Y) and having a substructure represented by general formula (Y-1) or (Y-2). This, the inventors believe, reduced the impact of impurities present in the liquid crystal cell.

A comparison between Examples 12 and 17 and that between Examples 16 and 18, furthermore, revealed that when polymerizable compound B, used in combination with compound A, is the compound represented by formula (b-2), too, the advantages provided are the same as when polymerized compound B is the compound represented by (b-1).

A contrasting between the liquid crystal compositions of Examples 1 to 18, in which the total percentage of compound A and polymerizable compound B was 0.7% by mass, those of Comparative Examples 1 to 10, which contained no compound A but contained 0.3% by mass polymerizable compound B, and that of Comparative Example 11, which contained no compound A but contained 0.7% by mass polymerizable compound B, furthermore, revealed that the improvements in the three of the voltage holding ratio, the change in pretilt angle, and storage at low temperatures owed not to an increase in the total percentage of compound A and polymerizable compound B but to the addition of compound A. As can be seen from the results with the liquid crystal compositions of Examples 19 to 28, furthermore, the presence of compound A allows these compositions to achieve a high voltage holding ratio, a large change in pretilt angle, and good storage at low temperatures, even without polymerizable compound B.

As compounds A, furthermore, the compounds represented by formulae (RM-#5) to (RM-#9) below were synthesized. The compounds' structure was identified by 1H-NMR.

(Synthesis of the Compound Represented by Formula (RM-#5))

First, the above-described synthesis of the compound represented by formula (7) was done completely in the same way except that 4'-benzyloxy-1,1'-biphenyl-4-ol was replaced with 2-ethyl-4'-[(tetrahydro-2H-pyran-2-yl)oxy]-1,1'-biphenyl-4-ol. This gave 20.2 g of the compound represented by formula (15) below.

[Chem. 114]

(15)

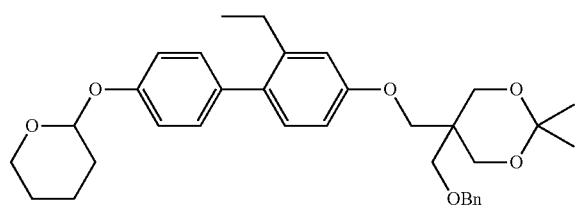

Subsequently, the above-described synthesis of the compound represented by formula (3) was done completely in the same way except that the compound represented by formula (2) was replaced with that represented by formula (15). This gave 13.1 g of the compound represented by formula (16) below.

[Chem. 115]

(16)

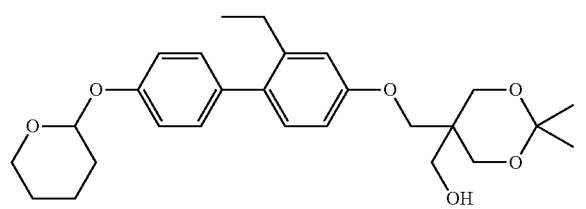

After that, the above-described synthesis of the compound represented by formula (4) was done completely in the same way except that the compound represented by formula (3) was replaced with that represented by formula (16). This gave 12.5 g of the compound represented by formula (17) below.

[Chem. 116]

(17)

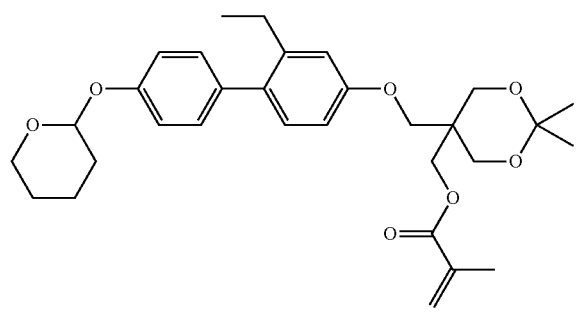

To a reactor with a stirrer, a heater, and a thermometer were added 11.0 g of the resulting compound represented by formula (17), 1.1 g of pyridinium p-toluenesulfonate, 33 ml of acetone, and 33 ml of ethanol. The materials were allowed to react for 3 hours at 50° C. in a nitrogen gas atmosphere. The reaction solution was combined with 50 ml of ethyl acetate, washed with water and then with a saturated solution of salt in water, and the organic layer was dried with anhydrous sodium sulfate. After the solvent was distilled out, the residue was purified through a column with a two-fold amount (by weight) of silica gel, giving 8.9 g of the compound represented by formula (18) below.

[Chem. 117]

(18)

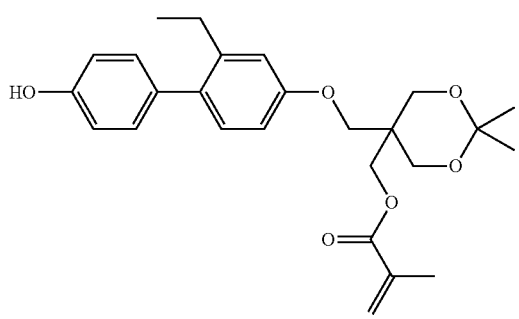

After that, the above-described synthesis of the compound represented by formula (4) was done completely in the same way except that the compound represented by formula (3) was replaced with that represented by formula (18). This gave 9.1 g of the compound represented by formula (19) below.

[Chem. 118]

(19)

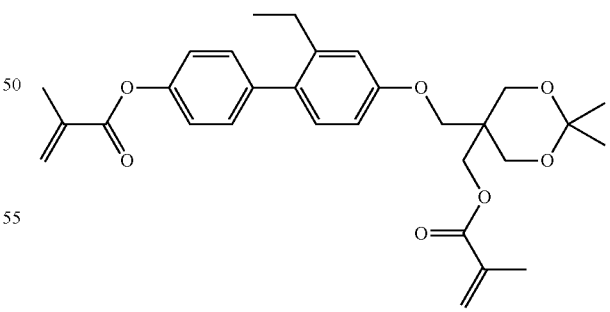

After that, the above-described synthesis of the compound represented by formula (5) was done completely in the same way except that the compound represented by formula (4) was replaced with that represented by formula (19). This gave 7.6 g of the compound represented by formula (20) below.

[Chem. 119]

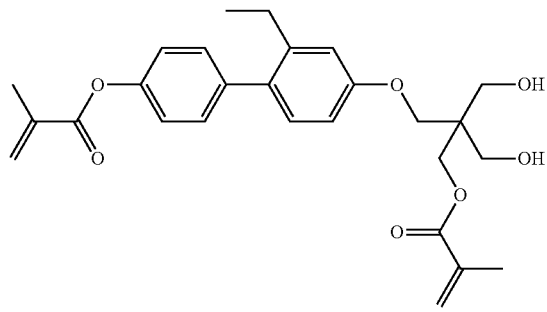

(20)

After that, the above-described synthesis of the compound represented by formula (RM-#1) was done completely in the same way except that the compound represented by formula (5) was replaced with that represented by formula (20). This gave 1.8 g of the compound represented by formula (RM-#5) below. In Table 3 below, this compound represented by formula (RM-#5) is written as "a-5."

[Chem. 120]

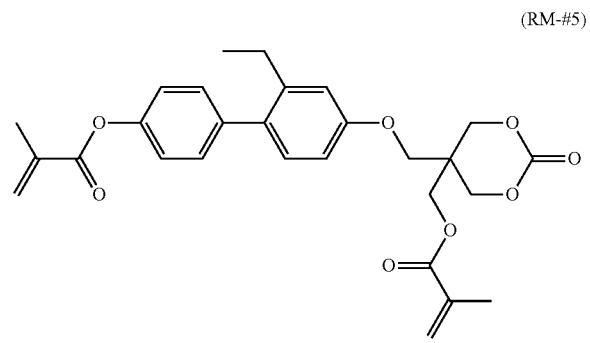

(RM-#5)

1H-NMR (solvent: deuterated chloroform): δ: 1.09 (t, 3H), 1.95 (s, 3H), 2.08 (s, 3H), 2.56 (q, 2H), 4.07 (s, 2H), 4.38 (s, 2H), 4.43-4.56 (dd, 4H), 5.64 (m, 1H), 5.76 (m, 1H), 6.11 (s, 1H), 6.36 (s, 1H), 6.73-6.83 (m, 2H), 7.12-7.16 (m, 3H), 7.25-7.28 (m, 2H)

(Synthesis of the Compound Represented by Formula (RM-#6))

To a reactor equipped with a stirrer, a condenser, and a thermometer were added 4.3 g (9.76 millimoles) of the resulting compound represented by formula (18), 1.8 g (17.79 millimoles) of triethylamine, and 43 ml of methylene chloride. With the reactor kept at 5° C. or below in an ice-cooled bath, 1.3 g (14.36 millimoles) of acrylic acid chloride were slowly added dropwise in a nitrogen gas atmosphere. After the addition finished, the reactor was returned to room temperature, and the materials were allowed to react for 5 hours. The reaction solution was combined with 50 ml of a saturated solution of ammonium chloride in water and washed therewith, then washed with water, and then with a saturated solution of salt in water, and the organic layer was dried with anhydrous sodium sulfate. After the solvent was distilled out, the residue was purified through a column with a two-fold amount (by weight) of silica gel, giving 4.05 g of the compound represented by formula (21) below.

[Chem. 121]

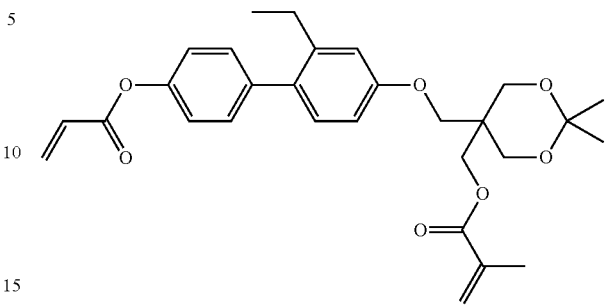

(21)

After that, the above-described synthesis of the compound represented by formula (5) was done completely in the same way except that the compound represented by formula (4) was replaced with that represented by formula (21). This gave 2.4 g of the compound represented by formula (22) below.

[Chem. 122]

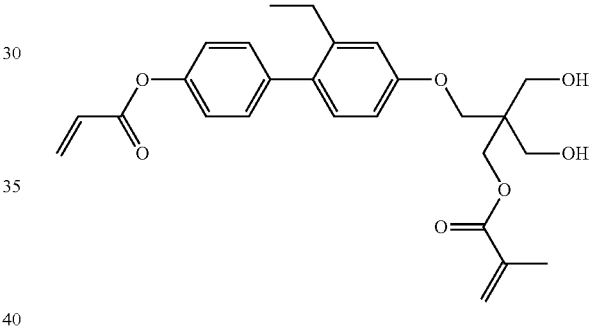

(22)

After that, the above-described synthesis of the compound represented by formula (RM-#1) was done completely in the same way except that the compound represented by formula (5) was replaced with that represented by formula (22). This gave 1.1 g of the compound represented by formula (RM-#6) below. In Table 3 below, this compound represented by formula (RM-#6) is written as "a-6."

[Chem. 123]

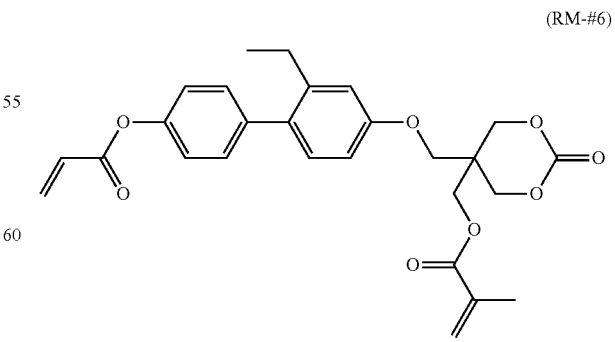

(RM-#6)

1H-NMR (solvent: deuterated chloroform): δ: 1.08 (t, 3H), 2.07 (s, 3H), 2.55 (q, 2H), 4.06 (s, 2H), 4.39 (s, 2H), 4.44-4.57 (dd, 4H), 5.62 (m, 1H), 5.75-5.92 (m, 2H), 6.10 (s, 1H), 6.34 (s, 1H), 6.71-6.81 (m, 2H), 7.13-7.16 (m, 3H), 7.25-7.27 (m, 2H)

(Synthesis of the Compound Represented by Formula (RM-#7))

The above-described synthesis of the compound represented by formula (21) was done completely in the same way except that the compound represented by formula (18) was replaced with that represented by formula (16). This gave 29.5 g of the compound represented by formula (23) below.

[Chem. 124]

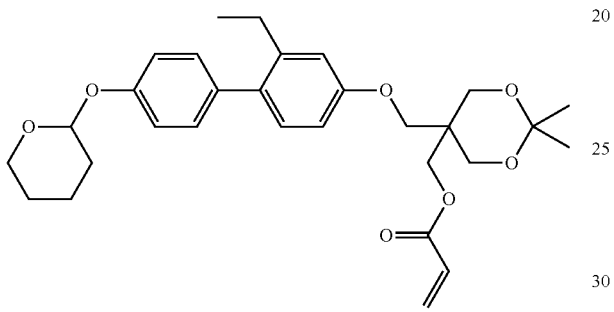

(23)

The above-described synthesis of the compound represented by formula (18) was done completely in the same way except that the compound represented by formula (17) was replaced with that represented by formula (23). This gave 11.3 g of the compound represented by formula (24) below.

[Chem. 125]

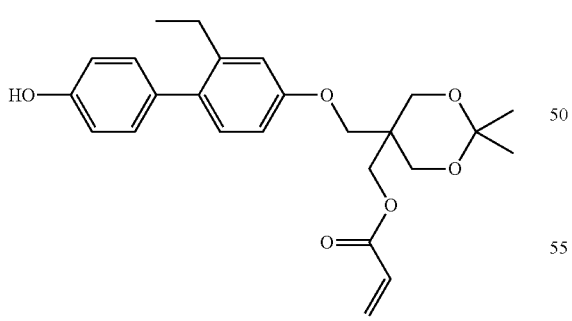

(24)

After that, the above-described synthesis of the compound represented by formula (4) was done completely in the same way except that the compound represented by formula (3) was replaced with that represented by formula (24). This gave 6.7 g of the compound represented by formula (25) below.

[Chem. 126]

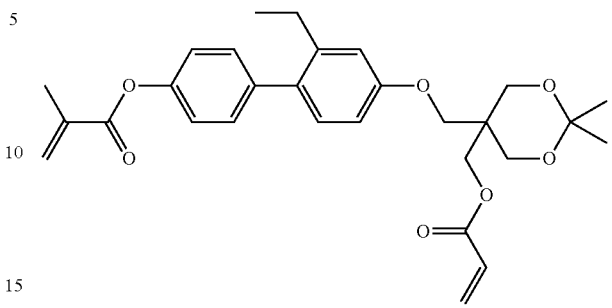

(25)

After that, the above-described synthesis of the compound represented by formula (5) was done completely in the same way except that the compound represented by formula (4) was replaced with that represented by formula (25). This gave 5.2 g of the compound represented by formula (26) below.

[Chem. 127]

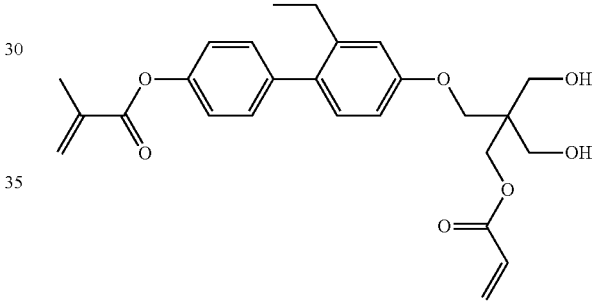

(26)

After that, the above-described synthesis of the compound represented by formula (RM-#1) was done completely in the same way except that the compound represented by formula (5) was replaced with that represented by formula (26). This gave 3.0 g of the compound represented by formula (RM-#7) below. In Table 3 below, this compound represented by formula (RM-#5) is written as "a-7."

[Chem. 128]

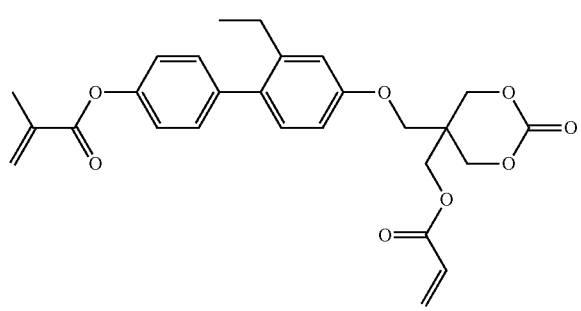

(RM-#7)

1H-NMR (solvent: deuterated chloroform): δ: 1.09 (t, 3H), 2.06 (s, 3H), 2.55 (q, 2H), 4.07 (s, 2H), 4.37 (s, 2H), 4.42-4.55 (dd, 4H), 5.64-5.76 (m, 2H), 6.10 (s, 1H), 6.36 (s, 1H), 6.71-6.79 (m, 3H), 7.11-7.16 (m, 3H), 7.25-7.27 (m, 2H)

(Synthesis of the Compound Represented by Formula (RM-#8))

The above-described synthesis of the compound represented by formula (21) was done completely in the same way except that the compound represented by formula (18) was replaced with that represented by formula (24). This gave 5.1 g of the compound represented by formula (27) below.

[Chem. 129]

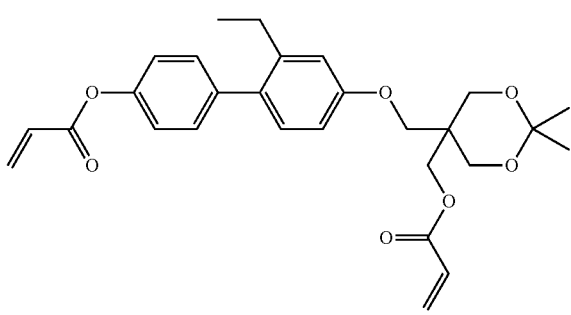

(27)

After that, the above-described synthesis of the compound represented by formula (5) was done completely in the same way except that the compound represented by formula (4) was replaced with that represented by formula (27). This gave 4.6 g of the compound represented by formula (28) below.

[Chem. 130]

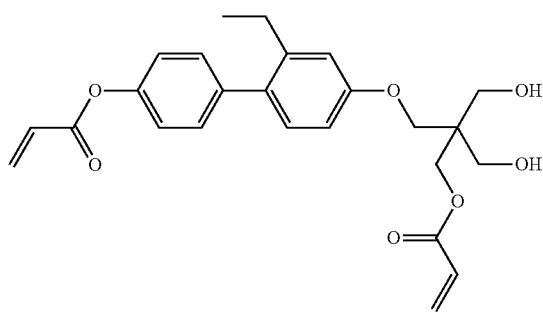

(28)

After that, the above-described synthesis of the compound represented by formula (RM-#1) was done completely in the same way except that the compound represented by formula (5) was replaced with that represented by formula (28). This gave 2.9 g of the compound represented by formula (RM-#8) below. In Table 3 below, this compound represented by formula (RM-#8) is written as "a-8."

[Chem. 131]

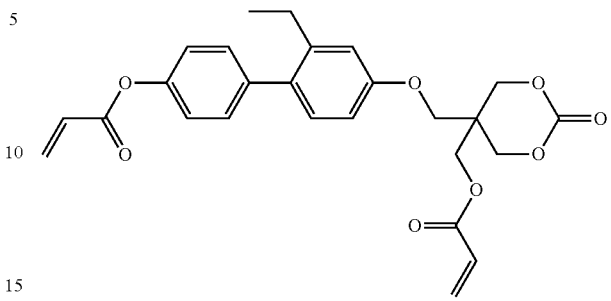

(RM-#8)

1H-NMR (solvent: deuterated chloroform): δ: 1.09 (t, 3H), 2.56 (q, 2H), 4.07 (s, 2H), 4.38 (s, 2H), 4.43-4.56 (dd, 4H), 5.64-5.75 (m, 3H), 6.11-6.35 (m, 2H), 6.73-6.83 (m, 2H), 7.12-7.16 (m, 3H), 7.24-7.29 (m, 3H)

(Synthesis of the Compound Represented by Formula (RM-#9))

First, the above-described synthesis of the compound represented by formula (7) was done completely in the same way except that 4'-benzyloxy-1,1'-biphenyl-4-ol was replaced with 4'-(3-hydroxypropyl)-[1,1'-biphenyl]-4-ol. This gave 7.2 g of the compound represented by formula (29) below.

[Chem. 132]

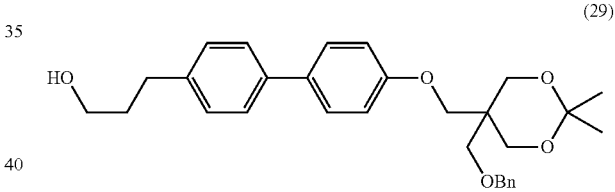

(29)

Subsequently, the above-described synthesis of the compound represented by formula (3) was done completely in the same way except that the compound represented by formula (2) was replaced with that represented by formula (29). This gave 5.1 g of the compound represented by formula (30) below.

[Chem. 133]

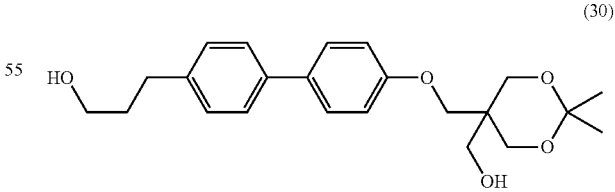

(30)

After that, the above-described synthesis of the compound represented by formula (4) was done completely in the same way except that the compound represented by formula (3) was replaced with that represented by formula (30). This gave 9.4 g of the compound represented by formula (31) below.

[Chem. 134]

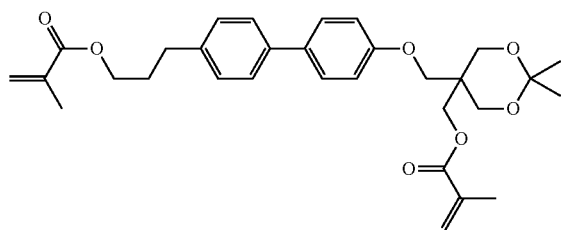
(31)

After that, the above-described synthesis of the compound represented by formula (5) was done completely in the same way except that the compound represented by formula (4) was replaced with that represented by formula (31). This gave 2.2 g of the compound represented by formula (32) below.

[Chem. 135]

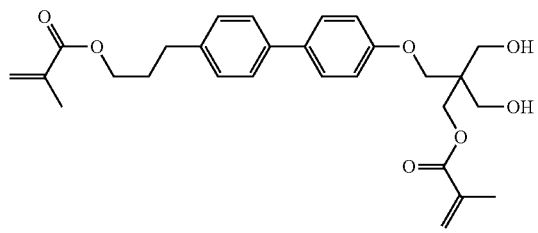
(32)

After that, the above-described synthesis of the compound represented by formula (RM-#1) was done completely in the same way except that the compound represented by formula (5) was replaced with that represented by formula (32). This gave 1.7 g of the compound represented by formula (RM-#9) below. In Table 3 below, this compound represented by formula (RM-#5) is written as "a-9."

[Chem. 136]

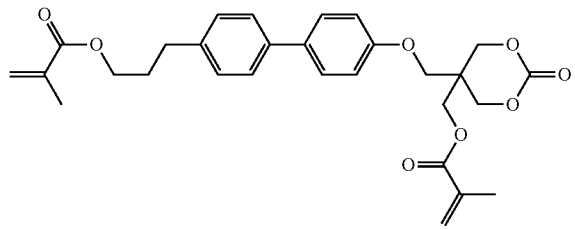
(RM-#9)

$^1$H-NMR (solvent: deuterated chloroform): δ: 1.94 (dd, 2H), 2.04 (s, 6H), 2.78 (d, 2H), 3.91 (d, 4H), 4.01 (d, 2H), 4.18 (d, 2H), 4.21 (d, 2H), 5.62 (m, 1H), 5.77 (m, 1H), 6.09 (s, 1H), 6.32 (s, 1H), 6.70-6.85 (m, 3H), 7.10-7.14 (m, 3H), 7.24-7.29 (m, 2H)

Examples 29 to 52

Liquid crystal compositions were prepared and tested in the same way as in Examples 1 to 28, demonstrating that they provide the same advantages. The results are presented in Table 3.

TABLE 3

| | Base composition | Compound A | | Polymerizable compound B | | Voltage holding ratio | Pretilt angle formation | Storage at low temperatures |
|---|---|---|---|---|---|---|---|---|
| | | Type | Amount | Type | Amount | | | |
| Example 29 | LC-5 | a-1 | 0.2 | b-1 | 0.3 | B | A | ○ |
| Example 30 | LC-5 | a-5 | 0.2 | b-1 | 0.3 | B | A | ○ |
| Example 31 | LC-5 | a-6 | 0.2 | b-1 | 0.3 | B | A | ○ |
| Example 32 | LC-5 | a-7 | 0.2 | b-1 | 0.3 | B | A | ○ |
| Example 33 | LC-5 | a-8 | 0.2 | b-1 | 0.3 | B | A | ○ |
| Example 34 | LC-5 | a-9 | 0.2 | b-1 | 0.3 | B | A | ○ |
| Example 35 | LC-6 | a-1 | 0.2 | b-1 | 0.3 | A | B | ○ |
| Example 36 | LC-6 | a-5 | 0.2 | b-1 | 0.3 | A | B | ○ |
| Example 37 | LC-6 | a-6 | 0.2 | b-1 | 0.3 | A | B | ○ |
| Example 38 | LC-6 | a-7 | 0.2 | b-1 | 0.3 | A | B | ○ |
| Example 39 | LC-6 | a-8 | 0.2 | b-1 | 0.3 | A | B | ○ |
| Example 40 | LC-6 | a-9 | 0.2 | b-1 | 0.3 | A | B | ○ |
| Example 41 | LC-5 | a-1 | 0.2 | — | — | A | B | ○ |
| Example 42 | LC-5 | a-5 | 0.2 | — | — | A | B | ○ |
| Example 43 | LC-5 | a-6 | 0.2 | — | — | A | B | ○ |
| Example 44 | LC-5 | a-7 | 0.2 | — | — | A | B | ○ |
| Example 45 | LC-5 | a-8 | 0.2 | — | — | A | B | ○ |
| Example 46 | LC-5 | a-9 | 0.2 | — | — | A | B | ○ |
| Example 47 | LC-8 | a-1 | 0.2 | — | — | A | B | ○ |
| Example 48 | LC-8 | a-5 | 0.2 | — | — | A | B | ○ |
| Example 49 | LC-8 | a-6 | 0.2 | — | — | A | B | ○ |
| Example 50 | LC-8 | a-7 | 0.2 | — | — | A | B | ○ |
| Example 51 | LC-8 | a-8 | 0.2 | — | — | A | B | ○ |
| Example 52 | LC-8 | a-9 | 0.2 | — | — | A | B | ○ |

REFERENCE SIGNS LIST

1 ... Liquid crystal display element
2 ... First substrate
3 ... Second substrate
4 ... Liquid crystal phase
5 ... Pixel-electrode layer
6 ... Common-electrode layer
7 ... First polarizer
8 ... Second polarizer
9 ... Color filter

The invention claimed is:

1. A liquid crystal composition comprising at least one compound A and at least one compound C, wherein the at least one compound A is represented by general formula (Y) below, and the at least one compound C is represented by general formula (II) below,

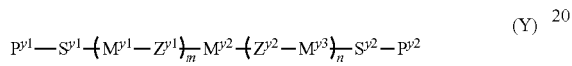 (Y)

in general formula (Y), $S^{y1}$ and $S^{y2}$ each independently represent a single bond, a linear C1 to C12 alkylene group or a branched C2 to C12 alkylene group, optionally with a hydrogen atom or hydrogen atoms in the alkylene group substituted by a halogen atom, a cyano group, or a nitro group, optionally with a —$CH_2$— or —$CH_2$-s in the alkylene group substituted with —CH=CH—, —C≡C—, —CO—, —COO—, —OCO—, —OCOO—, —O—, —NH—, or —S—, although without two or more —O-s consecutively next to each other, $M^{y1}$, $M^{y2}$, and $M^{y3}$ each independently represent a divalent aromatic group, a divalent alicyclic group, a divalent heterocyclic compound group, a divalent fused-ring system, or a divalent fused-polycyclic system, optionally with a hydrogen atom or hydrogen atoms in the ring structure substituted with $L^{y1}$, $L^{y1}$ represents $P^{y3}$—$S^{y3}$—, a halogen atom, a cyano group, a nitro group, a linear C1 to C30 alkyl group or a branched C3 to C30 alkyl group, optionally with a hydrogen atom or hydrogen atoms in the alkyl group substituted by a halogen atom, a cyano group, or a nitro group, optionally with a —$CH_2$— or —$CH_2$-s in the alkyl group substituted with —CH=CH—, —C≡C—, —CO—, —COO—, —OCO—, —OCOO—, —O—, —NH—, or —S—, although without two or more —O-s consecutively next to each other, and if there are a plurality of $L^{y1}$s, the $L^{y1}$s may be the same or different, $P^{y1}$, $P^{y2}$, and $P^{y3}$ represent polymerizable groups, $S^{y3}$ represents a single bond, a linear C1 to C12 alkylene group or a branched C2 to C12 alkylene group, optionally with a hydrogen atom or hydrogen atoms in the alkylene group substituted by a halogen atom, a cyano group, or a nitro group, optionally with a —$CH_2$— or —$CH_2$-s in the alkylene group substituted with —CH=CH—, —C≡C—, —CO—, —COO—, —OCO—, —OCOO—, —O—, —NH—, or —S—, although without two or more —O-s consecutively next to each other, $Z^{y1}$ and $Z^{y2}$ each independently represent a single bond, —$C_2H_4$—, —$C_4H_8$—, —$C_3H_6$—, —$OCH_2$—, —$CH_2O$—, —CO—, —COO—, —OCO—, —OCOOCH_2$—, —$CH_2OCOO$—, —$OCH_2CH_2O$—, —CH=CRa—COO—, —CH=CRa—OCO—, —COO—CRa=CH—, —OCO—CRa=CH—, —COO—CRa=CH—COO—, —COO—CRa=CH—OCO—, —OCO—CRa=CH—COO—, —OCO—CRa50 CH—OCO—, —$COOC_2H_4$—, —$OCOC_2H_4$—, —$C_2H_4OCO$—, —$CH_2OCO$—, —$COOCH_2$—, —$OCOCH_2$—, —CH=CH—, —CF=CF—, —CF=CH—, —CH=CF—, —$CF_2O$—, —$OCF_2$—, —$CF_2CH_2$—, —$CH_2CF_2$—, —$CF_2CF_2$—, or —C≡C—, in the formulae, Ra at each occurrence independently represents a hydrogen atom or a C1 to C4 alkyl group, m and n each independently represent an integer of 0 to 4, with the proviso that m+n is 0 to 6, and if $S^{y1}$, $S^{y2}$, or $L^{y1}$ is a C1 to C12 alkylene or alkyl group, one or more —$CH_2$-s therein are substituted with a substructure represented by general formula (A-1) below

 (A-1)

in general formula (A-1), $S^{y4}$ and $S^{y5}$ each independently represent a single bond, a C1 to C12 linear alkylene group or a branched C2 to C12 alkylene group, optionally with a hydrogen atom or hydrogen atoms in the alkylene group substituted by a halogen atom, a cyano group, or a nitro group, optionally with a —$CH_2$— or —$CH_2$-s in the alkylene group substituted with —CH=CH—, —C≡C—, —CO—, —COO—, —OCO—, —OCOO—, —O—, —NH—, or —S—, although without two or more —O-s consecutively next to each other, and $K^{i1}$ at each occurrence independently represents a group represented by general formula (K-1) or (K-2) below

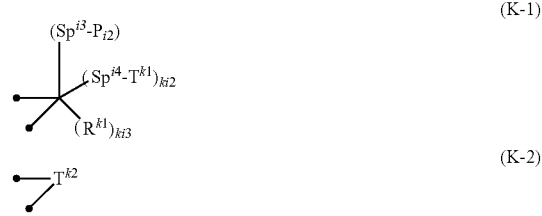

in general formula (K-1), $Sp^{i3}$ and $Sp^{i4}$ each independently represent a single bond, a linear C1 to C20 alkylene group, a branched C2 to C20 alkylene group, a linear C1 to C20 halogenated alkylene group or a branched C2 to C20 halogenated alkylene group, optionally with a —$CH_2$— or —$CH_2$-s in the alkylene or halogenated alkylene group substituted with —CH=CH—, —C≡C—, or —O— without two —O-s consecutively next to each other, $P^{i2}$ represents a polymerizable group, $R^{k1}$ at each occurrence independently represents a hydrogen atom, a linear C1 to C6 alkyl group or a branched C3 to C6 alkyl group, optionally with one —$CH_2$— in the alkyl group, or nonadjacent two or more —$CH_2$-s in the alkyl group, substituted with —O—, ki1 and ki3 each independently represent 0 or 1, and ki2 represents 1 or 2, with the proviso that ki1+ki2+ki3 is 2, and $T^{k1}$ at each occurrence independently represents a group represented by any of general formulae (T-1) to (T-10)

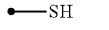 (T-1)

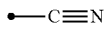 (T-2)

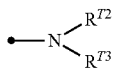 (T-3)

—SH (T-4)

—C≡N (T-5)

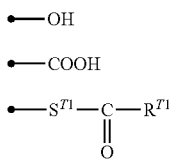 (T-6)

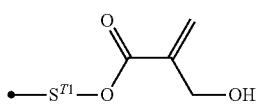 (T-7)

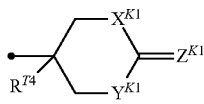 (T-8)

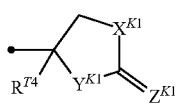 (T-9)

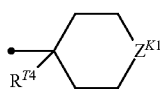 (T-10)

in general formulae (T-1) to (T-10), $S^{T1}$ at each occurrence independently represents a single bond, a linear C1 to C15 alkylene group, a branched C2 to C15 alkylene group, a linear C2 to C18 alkenylene group or a branched C3 to C18 alkenylene group, optionally with a —CH$_2$— or —CH$_2$-s in the alkylene or alkenylene group substituted by —O—, —COO—, —C(=O)—, or —OCO— unless oxygen atoms come consecutively next to each other, $R^{T1}$ at each occurrence independently represents a C1 to C5 alkyl group, optionally with a —CH$_2$— or —CH$_2$-s in the alkyl group substituted by —O—, —COO—, —C(=O)—, or —OCO— in such a manner that oxygen atoms are not consecutively next to each other, and $R^{T2}$, $R^{T3}$, and $R^{T4}$ each independently represent a hydrogen atom or a C1 to C12 alkyl group, optionally with a —CH$_2$— or —CH$_2$-s in the alkyl group substituted by —O—, —COO—, —C(=O)—, or —OCO— unless oxygen atoms come consecutively next to each other, and in general formula (K-2), $T^{k2}$ at each occurrence independently represents a group represented by any of general formulae (T-11) to (T-13)

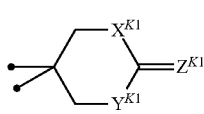 (T-11)

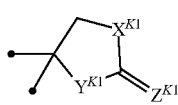 (T-12)

 (T-13)

in general formulae (T-11) to (T-13), $X^{K1}$ and $Y^{K1}$ each independently represent —CH$_2$—, an oxygen atom, or a sulfur atom, and $Z^{K1}$ at each occurrence independently represents an oxygen atom or a sulfur atom, the black dots in the formulae represent bonds, or one or more hydrogen atoms in $S^{y1}$, $S^{y2}$ $M^{y1}$, $M^{y2}$, $M^{y3}$, or $L^{y1}$ are substituted with a substructure represented by general formula (A-2) below

 (A-2)

in general formula (A-2), $S^{y6}$ represents a single bond, a linear C1 to C12 alkylene group or a branched C2 to C12 alkylene group, optionally with a hydrogen atom or hydrogen atoms in the alkylene group substituted by a halogen atom, a cyano group, or a nitro group, optionally with a —CH$_2$— or —CH$_2$-s in the alkylene group substituted with —CH=CH—, —C≡C—, —CO—, —COO—, —OCO—, —OCOO—, —O—, —NH—, or —S—, although without two or more —O-s consecutively next to each other, $T^{k3}$ represents a group represented by any of general formulae (T-1) to (T-13) and (T-14) to (T-24)

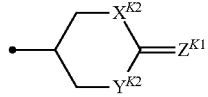 (T-14)

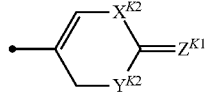 (T-15)

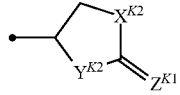 (T-16)

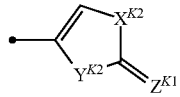 (T-17)

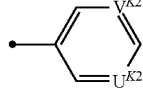 (T-18)

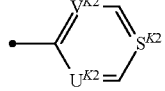 (T-19)

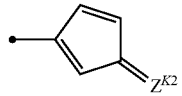 (T-20)

-continued

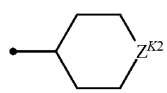
(T-21)

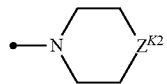
(T-22)

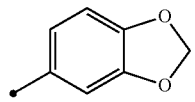
(T-23)

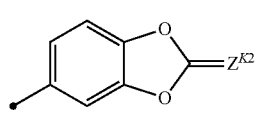
(T-24)

in general formulae (T-14) to (T-24), $X^{K2}$ and $Y^{K2}$ each independently represent —CH$_2$—, an oxygen atom, or a sulfur atom, $Z^{K2}$ at each occurrence independently represents an oxygen atom or a sulfur atom, and $U^{K2}$, $V^{K2}$, and $S^{K2}$ each independently represent a methine group or a nitrogen atom, the black dot in the formulae represents a bond, and ki4 is 1 to 3,

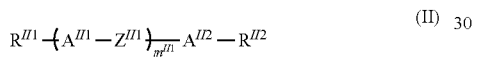
(II)

in general formula (II), $R^{II1}$ represents a C1 to C10 alkyl group or a C2 to C10 alkenyl group, optionally with one —CH$_2$— in the alkyl group, or each of nonadjacent two or more —CH$_2$-s in the alkyl group independently, substituted by —CH=CH—, —C≡C—, —O— —CO—, —COO—, or —OCO— unless oxygen atoms come consecutively next to each other, $R^{II2}$ represents a hydrogen atom, a halogen atom, a cyano group, a C1 to C10 alkyl group, or a C2 to C10 alkenyl group, optionally with one —CH$_2$— in the alkyl group, or each of nonadjacent two or more —CH$_2$-s in the alkyl group independently, substituted by —CH=CH—, —C≡C—, —O—, —CO—, —COO—, or —OCO— unless oxygen atoms come consecutively next to each other, optionally with one or two or more hydrogen atoms in the alkyl group substituted with a halogen atom, with the proviso that at least one of $R^{II1}$ or $R^{II2}$ represents a C2 to C10 alkenyl group, $A^{II1}$ and $A^{II2}$ each independently represent a group selected from the group consisting of:

(a) a 1,4-cyclohexylene group, one —CH$_2$— or two or more nonadjacent —CH$_2$—S present in the group may be replaced by —O— unless oxygen atoms come consecutively next to each other;

(b) a 1,4-phenylene group, one —CH= or two or more nonadjacent —CH=s present in the group may be replaced by —N=; and (c) a 2,6-naphthalenediyl, 1,2,3,4-tetrahydronaphthalene-2,6-diyl, or decahydronaphthalene-2,6-diyl group, one or two or more —CH=s present in the group may be replaced by —N=, optionally with the groups (a), (b), and (c) each independently substituted with a cyano group or a halogen atom, $Z^{II1}$ represents a single bond, —CH$_2$CH$_2$—, —(CH$_2$)$_4$—, —OCH$_2$—, —CH$_2$O—, —COO—, —OCO—, —OCF$_2$—, —CF$_2$O—, —CH=N—N—CH—, —CH=CH—, —CF=CF—, or —C≡C—, and $m^{II1}$ represents 1, 2, 3, or 4, and if $m^{II1}$ represents 2, 3, or 4, the plurality of $A^{II1}$s may be identical or different, and the plurality of $Z^{II1}$s may be identical or different, in general formula (II), any compound represented by general formula (Y) or (P) is excluded.

2. The liquid crystal composition according to claim 1, wherein $M^{y1}$, $M^{y2}$, and $M^{y3}$ in general formula (Y) each independently represent a group selected from the group consisting of formulae (V-1) to (V-21) below

(V-1)

(V-2)

(V-3)

(V-4)

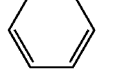
(V-5)

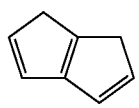
(V-6)

(V-7)

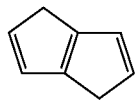
(V-8)

(V-9)

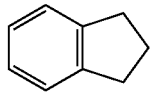
(V-10)

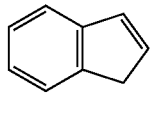
(V-11)

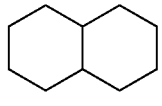
(V-12)

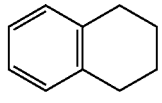

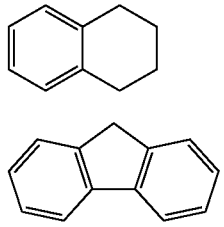

-continued

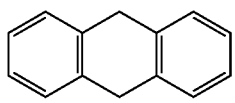 (V-13)

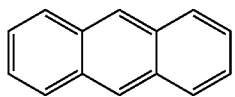 (V-14)

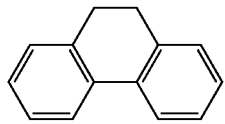 (V-15)

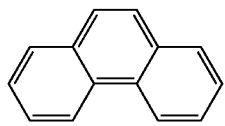 (V-16)

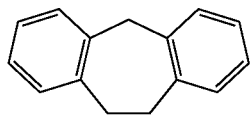 (V-17)

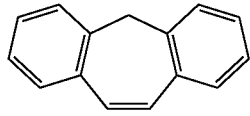 (V-18)

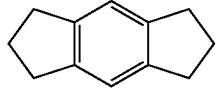 (V-19)

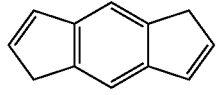 (V-20)

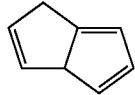 (V-21)

in the formulae, the group may have a bond at any position, optionally with any —CH= at each occurrence independently replaced by —N=, optionally with —CH$_2$— at each occurrence independently replaced by —O—, —S—, —NR$^0$—, in the formula, R$^0$ represents a hydrogen atom or a C1 to C20 alkyl group, —CS—, or —CO—, although no —O—O— linkage is included, optionally with the groups substituted with L$^{y1}$.

3. The liquid crystal composition according to claim 1, wherein P$^{y1}$, P$^{y2}$, P$^{y3}$, and P$^{i2}$ in general formula (Y) each independently represent a substituent selected from the group consisting of formulae (YP-1) to (YP-16) below

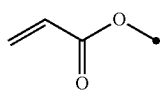 (YP-1)

-continued

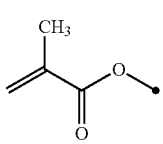 (YP-2)

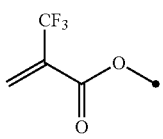 (YP-3)

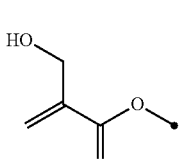 (YP-4)

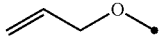 (YP-5)

(YP-6)

(YP-7)

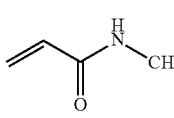 (YP-8)

(YP-9)

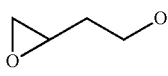 (YP-10)

(YP-11)

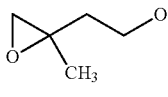 (YP-12)

 (YP-13)

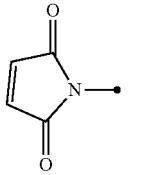 (YP-14)

-continued

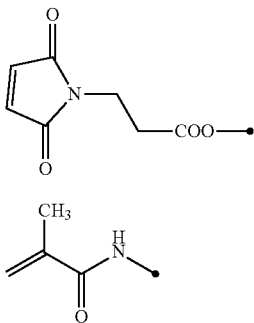
(YP-15)

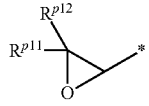
(YP-16)

in the formulae, the black dot represents a bond with $S^{y1}$, $S^{y2}$, $S^{y3}$, or $Sp^{i3}$.

4. The liquid crystal composition according to claim 1, wherein m+n in general formula (Y) is 1 or 2.

5. The liquid crystal composition according to claim 1, wherein at least one of $S^{y1}$ or $S^{y2}$ in general formula (Y) is a single bond.

6. The liquid crystal composition according to claim 1, further comprising at least one polymerizable compound B, wherein the at least one polymerizable compound B is different from the at least one compound A.

7. The liquid crystal composition according to claim 6, wherein the at least one polymerizable compound is a compound represented by general formula (P) below

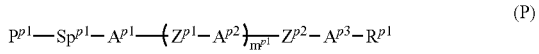
(P)

in general formula (P), $R^{p1}$ represents a hydrogen atom, a fluorine atom, a cyano group, a C1 to C15 alkyl group, or $-Sp^{p2}-P^{p2}$, optionally with one $-CH_2-$ in the alkyl group, or each of nonadjacent two or more $-CH_2$-s in the alkyl group independently, substituted by $-CH=CH-$, $-C\equiv C-$, $-O-$, $-CO-$, $-COO-$, or $-OCO-$, optionally with one or two or more hydrogen atoms in the alkyl group substituted with a cyano group, a fluorine atom, or a chlorine atom, $P^{p1}$ and $P^{p2}$ each independently represent any of general formulae ($P^{p1}$-1) to ($P^{p1}$-9)

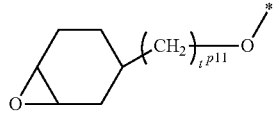
($P^{p1}$-1)

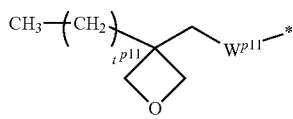
($P^{p1}$-2)

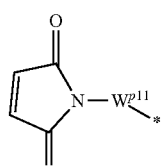
($P^{p1}$-3)

($P^{p1}$-4)

($P^{p1}$-5)

($P^{p1}$-6)

($P^{p1}$-7)

($P^{p1}$-8)

($P^{p1}$-9)

HS—* in the formulae, $R^{p11}$ and $R^{p12}$ each independently represent a hydrogen atom, a C1 to C5 alkyl group, or a C1 to C5 halogenated alkyl group, $W^{p11}$ represents a single bond, $-O-$, $-COO-$, or a C1 to C5 alkylene group, $t^{p11}$ represents 0, 1, or 2, and if there are a plurality of $R^{p11}$s, $R^{p12}$s, $W^{p11}$s, and/or $t^{p11}$s in the molecule, the referents may be identical or different, $Sp^{p1}$ and $Sp^{p2}$ each independently represent a single bond or a spacer group, $Z^{p1}$ and $Z^{p2}$ each independently represent a single bond, $-O-$, $-S-$, $-CH_2-$, $-OCH_2-$, $-CH_2O-$, $-CO-$, $-C_2H_4-$, $-COO-$, $-OCO-$, $-OCOOCH_2-$, $-CH_2OCOO-$, $-OCH_2CH_2O-$, $-CO-NR^{ZP1}-$, $-NR^{ZP1}-CO-$, $-SCH_2-$, $-CH_2S-$, $-CH=CR^{ZP1}-COO-$, $-CH=CR^{ZP1}-OCO-$, $-COO-CR^{ZP1}=CH-$, $-OCO-CR^{ZP1}=CH-$, $-COO-CR^{ZP1}=CH-COO-$, $-COO-CR^{ZP1}=CH-OCO-$, $-OCO-CR^{ZP1}=CH-COO-$, $-OCO-CR^{ZP1}=CH-OCO-$, $-(CH_2)_z-COO-$, $-(CH_2)_z-OCO-$, $-OCO-(CH_2)_z-$, $-(C=O)-O-(CH_2)_z-$, $-CH=CH-$, $-CF=CF-$, $-CF=CH-$, $-CH=CF-$, $-CF_2-$, $-CF_2O-$, $-OCF_2-$, $-CF_2CH_2-$, $-CH_2CF_2-$, $-CF_2CF_2-$, or $-C\equiv C-$, in the formulae, z at each occurrence independently represents an integer of 1 to 4, $R^{ZP1}$ at each occurrence independently represents a hydrogen atom or a C1 to C4 alkyl group, and if there are a plurality of $R^{ZP1}$s in the molecule, the $R^{ZP1}$s may be identical or different, the * in the formulae represents a bond with $Sp^{p1}$ or $Sp^{p2}$, $A^{p1}$ and $A^{p2}$ each independently represent a group selected from the group consisting of:

($a^p$) a 1,4-cyclohexylene group, one $-CH_2-$ or two or more nonadjacent $-CH_2-$S present in the group may be replaced by $-O-$;

($b^p$) a 1,4-phenylene group, one $-CH=$ or two or more nonadjacent $-CH=$s present in the group may be replaced by $-N=$; and ($c^P$) a 1,4-naphthalenediyl, 2,6-naphthalenediyl, 1,2,3,4-tetrahydronaphthalenediyl, decahydronaphthalenediyl, phenanthrene-2,7-diyl, or anthracene-2,6-diyl group, one —CH= or two or more nonadjacent —CH=s present in the group may be replaced by —N=, $A^{P3}$ represents a group selected from the group consisting of groups ($a^P$), ($b^P$), and ($c^P$) above and a single bond, optionally with one hydrogen atom present in the group ($a^P$), ($b^P$), or ($c^P$), or each of two or more independently, substituted with a cyano group, a halogen atom, a C1 to C8 alkyl group, a C1 to C8 alkoxy group, a C1 to C8 alkenyl group, or —$Sp^{P2}$-$P^{P2}$, $m^{P1}$ represents 0, 1, 2, or 3, and if there are a plurality of $Z^{P1}$s, $A^{P2}$s, $Sp^{P2}$s, and/or $P^{P2}$s, the referents may be identical or different, with the proviso that if $m^{P1}$ is 0 and if $A^{P1}$ is a group other than a naphthalenediyl, phenanthrene-2,7-diyl, or anthracene-2,6-diyl group, $A^{P3}$ represents a group, not a single bond, in general formula (P), any compound represented by general formula (Y) is excluded.

8. The liquid crystal composition according to claim 1, further comprising at least one compound D, wherein the at least one compound D is selected from the group consisting of compounds represented by general formulae (N-1), (N-2), and (N-3) below,

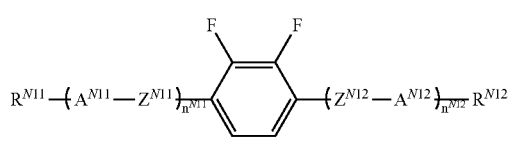
(N-1)

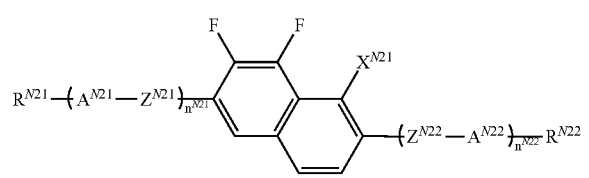
(N-2)

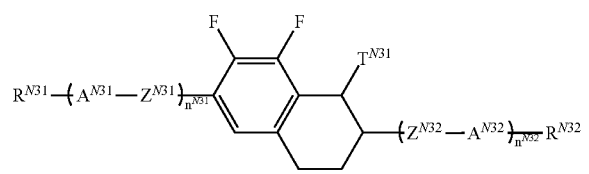
(N-3)

in the formulae, $R^{N11}$, $R^{N12}$, $R^{N21}$, $R^{N22}$, $R^{N31}$, and $R^{N32}$ each independently, represent a C1 to C8 alkyl group, optionally with one —CH$_2$— in the alkyl group, or each of nonadjacent two or more —CH$_2$-s in the alkyl group independently, substituted by —CH=CH—, —C≡C—, —O—, —CO—, —COO—, or —OCO— unless oxygen atoms come consecutively next to each other, $A^{N11}$, $A^{N12}$, $A^{N21}$, $A^{N22}$, $A^{N31}$, and $A^{N32}$ each independently represent a group selected from the group consisting of:

(a) a 1,4-cyclohexylene group, one —CH$_2$— or two or more nonadjacent —CH$_2$—S present in the group may be replaced by —O— unless oxygen atoms come consecutively next to each other;

(b) a 1,4-phenylene group, one or two or more —CH=s present in the group may be replaced by —N=; and (c) a naphthalene-2,6-diyl, 1,2,3,4-tetrahydronaphthalene-2,6-diyl, or decahydronaphthalene-2,6-diyl group, one or two or more —CH=s present in the group may be replaced by —N=, optionally with one hydrogen atom in the group (a), (b), or (c), or each of two or more independently, substituted with a cyano group or a halogen atom, $Z^{N11}$, $Z^{N12}$, $Z^{N21}$, $Z^{N22}$, $Z^{N31}$, and $Z^{N32}$ each independently represent a single bond, —CH$_2$CH$_2$—, —(CH$_2$)$_4$—, —OCH$_2$—, —CH$_2$O—, —COO—, —OCO—, —OCF$_2$—, —CF$_2$O—, —CH=N—N=CH—, —CH=CH—, —CF=CF—, or —C≡C—, $X^{N21}$ represents a hydrogen atom or a halogen atom, $T^{N31}$ represents —CH$_2$— or an oxygen atom, $n^{N11}$, $n^{N12}$, $n^{N21}$, $n^{N22}$, $n^{N31}$, and $n^{N32}$ each independently represent an integer of 0, 1, 2, or 3, with the proviso that $n^{N11}$+$n^{N12}$, $n^{N21}$+$n^{N22}$, and $n^{N31}$+$n^{N32}$ each independently represent 1, 2, or 3, if there are a plurality of $A^{N11}$s, a plurality of $A^{N12}$s, a plurality of $A^{N21}$s, a plurality of $A^{N22}$s, a plurality of $A^{N31}$s, and a plurality of $A^{N32}$s, the referents may be identical or different, and if there are a plurality of $Z^{N11}$s, $Z^{N12}$s, $Z^{N21}$s, $Z^{N22}$s, $Z^{N31}$s, and $Z^{N32}$s, the referents may be identical or different, in general formulae (N-1), (N-2), and (N-3), any compound represented by general formula (Y), (P), or (II) is excluded, in general formulae (N-2) and (N-3), any compound represented by general formula (N-1) is excluded, and in general formula (N-3), any compound represented by general formula (N-2) is excluded.

9. The liquid crystal composition according to claim 1, further comprising at least one compound E, wherein the at least one compound E is represented by general formula (L) below

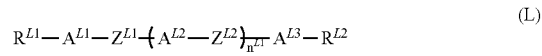
(L)

in general formula (L), $R^{L1}$ and $R^{L2}$ each independently represent a C1 to C8 alkyl group, optionally with one —CH$_2$— in the alkyl group, or each of nonadjacent two or more —CH$_2$-s in the alkyl group independently, substituted by —CH=CH—, —C≡C—, —O—, —CO—, —COO—, or —OCO— unless oxygen atoms come consecutively next to each other, $A^{L1}$, $A^{L2}$, and $A^{L3}$ each independently represent a group selected from the group consisting of:

(a) a 1,4-cyclohexylene group, one —CH$_2$— or two or more nonadjacent —CH$_2$—S present in the group may be replaced by —O— unless oxygen atoms come consecutively next to each other;

(b) a 1,4-phenylene group, one or two or more —CH=s present in the group may be replaced by —N=; and (c) a naphthalene-2,6-diyl, 1,2,3,4-tetrahydronaphthalene-2,6-diyl, or decahydronaphthalene-2,6-diyl group, one or two or more —CH=s present in the group may be replaced by —N=, optionally with one hydrogen atom in the group (a), (b), or (c), or each of two or more independently, substituted with a cyano group or a halogen atom, $Z^{L1}$ and $Z^{L2}$ each independently represent a single bond, —CH$_2$CH$_2$—, —(CH$_2$)$_4$—, —OCH$_2$—, —CH$_2$O—

—COO—, —OCO—, —OCF$_2$—, —CF$_2$O—, —CH=N—N=CH—, —CH=CH—, —CF=CF—, or —C≡C—, $n^{L1}$ represents 0, 1, 2, or 3, if $n^{L1}$ is 2 or 3 and if, therefore, there are a plurality of $A^{L2}$s, the plurality of $A^{L2}$s may be identical or different, and if $n^{L1}$ is 2 or 3 and if, therefore, there are a plurality of $Z^{L2}$s, the plurality of $Z^{L2}$s may be identical or different, any compound represented by general formula (Y), (P), (II), (N-1), (N-2), or (N-3) is excluded.

10. The liquid crystal composition according to claim 1, wherein a percentage of the at least one compound A to the liquid crystal composition is 3% by mass or less.

11. A liquid crystal display element comprising the liquid crystal composition according to claim 1.

12. The liquid crystal display element according to claim 11, wherein the liquid crystal display element is for active-matrix addressing.

13. The liquid crystal display element according to claim 12, wherein the liquid crystal display element is for PSA, PSVA, PS-IPS, or PS-FFS mode.

14. A compound represented by general formula (Y) below

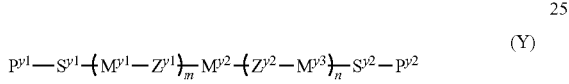
(Y)

in general formula (Y), m represents 0 and n represents 1, $S^{y1}$ and $S^{y2}$ each independently represent a single bond, a linear C1 to C12 alkylene group or a branched C2 to C12 alkylene group, optionally with a hydrogen atom or hydrogen atoms in the alkylene group substituted by a halogen atom, optionally with a —CH$_2$— or —CH$_2$-s in the alkylene group substituted with —CO—, —COO—, —OCO—, —OCOO— or —O—, although without two or more —O-s consecutively next to each other, $M^{y2}$ and $M^{y3}$ each independently represent a group selected from the group consisting of formulae (W-1) and (W-3) to (W-7) below,

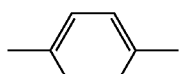
(W-1)

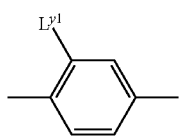
(W-3)

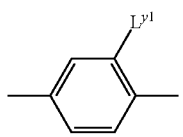
(W-4)

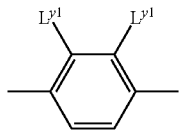
(W-5)

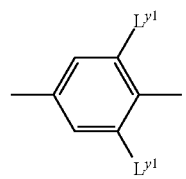
(W-6)

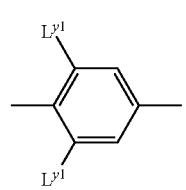
(W-7)

$L^{y1}$ represents a halogen atom, a linear C1 to C30 alkyl group or a branched C3 to C30 alkyl group, optionally with a hydrogen atom or hydrogen atoms in the alkyl group substituted by a halogen atom, optionally with a —CH$_2$— or —CH$_2$-s in the alkyl group substituted with —CO—, —COO—, —OCO—, —OCOO— or —O—, although without two or more —O-s consecutively next to each other, and if there are a plurality of $L^{y1}$s, the $L^{y1}$s may be the same or different, $Z^{y2}$ represents a single bond, $P^{y1}$ and $P^{y2}$ each independently represent a substituent selected from the group consisting of formulae (YP-1) to (YP-2) below,

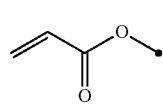
(YP-1)

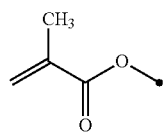
(YP-2)

in formulae (YP-1) and (YP-2), the black dot represents a bond with $S^{y1}$ or $S^{y2}$, at least one of $S^{y1}$, $S^{y2}$ and $L^{y1}$ represents the alkylene group or the alkyl group, and one —CH$_2$— in $S^{y1}$, $S^{y2}$ and $L^{y1}$ is substituted with a group represented by a substructure represented by formula (w-1) or (w-2) below

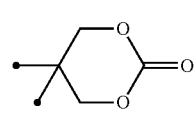
(w-1)

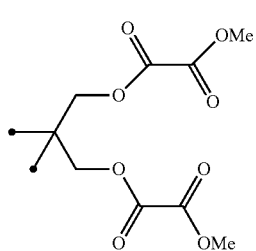 (w-2)
in formula (w-1) or (w-2), the black dots represent bonds, and Me represents a methyl group.
* * * * *